(12) United States Patent
Karnoub et al.

(10) Patent No.: US 9,631,194 B2
(45) Date of Patent: Apr. 25, 2017

(54) METHODS AND COMPOSITIONS FOR USE IN TREATMENT OF FOXP2-RELATED CANCERS

(71) Applicant: Beth Israel Deaconess Medical Center, Boston, MA (US)

(72) Inventors: Antoine E. Karnoub, Boston, MA (US); Benjamin G. Cuiffo, Jamaica Plain, MA (US)

(73) Assignee: BETH ISRAEL DEACONESS MEDICAL CENTER, Boston, MA (US)

( * ) Notice: Subject to any disclaimer, the term of this patent is extended or adjusted under 35 U.S.C. 154(b) by 0 days.

(21) Appl. No.: 14/678,628

(22) Filed: Apr. 3, 2015

(65) Prior Publication Data

US 2015/0284722 A1     Oct. 8, 2015

Related U.S. Application Data

(60) Provisional application No. 61/975,207, filed on Apr. 4, 2014.

(51) Int. Cl.
| | |
|---|---|
| A61K 48/00 | (2006.01) |
| C07H 21/02 | (2006.01) |
| C07H 21/04 | (2006.01) |
| C12N 15/113 | (2010.01) |
| C12Q 1/68 | (2006.01) |
| G01N 33/68 | (2006.01) |
| G01N 33/574 | (2006.01) |

(52) U.S. Cl.
CPC ......... *C12N 15/113* (2013.01); *C12Q 1/6886* (2013.01); *G01N 33/57415* (2013.01); *G01N 33/6875* (2013.01); *C12N 2310/113* (2013.01); *C12Q 2600/158* (2013.01); *G01N 33/57496* (2013.01); *G01N 2800/52* (2013.01)

(58) Field of Classification Search
CPC ... A61K 48/00; C12N 2310/11; C12N 15/113
See application file for complete search history.

(56) References Cited

U.S. PATENT DOCUMENTS

| | | |
|---|---|---|
| 2008/0306006 A1 | 12/2008 | Croce et al. |
| 2010/0035968 A1 | 2/2010 | Rasmussen et al. |
| 2011/0021607 A1* | 1/2011 | Clarke ................. C12Q 1/6886 514/44 A |

FOREIGN PATENT DOCUMENTS

WO    WO 2004022104 A2    3/2004

OTHER PUBLICATIONS

Bao, B., et al., "Targeting CSC-Related miRNAs for Cancer Therapy by Natural Agents," Current Drug Targets, (2012), vol. 13, No. 14, pp. 1858-1868.
Bockmeyer, C.L., et al., "MicroRNA Profiles of Healthy Basal and Luminal Mammary Epithelial Cells are Distinct and Reflected in Different Breast Cancer Subtypes," Breast Cancer Res. Treat. (2011), vol. 130, pp. 735-745.
Borel, F., et al., "Adenosine Triphosphate-Binding Cassette Transporter Genes Up-Regulation in Untreated Hepatocellular Carcinoma is Mediated by Cellular MicroRNAs," Hepatology, (2012), vol. 55, pp. 821-832.
Brenner, B., et al., "MicroRNAs as a Potential Prognostic Factor in Gastric Cancer," World Journal Gastroenterology (2011), vol. 17, No. 35, pp. 3976-3985.
Chen, R., et al., "Regulation of IKKβ by miR-199a Affects NF-κB Activity in Ovarian Cancer Cells," Oncogene (2008), vol. 27, pp. 4712-4723.
Cheng, W., et al., "MicroRNA-199a Targets CD44 to Suppress the Tumorigenicity and Multidrug Resistance of Ovarian Cancer-Initiating Cells," The FEBS Journal, (2012), vol. 279, pp. 2047-2059.
Clarke, R., "Human Breast Cancer Cell Line Xenografts as Models of Breast Cancer—The Immunobiologies of Recipient Mice and the Characteristics of Several Tumorigenic Cell Lines," Breast Cancer Research and Treatment, (1996), vol. 39, pp. 69-86.
Duan, Z., et al., "MicroRNA-199a-3p is Downregulated in Human Osteosarcoma and Regulates Cell Proliferation and Migration," Molecular Cancer Therapeutics (2011), vol. 10, No. 8, pp. 1337-1345.
Fantozzi, A., et al., "Mouse Models of Breast Cancer Metastasis," Breast Cancer Research, (2006), vol. 8. No. 212, pp. 1-11.
Farazi, T.A., et al. "MicroRNA Sequence and Expression Analysis in Breast Tumors by Deep Sequencing," Cancer Res. (2011), vol. 71, No. 13, pp. 4443-4453.
Feber, A., "MicroRNA Prognostic Signature for Nodal Metastases and Survival in Esophageal Adenocarcinoma," Ann. Thorac. Surg., (2011), vol. 91, pp. 1523-1530.
Fisher, S.E., et al., "FOXP2 as a Molecular Window into Speech and Language," Trends in Genetics, (2009), vol. 25, No. 4, pp. 166-177.
Fornari, F., et al., "MiR-199a-3p Regulates mTOR and c-Met to Influence the Doxorubicin Sensitivity of Human Hepatocarcinoma Cells," Cancer Research, (2010), vol. 70, No. 12, pp. 5184-5193.
Iorio, M.V., et al. "MicroRNA Signatures in Human Ovarian Cancer," Cancer Res. (2007), vol. 67, No. 18, pp. 8699-8707.
Konopka, G., et al., "Human-Specific Transcriptional Regulation of CNS Development Genes by FOXP2," Nature, (2009), vol. 462, pp. 213-217.
Li, S. et al., "Transcriptional and DNA Binding Activity of the Foxp1/2/4 Family is Modulated by Heterotypic and Homotypic Protein Interactions," Molecular Cellular Biology, (2004), vol. 24, No. 2, pp. 809-822.
Mascaux, C., et al., "Evolution of MicroRNA Expression During Human Bronchial Squamous Carcinogenesis," European Respiratory Journal, (2009), vol. 33, pp. 352-359.
Mudduluru, G., et al., "Regulation of Axl Receptor Tyrosine Kinase Expression by miR-34a and miR-199a/b in Solid Cancer," Oncogene, (2011), vol. 30, pp. 2888-2899.

(Continued)

*Primary Examiner* — Amy Bowman
(74) *Attorney, Agent, or Firm* — Morgan, Lewis & Bockius LLP

(57) ABSTRACT

The present invention relates, in part, to the treatment and prevention of cancers by administering agents that modulate the activity or expression of microRNAs.

14 Claims, 28 Drawing Sheets

(56) References Cited

OTHER PUBLICATIONS

Myatt, S.S., et al., "The Emerging Roles of Forkhead Box (Fox) Proteins in Cancer," Nature Review Cancer, vol. 7, pp. 847-859.
Rane, S., et al., "Downregulation of miR-199a Derepresses Hypoxia-Inducible Factor-1alpha and Sirtuin 1 and Recapitulates Hypoxia Preconditioning in Cardiac Myocytes," Circ Res, (2009), vol. 104, pp. 879-886.
Sakurai, K., et al. "MicroRNAs miR-199a-5p and -3p Target the Brm Subunit of SWI/SNF to Generate a Double-Negative Feedback Loop in a Variety of Human Cancers,", Cancer Research, (2010), vol. 71, No. 5 pp. 1680-1689.
Schwarzenbach, H., et al., "Diagnostic Potential of PTEN-Targeting miR-214 in the Blood of Breast Cancer Patients," Breast Cancer Res. Treat, (2012), vol. 134, pp. 933-941.
Shatseva, T., et al., "MicroRNA miR-199a-3p Regulates Cell Proliferation and Survival by Targeting Caveolin-2," Journal of Cell Science, (2011), vol. 124, pp. 2826-2836.
Shimono Y, et al., "Down-Regulation of miRNA-200c Links Breast Cancer Stem Cells with Normal Stem Cells," Cell, (2009), vol. 138 No. 3, pp. 592-603.
Shu, W., et al., "Foxp2 and Foxp1 Cooperatively Regulate Lung and Esophagus Development," Development, (2007), vol. 134, pp. 1991-2000.
Shu, W., et al., "Characterization of a New Subfamily of Winged-helix/Forkhead (Fox) Genes that are Expressed in the Lung and Act as Transcriptional Repressors," The Journal of Biological Chemistry, (2001), vol. 276, No. 29, pp. 27488-27497.
Song, G., et al., "miR-199a Regulates the Tumor Suppressor Mitogen-Activated Protein Kinase Kinase Kinase 11 in Gastric Cancer," Biol Pharm Bull, (2010), vol. 33, No. 11, pp. 1822-1827.
Spiteri, E., et al., "Identification of the Transcriptional Targets of FOXP2, a Gene Linked to Speech and Language, in Developing Human Brain," The American Journal of Human Genetics (2007), vol. 81, pp. 1144-1157.
Tsui, D., et al., "FoxP2 Regulates Neurogenesis During Embryonic Cortical Development," The Journal of Neuroscience, (2013), vol. 33, pp. 244-258.
Tsukigi, M., et al., "Re-Expression of miR-199a Suppresses Renal Cancer Cell Proliferation and Survival by Targeting GSK-3β," Cancer Letters, (2012), vol. 315, pp. 189-197.
Vernes, S.C., et al., "Foxp2 Regulates Gene Networks Implicated in Neurite Outgrowth in the Developing Brain," PLoS Genetics, (2011), vol. 7, No. 7, pp. 1-17.
Volinia, S., et al., "A microRNA Expression Signature of Human Solid Tumors Defines Cancer Gene Targets," Proc. Natl. Acad. Sci., (2006), vol. 103, No. 7, pp. 2257-2261.
Volinia, S., et al., "Breast Cancer Signatures for Invasiveness and Prognosis Defined by Deep Sequencing of VlicroRNA," Proc. Natl. Acad. Sci., (2012), vol. 109, No. 8, pp. 3024-3029.
Wan, D., et al., "Aberrant Expression of miR-199a-3p and its Clinical Significance in Colorectal Cancers," Med. Oncol., (2013), vol. 30, No. 378, pp. 1-7.
Yang, H., et al., "MicroRNA Expression Profiling in Human Ovarian Cancer: miR-214 Induces Cell Survival and Cisplatin Resistance by Targeting PTEN," Cancer Research, (2008), vol. 68, pp. 425-433.
Zhang, Y., et al., "Functional Screening for miRNAs Targeting Smad4 Identified miR-199a as a Negative Regulator of TGF-β Signalling Pathway," Nucleic Acids Research, (2012), vol. 40, pp. 9286-9297.

\* cited by examiner

METHODS AND COMPOSITIONS FOR USE IN TREATMENT OF FOXP2-RELATED CANCERS

RELATED APPLICATIONS

This application claims the benefit of U.S. Provisional Patent Application No. 61/975,207, filed Apr. 4, 2014, which is hereby incorporated by reference in its entirety.

DESCRIPTION OF THE TEXT FILE SUBMITTED ELECTRONICALLY

The contents of the text file submitted electronically herewith are incorporated herein by reference in their entirety: A computer readable format copy of the Sequence Listing (BID-003-SequenceListing.txt, date recorded: Jun. 11, 2015, filed size 7 kilobytes).

FIELD OF THE INVENTION

This invention relates to compositions and methods for treatment of cancer, for example, using agents that target microRNAs.

BACKGROUND

Cancer treatments lose efficacy as disease spreads or develops from a manageable stage. Without early detection and treatment, the likelihood of surviving cancer is lower and the quality of a patient's life is severely lessened. Accordingly, appropriate treatments for aggressive cancers remain an unmet need in oncology.

Further still, another major limitation of current treatments for cancer is the selection of appropriate active agents for a patient. It is common that sub-optimal chemotherapy is provided to a patient, resulting in unsuccessful treatment. For example, adequate assays and biomarkers for assessing patient tumors are lacking, resulting in a reduction in the likelihood of therapeutic success. This is especially so in the context of more aggressive tumors, which often call for aggressive and swift therapy.

Therefore, there remains a need for methods for treating and/or diagnosing aggressive cancer types.

SUMMARY OF THE INVENTION

Accordingly, the present invention provides, in part, treatment and diagnostics methods for aggressive cancer types, including, for example, breast and bone cancers.

In some aspects, the present invention provides for treatments of aggressive cancers, including those of a later stage or type and/or those which have, or which are likely to, metastasize, with agents that inhibit microRNAs (miRs) that underlie deregulation of genes that are linked to tumor aggressiveness. For example, in some embodiments, FOXP2 is deregulated by various miRs, including miR-199a, miR-214, miR-34a, miR-762, miR-1915, and Let-7b, and the present therapeutic methods target this deregulation in the treatment of an aggressive cancer.

In one aspect, a method for treating or preventing an aggressive cancer, comprising administering a micro-RNA inhibitor, by way of non-limiting example, an optionally modified antisense oligonucleotide, of one or more of miR-199a, miR-214, miR-34a, miR-762, miR-1915, and Let-7b to a subject in need thereof is provided. In various embodiments antisense agents, including those with sufficient complementarity to target one or more of miR-199a, miR-214, miR-34a, miR-762, miR-1915, and Let-7b are administered to a patient that is afflicted with an aggressive tumor.

Further, in other aspects, the present invention provides for methods of evaluating a patient's tumor, for example, diagnostically, to direct patient treatment. For example, in some embodiments, detection of a deregulation of FOXP2, or an upregulation of one or more of miR-199a, miR-214, miR-34a, miR-762, miR-1915, and Let-7b is indicative of an aggressive cancer and may direct aggressive treatment. In some embodiments, the diagnostic methods are useful as a companion to the present miR-inhibiting agents.

Percentage of apoptotic cells as assessed by 7AAD staining/FACS analysis. Data is representative of n>3. Panel E shows a mammosphere formation assay. Mean number of mammospheres in primary (1ary), secondary (2ary), and tertiary (3ary) passaged cultures ±SEM are shown (each set of three bars corresponds to (left-to-right): $BCC^{null}$ (first bar), $BCC^{199a}$ (second bar), and $BCC^{199a/214}$ (third bar), respectively. Data is representative of n=3. Panel F shows Left: representative ALDEFLUOR analyses conducted on the indicated cell lines. DEAB, a specific inhibitor of ALDH1, was used as a control. Right: Quantification of ALDEFLUOR assays. Data is representative of n=3. Panel G shows tumor-initiation analyses. Table indicating the number of tumors initiated (>0.05 g) and total number of tumor cell injections for each cell dilution (#cells/injection). Panel H shows ALDEFLUOR-based measurements of ALDH1-positive cells in MCF7/Ras, T47D, and MDA-MB-435 cells harboring empty control vector (null) or miR-199a-expression construct (199a). (*)-indicates P<0.05; ()-indicates P<0.01, (*)-indicates P<0.001 in 2-tailed student's t-test.

Figure 4:
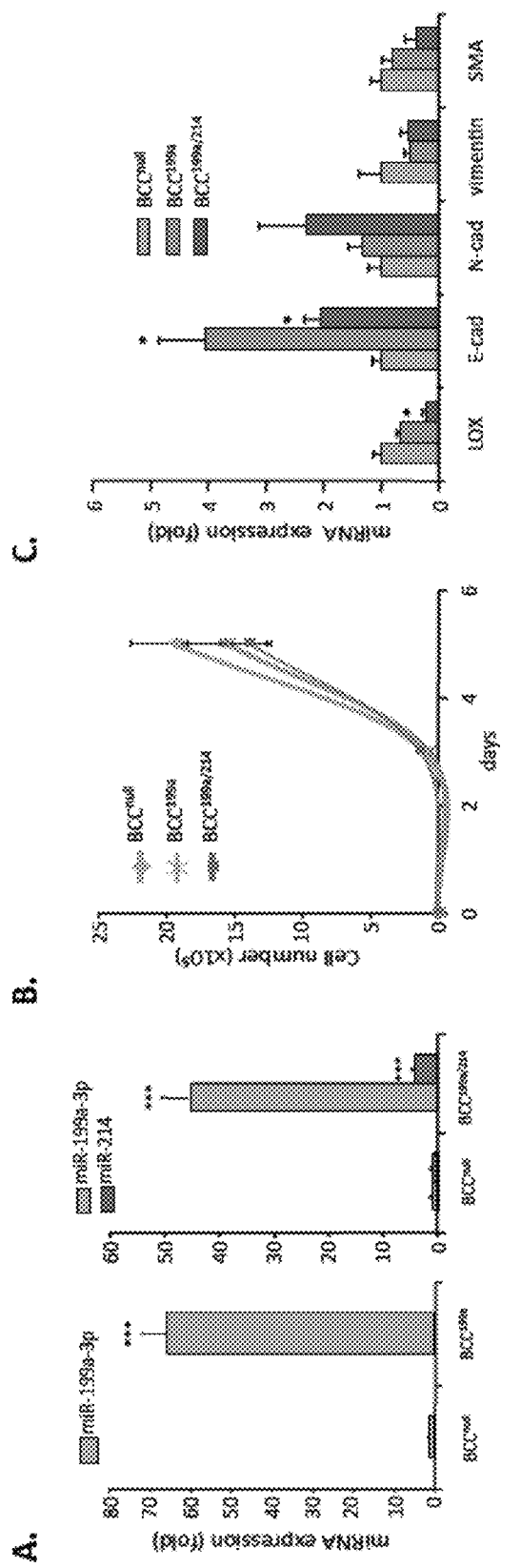
Figure 4:
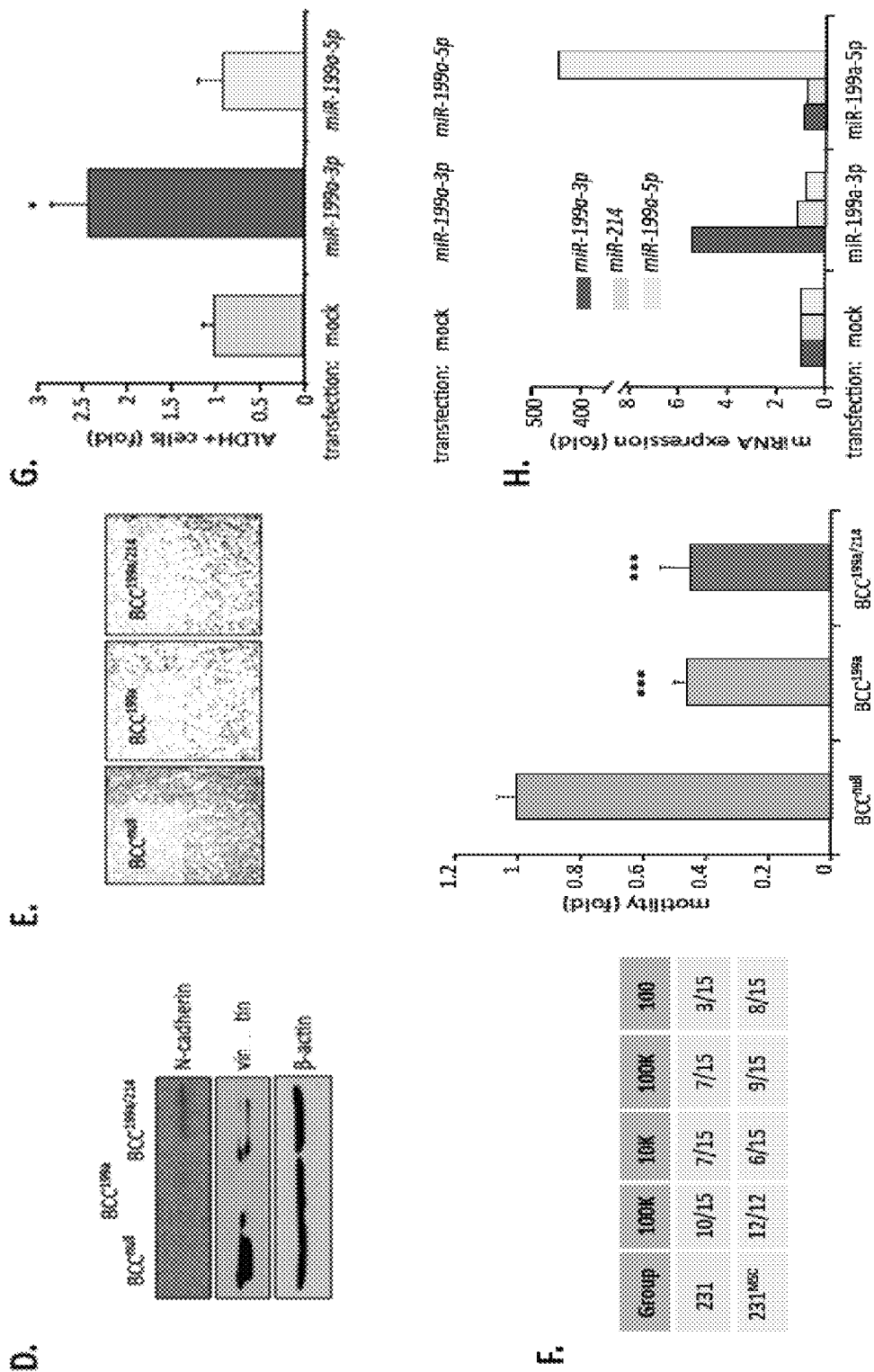

FIG. 4 shows characterization of $BCC^{199a}$ and $BCC^{199a/214}$. Panel A shows verification of the indicated miR levels in MDA-MB-231 cell lines stably expressing A1 or A2 locus miRs by rtPCR-ΔΔct (n=3 repeats). Panel B shows proliferation trends of miR-expressing MDA-MB-231 cell lines in complete media (n=6 repeats). Error bars represent ±SEM. Panel C shows rtPCR-ΔΔct probing for mesenchymal and epithelial markers in miR-expressing cells (each set of three bars corresponds to (left-to-right): $BCC^{null}$ (first bar), $BCC^{199a}$ (second bar), and $BCC^{199a/214}$ (third bar), respectively). Data is represented as mean fold-enrichment ±SEM (n=3 repeats). Panel D shows Western blots for the indicated proteins in control and miR-overexpressing cell lines. Panel E shows Boyden chamber motility assays (0.8 um pores). Upper: representative micrographs of stained membranes of the indicated groups. Lower: motility was calculated by imaging and counting total migrated cells and is displayed as fold relative to vector controls ($BCC^{null}$; n=6 repeats). Panel F shows a table indicating the number of tumors initiated (>0.05 g) and total number of injections for each dilution of control MDA-MB-231 cells (231) and BCC-stimulated MDA-MB-231 cells ($231^{MSC}$). Panel G shows relative fold-change in the percentage of ALDH1-positive cells in the indicated groups harboring miR mimics. Data is represented as mean fold-enrichment compared to mock transfection ±SEM (n=3 repeats). Panel H shows rtPCR-ΔΔct to verify increased levels of mature miR-199a-3p or -5p in cells used in Panel G (each set of three bars corresponds to (left-to-right): miR-199a-3p (first bar), miR-214 (second bar), and miR-199a-5p (third bar), respectively). (*)-indicates P<0.05; (***)-indicates P<0.001 in 2-tailed student's t-test.

Figure 5:
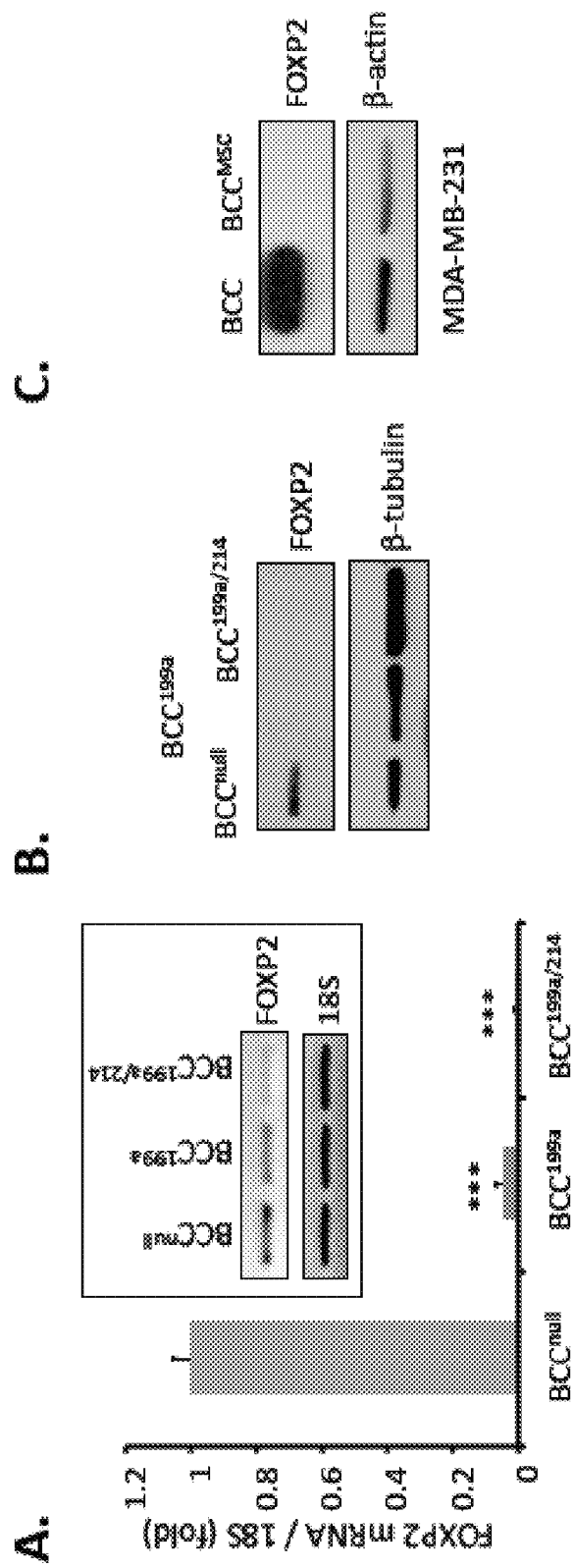
Figure 5:
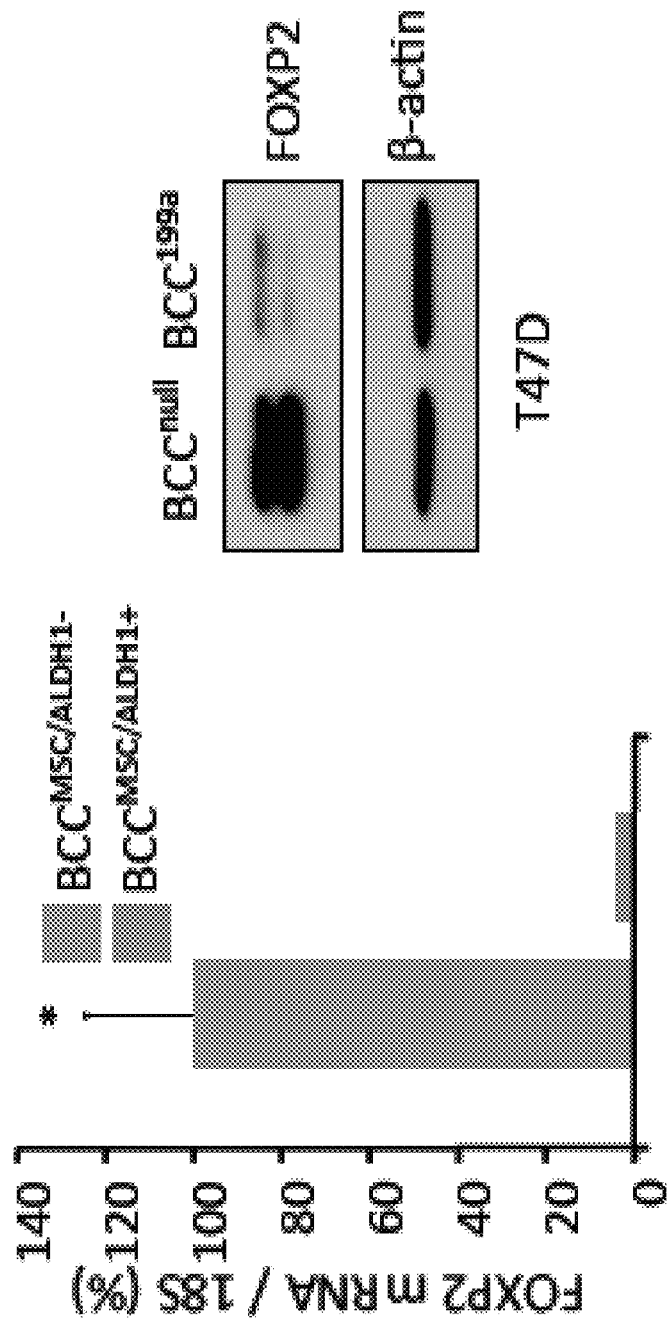

FIG. 5 shows a targeted PCR screen identified FOXP2 as a putative target in $BCC^{199a}$ and $BCC^{199a/214}$. Panel A shows rtPCR-ΔΔct analyses on FOXP2 in the indicated cell lines. Data is representative of n=3 independent repeats. Inset: DNA gel output from the aforementioned rtPCR-ΔΔct reactions. Panel B shows representative Western blot probing for FOXP2 in lysates of the indicated cell lines. β-tubulin was used as a loading control (n=3 independent repeats). Panel C shows representative Western blot probing for FOXP2 in lysates of control or MSC-activated MDA-MB-231 cells. β-actin was used as a loading control (n=3 independent repeats). Panel D shows representative rtPCR-ΔΔct analysis showing relative abundance of FOXP2 mRNA in FACS-fractionated ALDH1-positive (second bar) vs. ALDH1-negative (first bar) MSC-activated MDA-MB-231 cells (n=3 independent repeats). Panel E shows representative Western blot analysis for FOXP2 in the lysates T47D cells controls or overexpressing miR-199a (n=2 repeats). β-actin was used as a loading control. (*)-indicates P<0.05; ()-indicates P<0.01, (*)-indicates P<0.001 in 2-tailed student's t-test.

Figure 6:
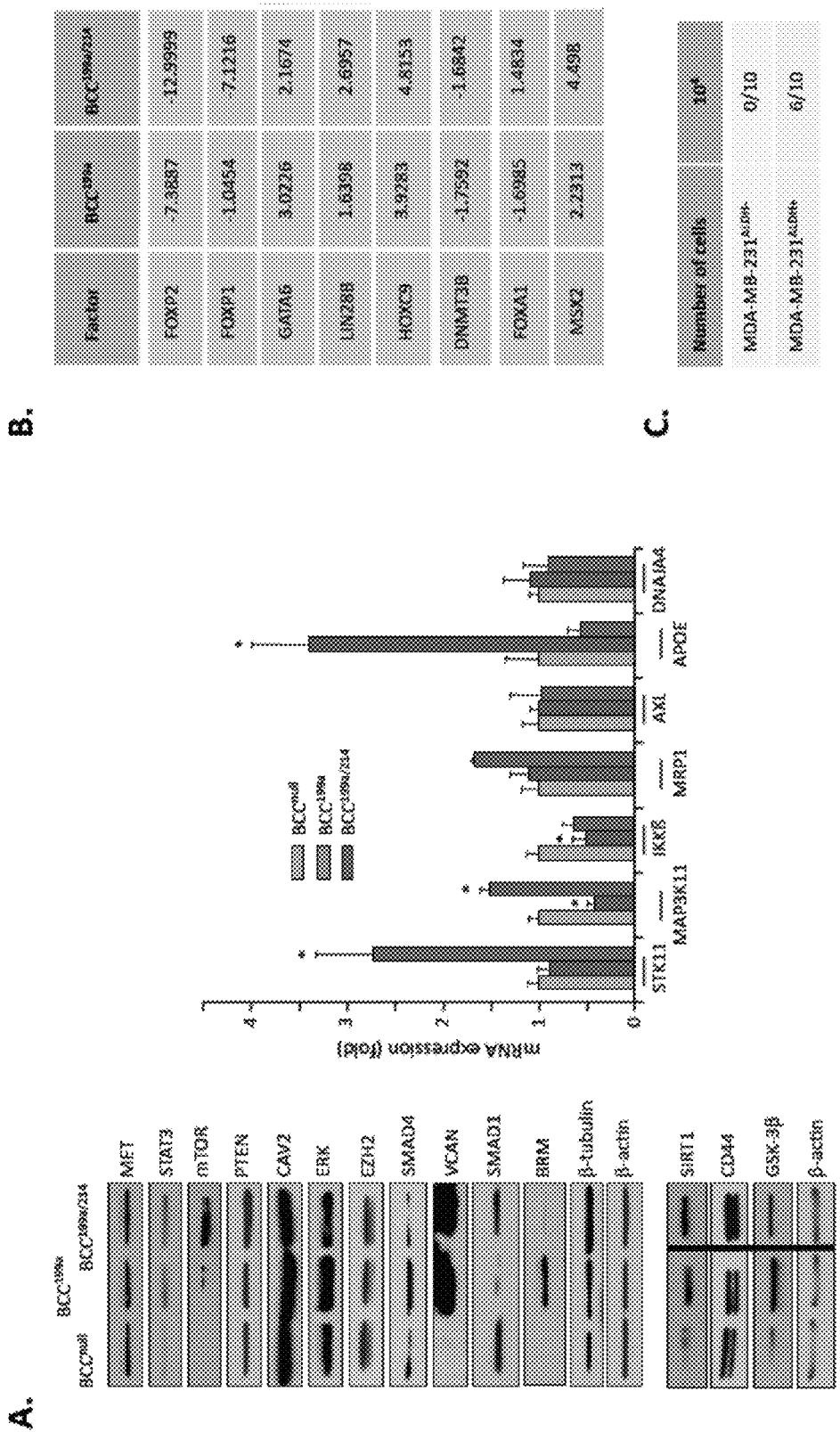

FIG. 6 shows target characterization in $BCC^{199a}$ and $BCC^{199a/214}$. Panel A, left shows Western blots probing lysates derived from $BCC^{null}$, $BCC^{199a}$, or $BCC^{199a/214}$ with antibodies against the indicated proteins. Panel A, right shows rtPCR-ΔΔct utilizing primers designed to recognize additional previously published A2-locus miR targets (each set of three bars corresponds to (left-to-right): $BCC^{null}$ (first bar), $BCC^{199a}$ (second bar), and $BCC^{199a/214}$ (third bar), respectively). Panel B shows combined results of qRTPCR arrays probing $BCC^{null}$, $BCC^{199a}$, or $BCC^{199a/214}$ utilizing primer-pairs designed to recognize mRNA of stem-cell-associated transcription factors. Shown are expression levels (in folds) compared to $BCC^{null}$, with p-values <0.05. Panel C shows a table displaying number of tumors initiated (>0.05 g) from injections of $10^4$ of ALDH1-positive or ALDH1-negative MDA-MB-231 cells. (*)-indicates P<0.05.

Figure 7:
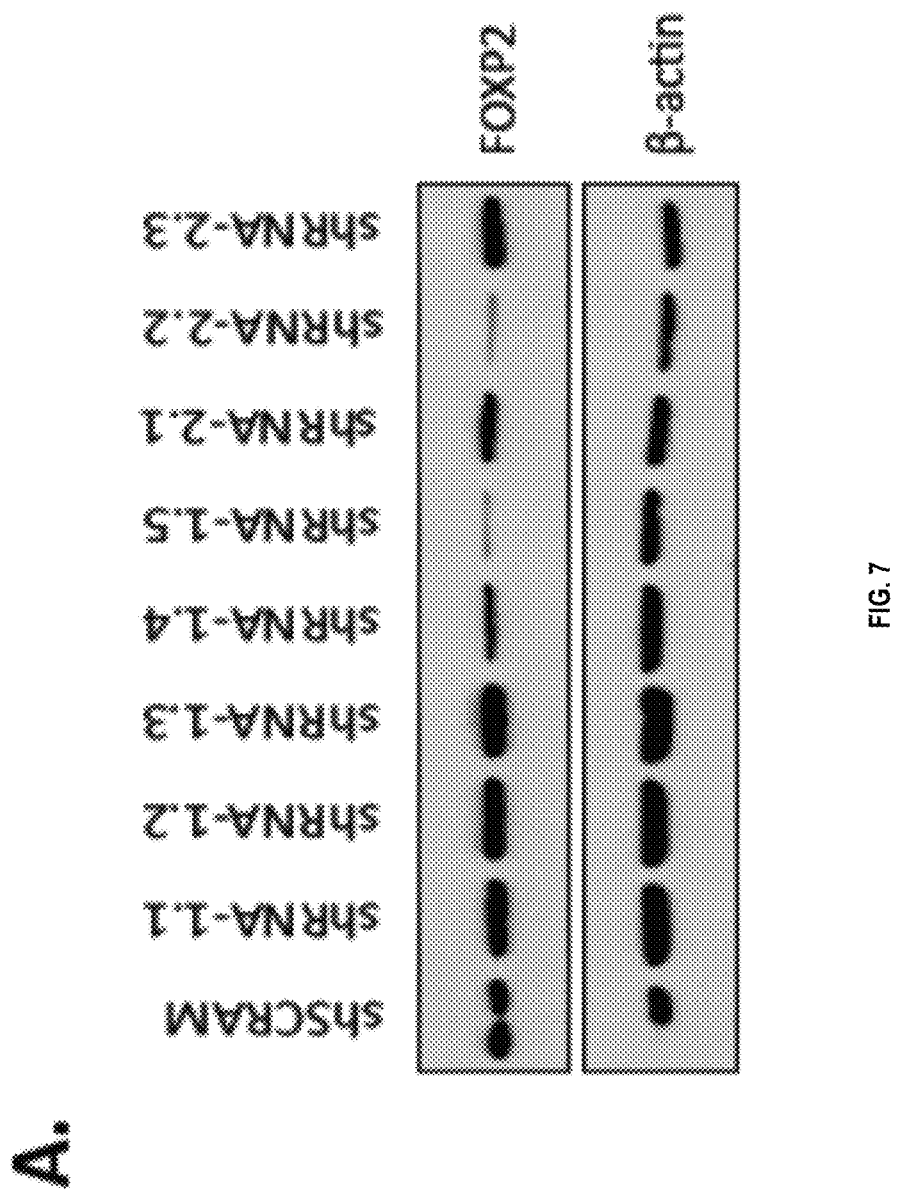
Figure 7:
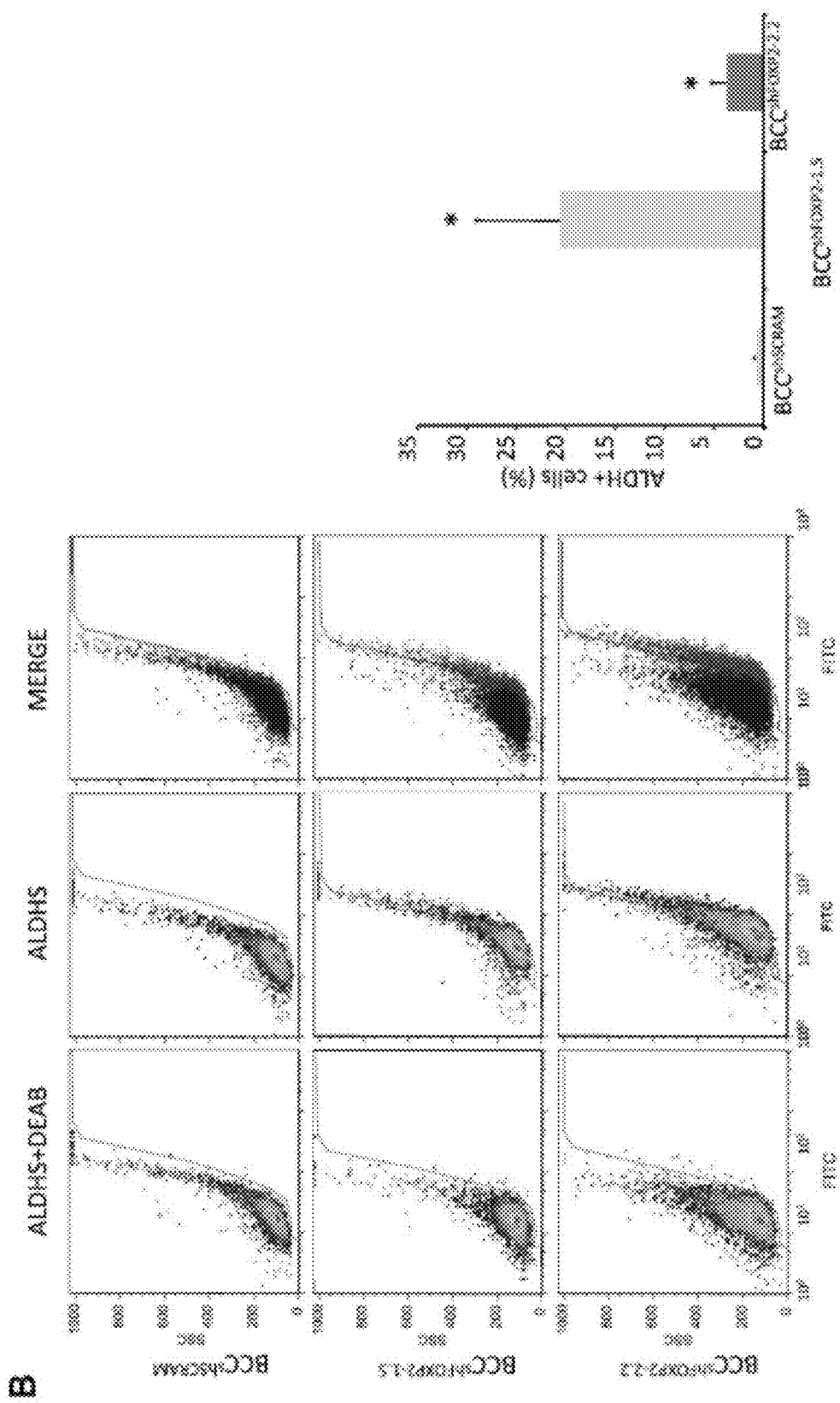
Figure 7:
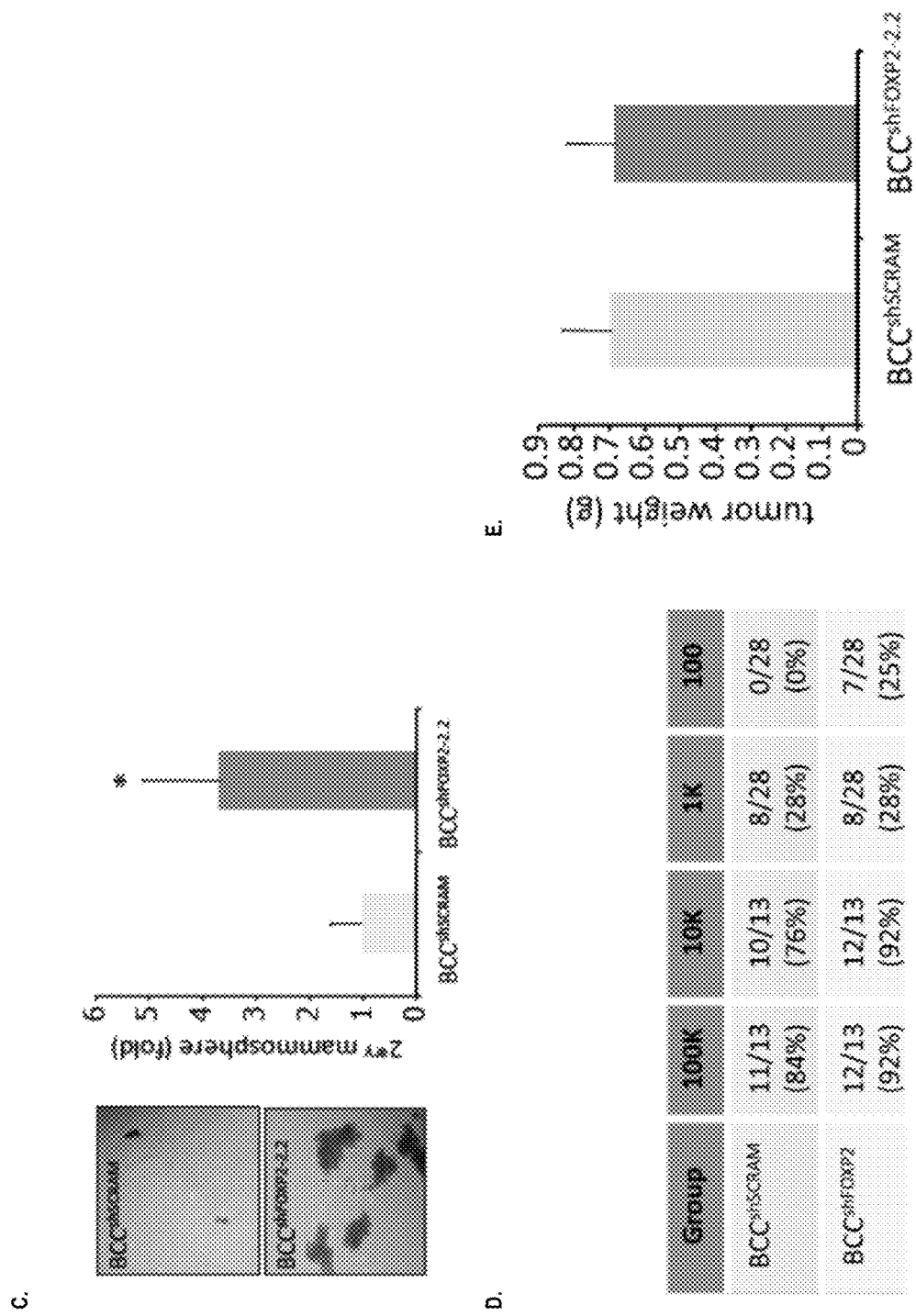
Figure 7:
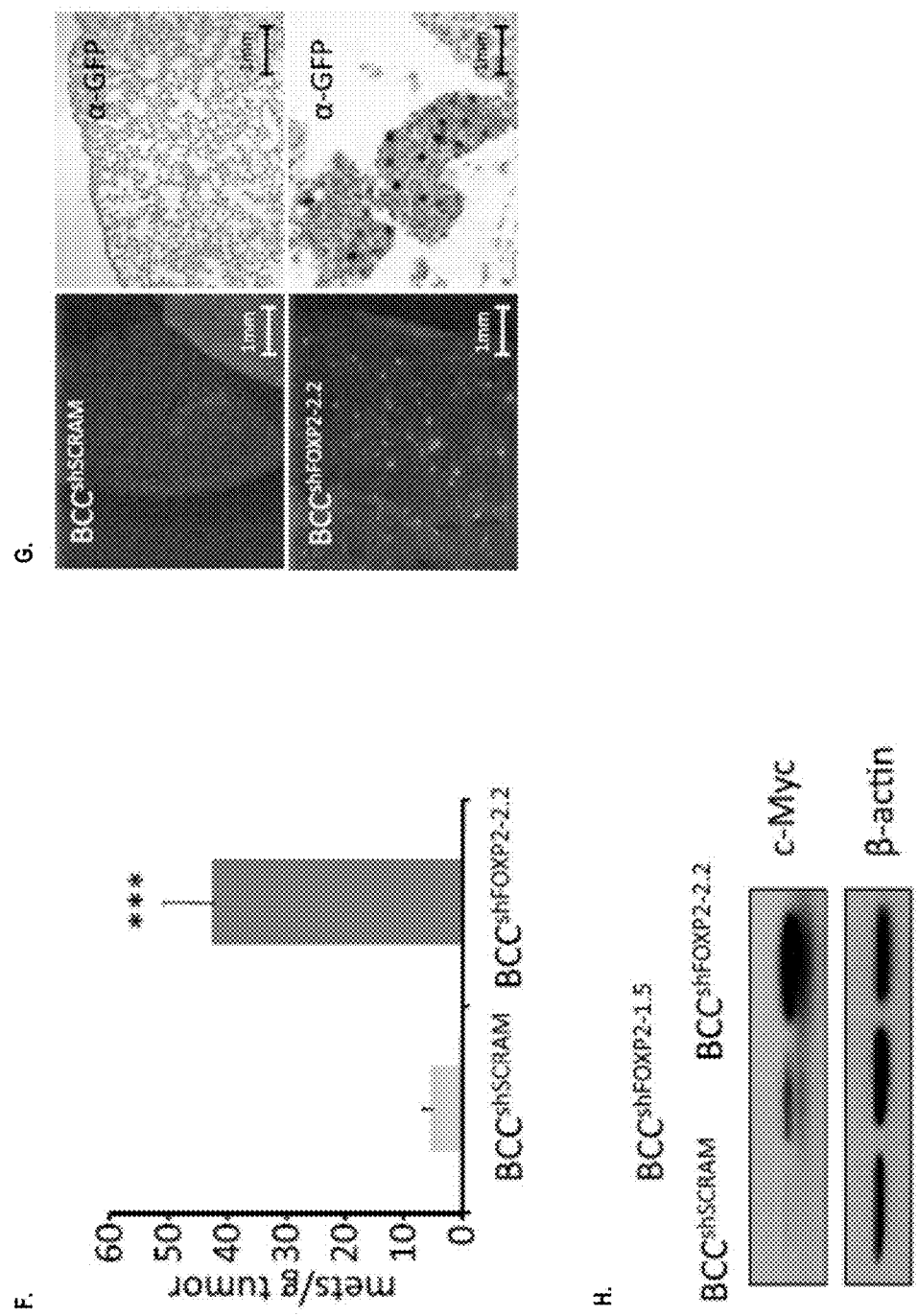

FIG. 7 shows FOXP2 downregulation drives cancer stem cell phenotypes and metastasis. Panel A shows representative Western blot analysis probing FOXP2 expression after knockdown by the indicated shRNAs. Panel B shows representative ALDEFLUOR analyses conducted on the indicated cell lines (n>3 repeats) highlighting the percentage of ALDH1-positive cells in each condition. DEAB, a specific inhibitor of ALDH1, was used as a control. Panel C shows mammosphere formation assays; representative images of secondary mammospheres and their quantification. Data is representative of n>3 repeats. Panel D shows tumor-initiation analyses; table indicates the number of tumors initiated (>0.05 g) and the total number of injections for each cell dilution (#cells/injection) of shFOXP2-2.2 or scrambled-hairpin-expressing MDA-MB-231 cells ($BCC^{shsRAM}$). Panel E shows mean weight (grams) ±SEM of primary tumors from the indicated groups isolated at matched time points from athymic Nude mice 8-14 weeks after subcutaneous implantation of equivalent numbers of the indicated cancer cells. Panel F shows average number of GFP-positive lung metastases ±SEM observed per gram of primary tumor burden per mouse; n=16 mice for $BCC^{shSCRAM}$ and n=25 mice for $BCC^{shFOXP2-2.2}$. Panel G shows representative images of GFP-positive colonies and anti-GFP IHC in the lungs of $BCC^{shSCRAM}$ or $BCC^{shFOXP2-2.2}$ mice in Panels E and F. (*)-indicates P<0.05; ()-indicates P<0.01, (*)-indicates P<0.001 in 2-tailed student's t-test. Panel H shows representative Western blot for c-myc in whole-cell lysates of the indicated MDA-MB-231 cells. β-actin was used as a loading control (n=3).

Figure 8:
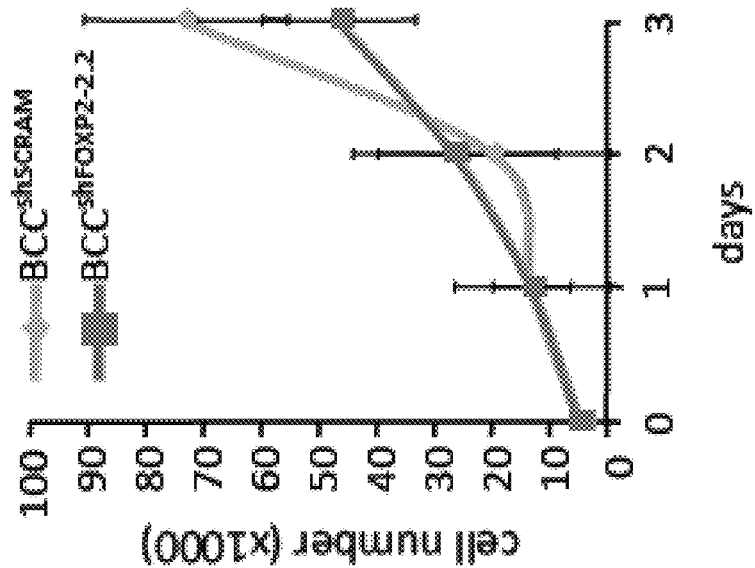
Figure 8:
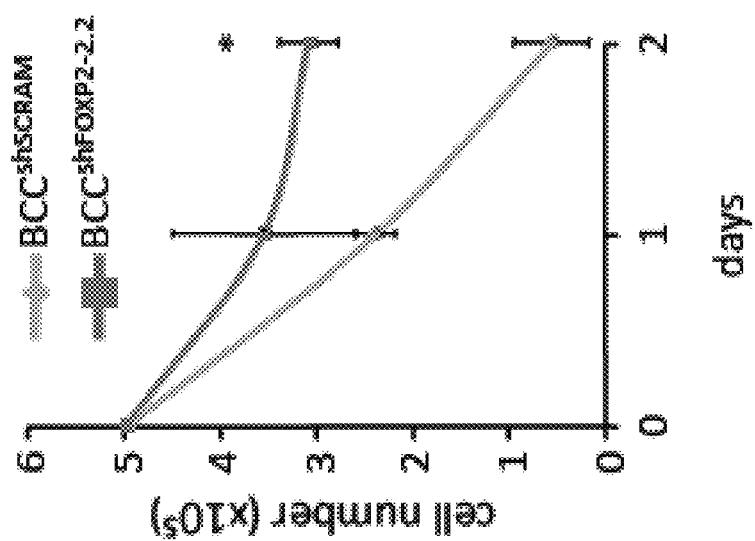

FIG. 8 shows knockdown of FOXP2 phenocopies A2-locus miR effects. Panel A shows minimal-serum tumbling assay. Average numbers of viable cells determined by trypan blue exclusion test are shown ±SEM (n=3 repeats). Panel B shows proliferation of $BCC^{shscRAM}$ and $BCC^{shFOXP2-2.2}$ in complete media ±SEM (n=6 repeats). (*)-indicates P<0.05.

Figure 9:
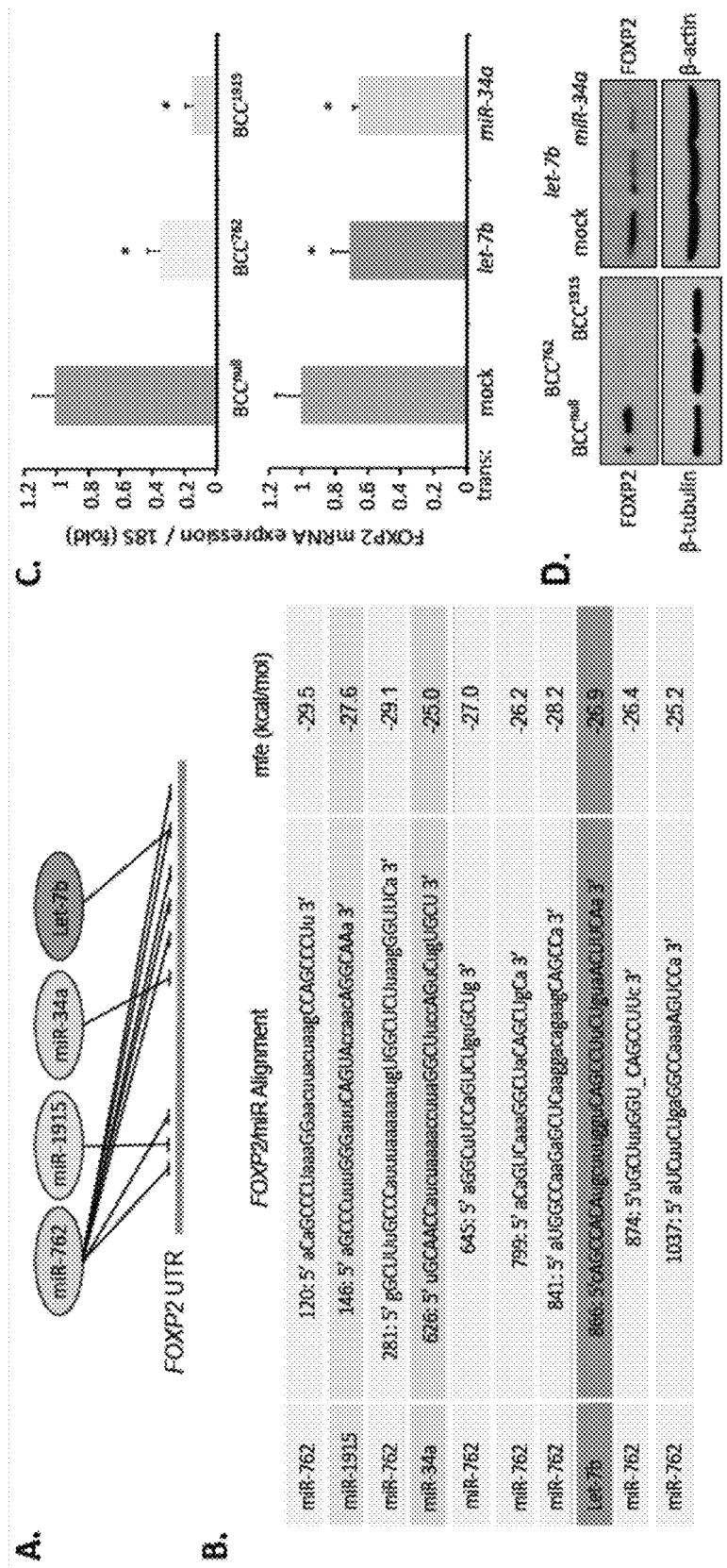
Figure 9:
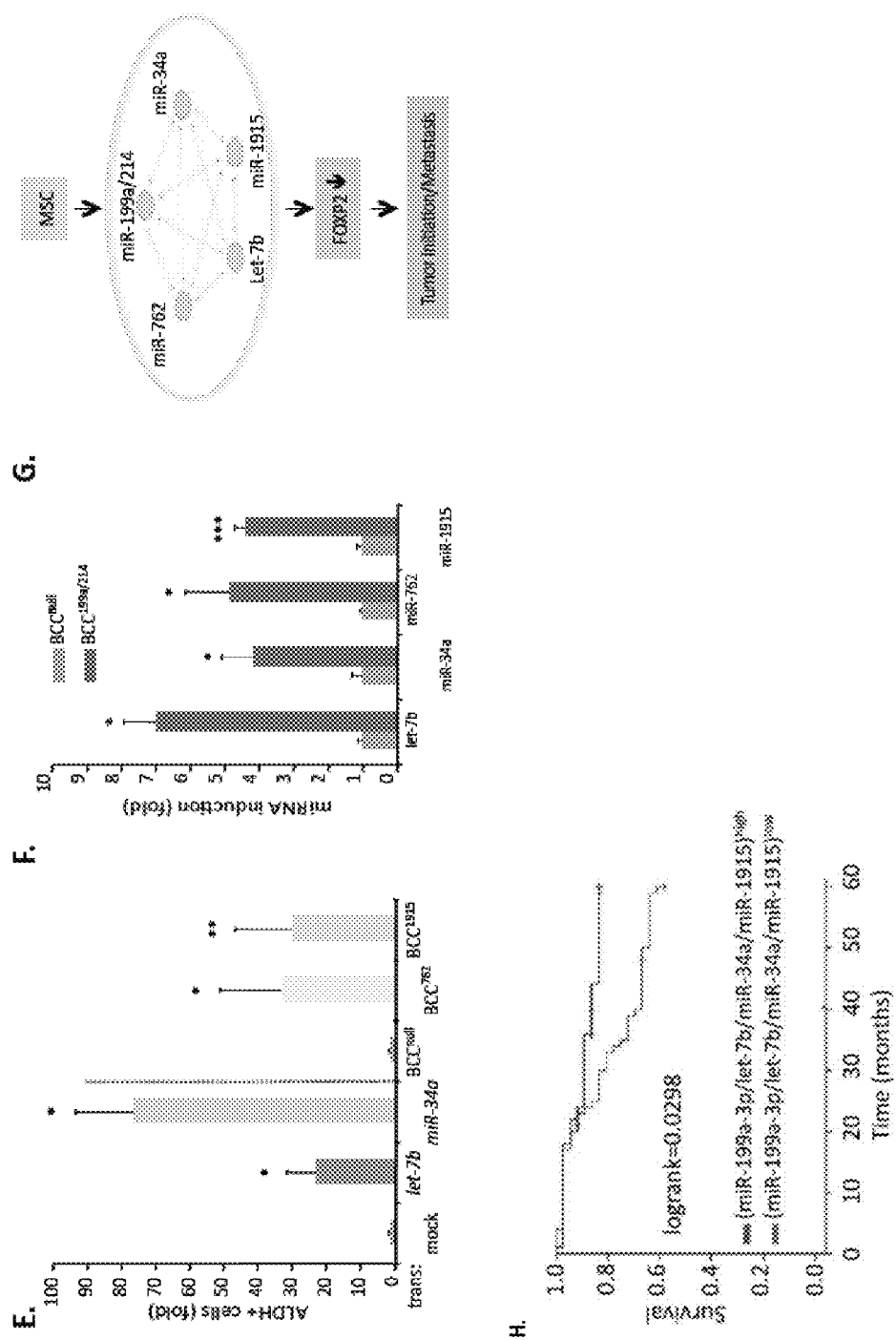
Figure 9:
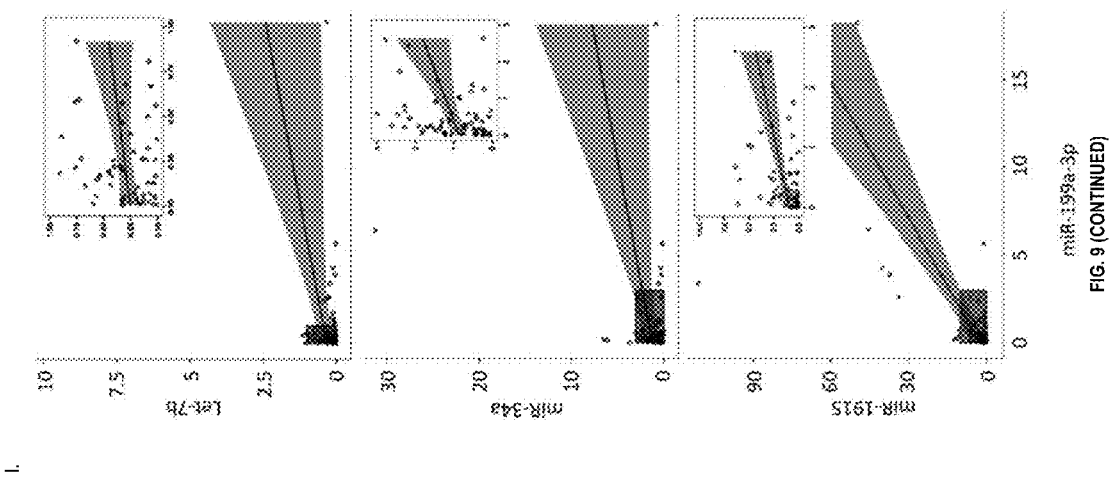

FIG. 9 shows MSC-induced miRNAs converge on FOXP2. Panels A and B show predicted MSC-induced miRNA seed sequence targeting of the proximal (5'-most ~1 kb) FOXP2 3' UTR. Displayed is data from RNAhybrid (Kruger and Rehmsmeier, Nucleic Acids Res 34, W451-454, 2006); mfe=mean free energy of the predicted binding in kcal/mol. Panel C shows Upper: rtPCR-ΔΔct probing relative FOXP2 mRNA levels in MDA-MB-231 cells stably expressing miR-762 ($BCC^{762}$), miR-1915 ($BCC^{1915}$), or controls ($BCC^{null}$). Lower: rtPCR-ΔΔct probing relative FOXP2 mRNA levels in MDA-MB-231 cells transiently transfected with miRNA mimics of miR-let-7b or miR-34a compared to mock. Data shown is representative of n>3 for all groups. Panel D shows Western blots showing FOXP2 protein levels from lysates derived from $BCC^{null}$, $BCC^{762}$ or $BCC^{1915}$ (left) or from lysates derived from transient transfection of miR-let-7b or miR-34a miRNA mimics (right). Panel E shows percentage of ALDH1-positive cells in the indicated groups as in Panel D. Panel F shows expression levels of the indicated miRs in $BCC^{null}$ and $BCC^{199a/214}$. Panel G shows a model. Without wishing to be bound by theory, MSC stimulation of BCCs activates the expression of a set of miRNAs, led my miR-199a-3p, which converges on FOXP2, the downregulation of which is sufficient to promote CSC traits and metastasis. (*)-indicates P<0.05; ()-indicates P<0.01, (*)-indicates P<0.001 in 2-tailed student's t-test. See also FIG. 10. Panel H shows median fold change (FC) of the combined expression levels of miR-199a-3p, miR-34a, miR-let-7b, and miR-1915 stratify the population into two groups with different 5 year survival probability (n=73). Panel I shows Pearson coefficient of miRNA fold changes showed significant correlations between expression levels of miR-199a-3p and miR-34a, miR-let-7b, and miR-1915 as determined by rtPCR-ΔΔct on clinical samples.

Figure 10:
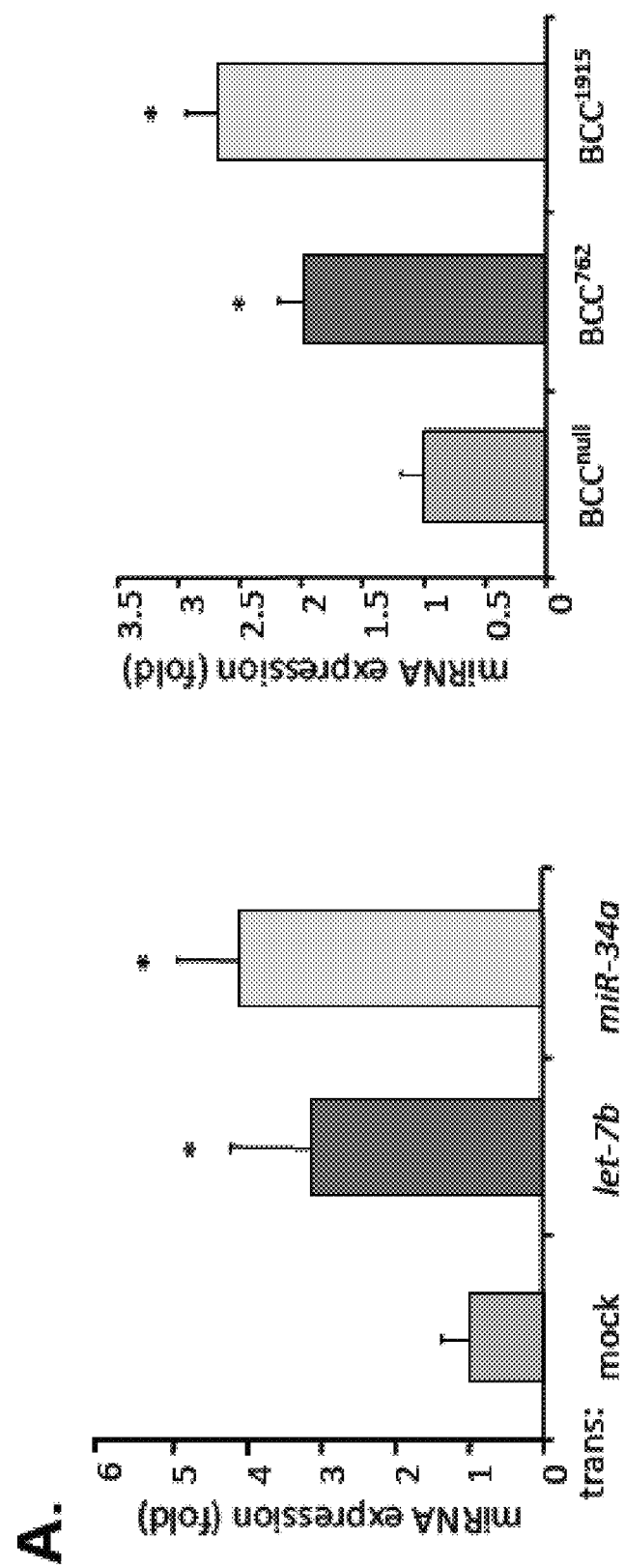

FIG. 10 shows verification of additional miR-expressing cell lines. Panel A shows rtPCR-ΔΔct probing relative miRNA levels as indicated. Data is represented as mean fold ±SEM compared to indicated controls. (*)-indicates P<0.05.

Figure 11:
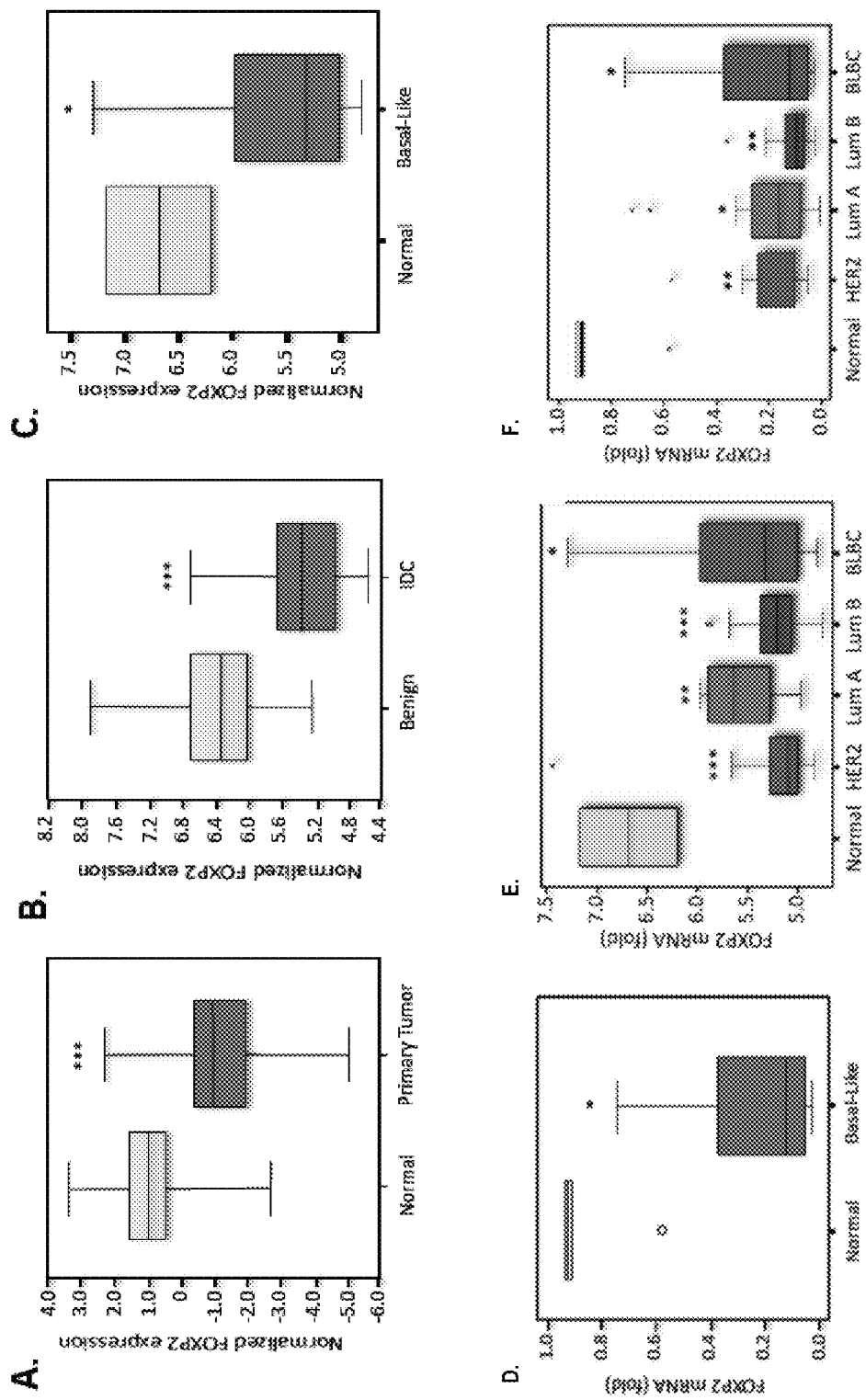
Figure 11:
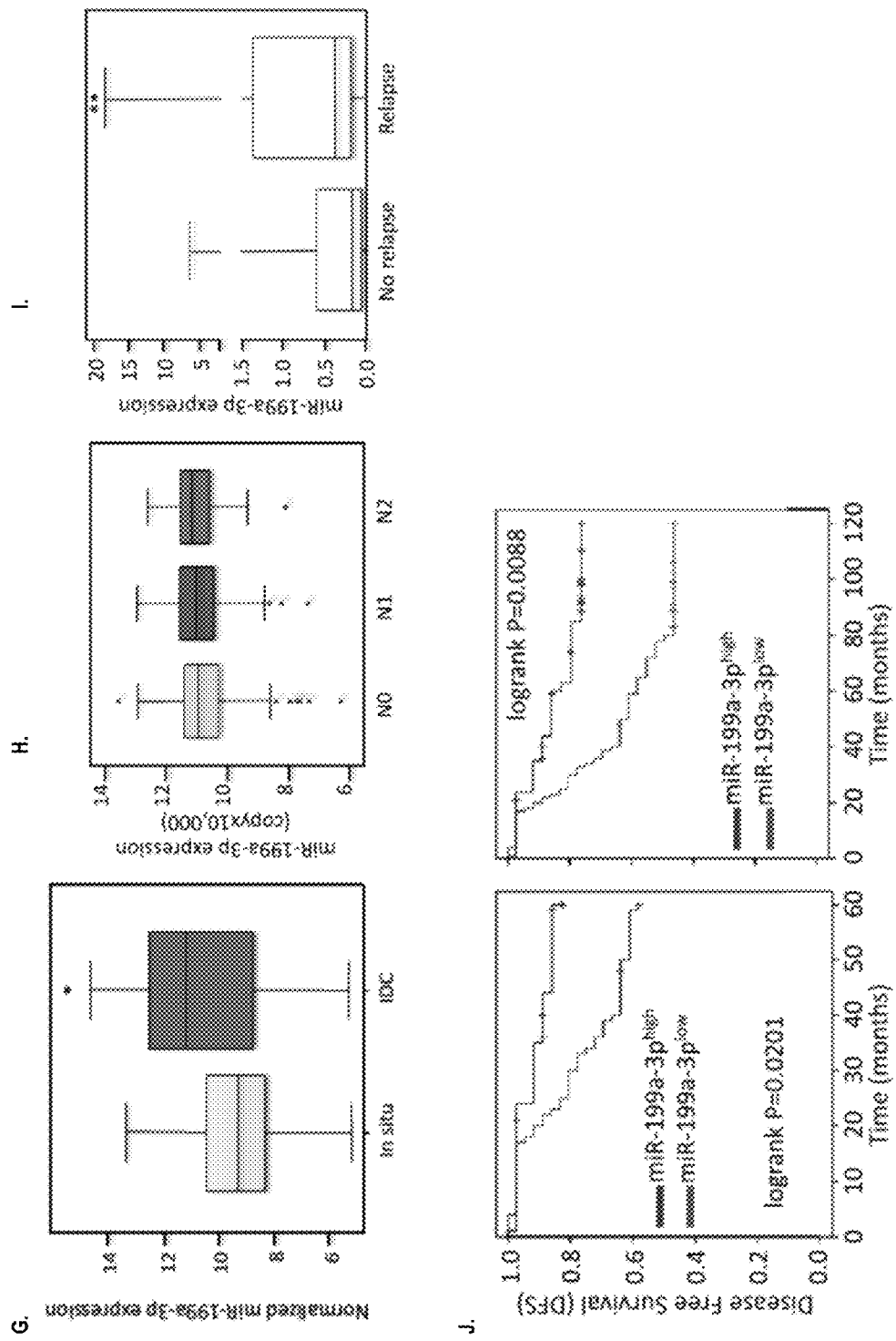

FIG. 11 shows upregulation of miR-199a and downregulation of FOXP2 in clinical breast cancer. Panel A shows SAM analysis derived from the ROCK database on A_24_P38317 in TCGA Breast expression. Normal, n=63, Primary tumor, n=66. SAM score 8.852. Panel B shows SAM analysis derived from ROCK on 235201_at in Chen and colleagues (Chen et al., Oncogene 27, 4712-4723, 2008). Breast tissue with benign lesions, n=143, Invasive ductal carcinoma (IDC), n=37. SAM score 6.316. Panel C shows FOXP2 expression profile in GSE27011. Significance was determined using unpaired student t-test. Panel D shows rtPCR-ΔΔct analyses on FOXP2 expression in normal (n=5) as compared to macrodissected breast cancer specimens derived from basal-like human breast cancers (n=12). Significance was determined using unpaired student t-test. Panel E shows FOXP2 levels (Log 2) in normal versus the indicated breast cancer subtypes in GSE20711. P values for normal (n=2) versus HER2 (n=26), Lum A (n=13), Lum B (n=22), and BLBC (n=27) were 0.0005325, 0.001527, $4.573Xe^{-6}$, and 0.03824, respectively. Significance was determined by using unpaired student's t-test. Panel F shows FOXP2 rtPCT-ΔΔct on macrodissected breast cancer specimens derived from HER2 (n=12), Lum A (n=25), Lum B (n=25), and BLBC (n=12) subgroups versus normal (n=5). Significance was determined by using unpaired student's t-test. Panel G shows miR-199a-3p expression levels in in situ tumors compared to invasive ductal samples derived from Farazi et al., Cancer Research, 71, 4443-4453, 2011. (*)-indicates P<0.05; ()-indicates P<0.01, (*)-indicates P<0.001 in 2-tailed student's t-test. Panel H shows miR-199a-3p expression in IDC patients (n=664) with or without lymph node positivity. N0 geometric mean RPM is 1780.7 (n=301), N1 geometric mean is 1951.8 (n=223), and N2 geometric mean is 2141.3 (n=82). Spearman correlation test N0<N1<N2, p=0.013. Panel I shows normalized miR-199a-3p levels (rtPCT-ΔΔct) on primary-tumor-derived RNA in relapse-free breast cancer patient (n=34) versus relapsed patient (n=40). Mann-Whitney pp=0.029 and Wilcoxon p=0.0193. Panel J shows miR-199a-3p median fold change (FC) stratified the independent population into two groups which were significantly different in their survival probability (n=73).

Figure 12:
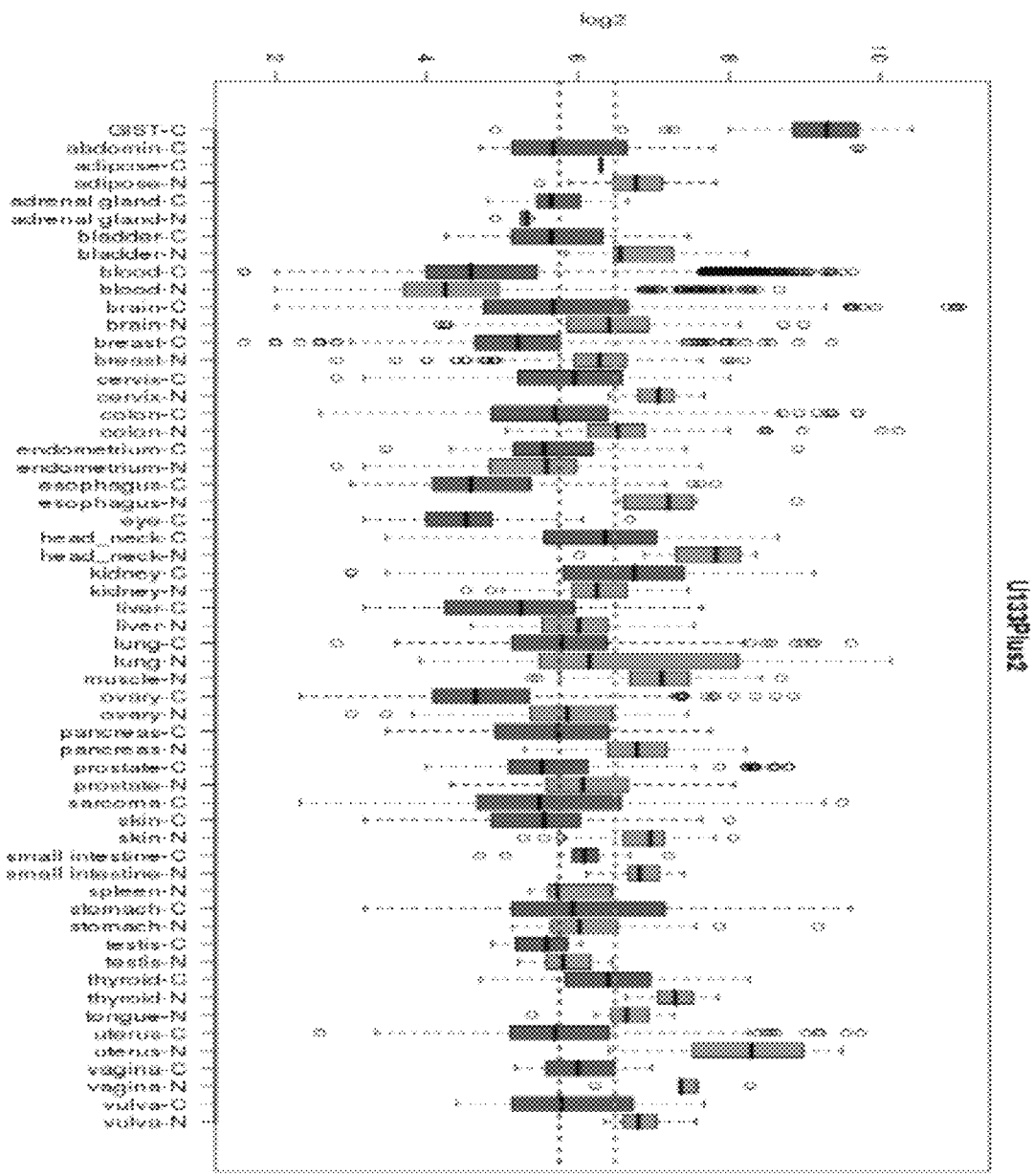

FIG. 12 shows FOXP2 expression levels in a variety of cancerous and normal tissues.

Figure 13:
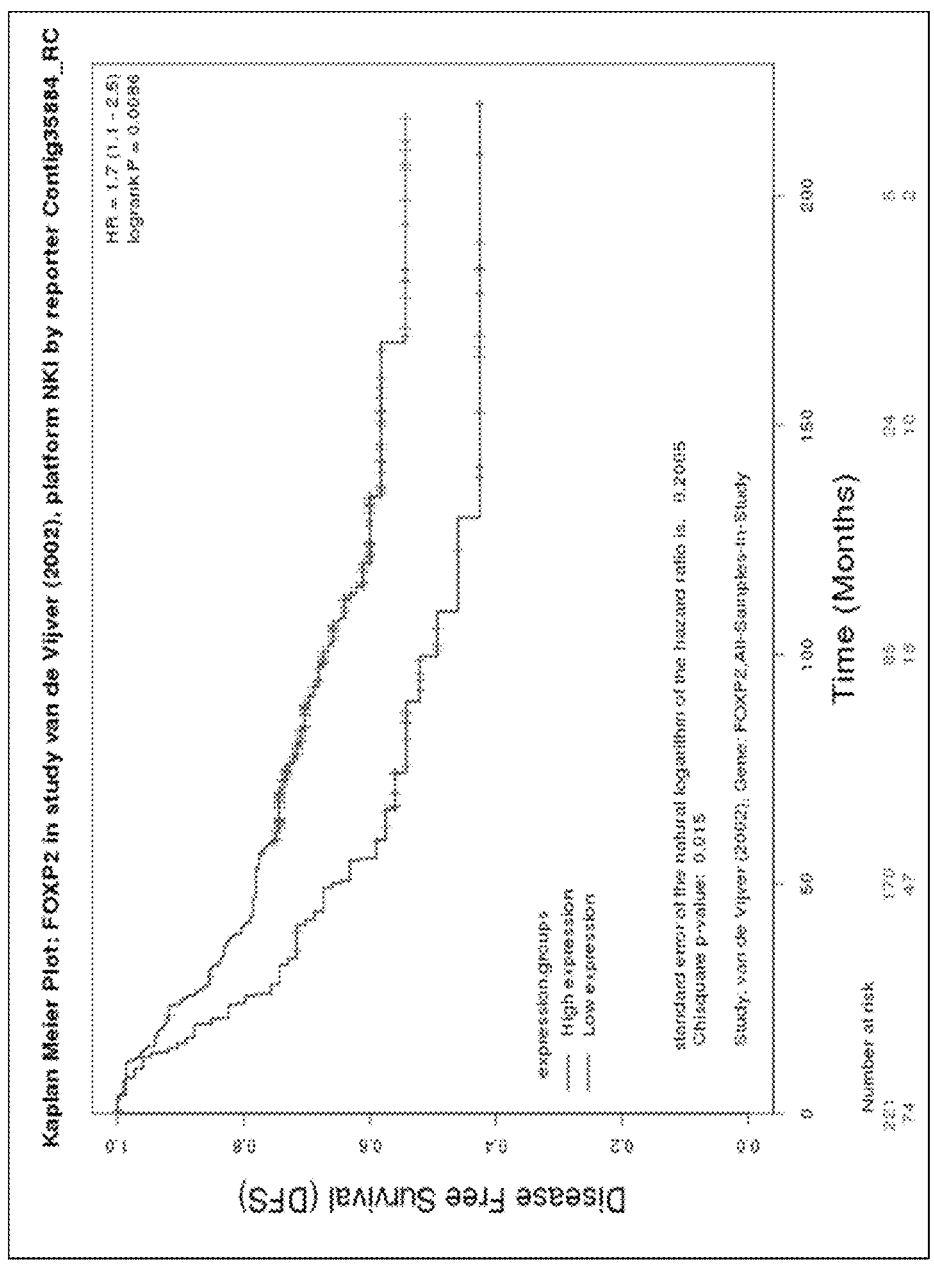
Figure 13:
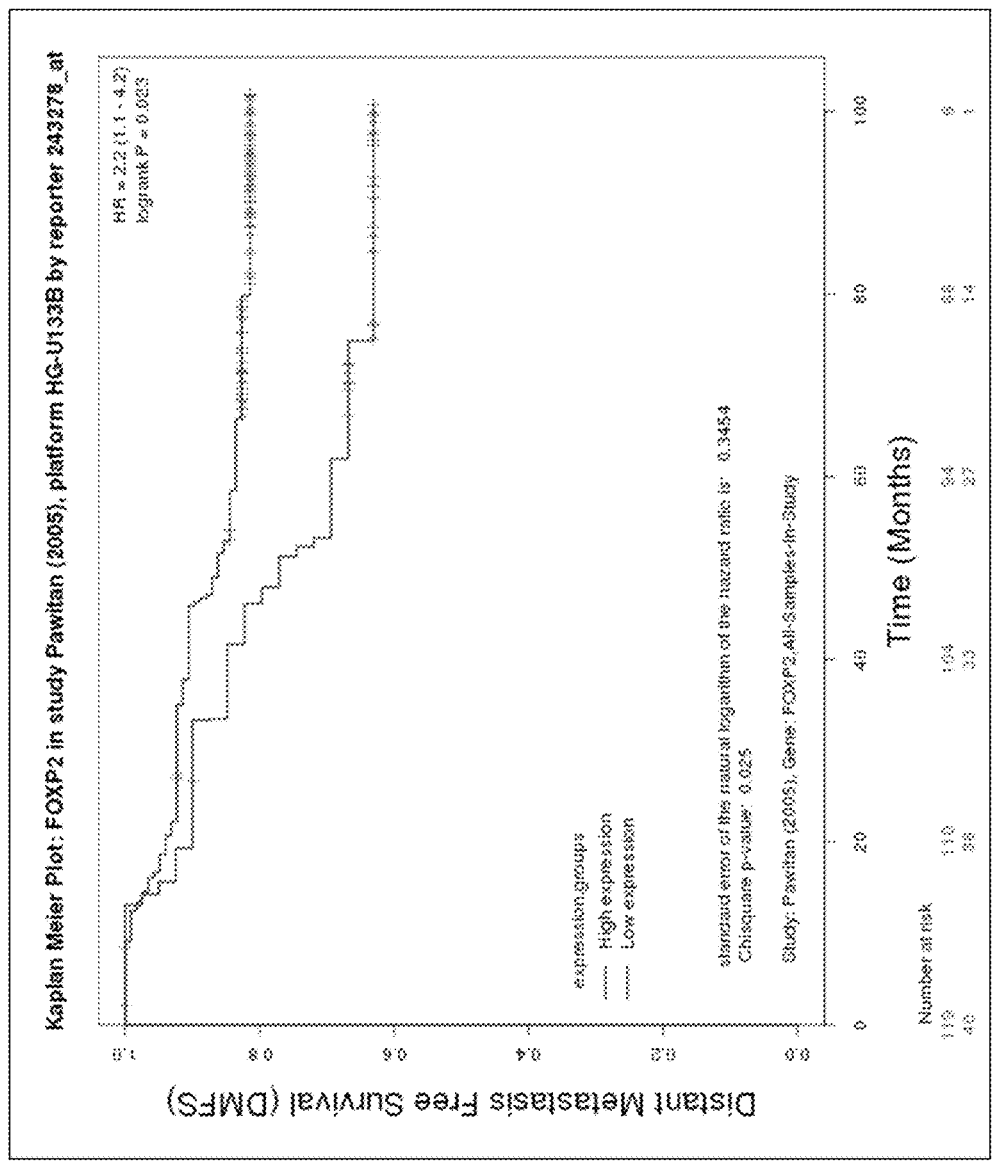
Figure 13:
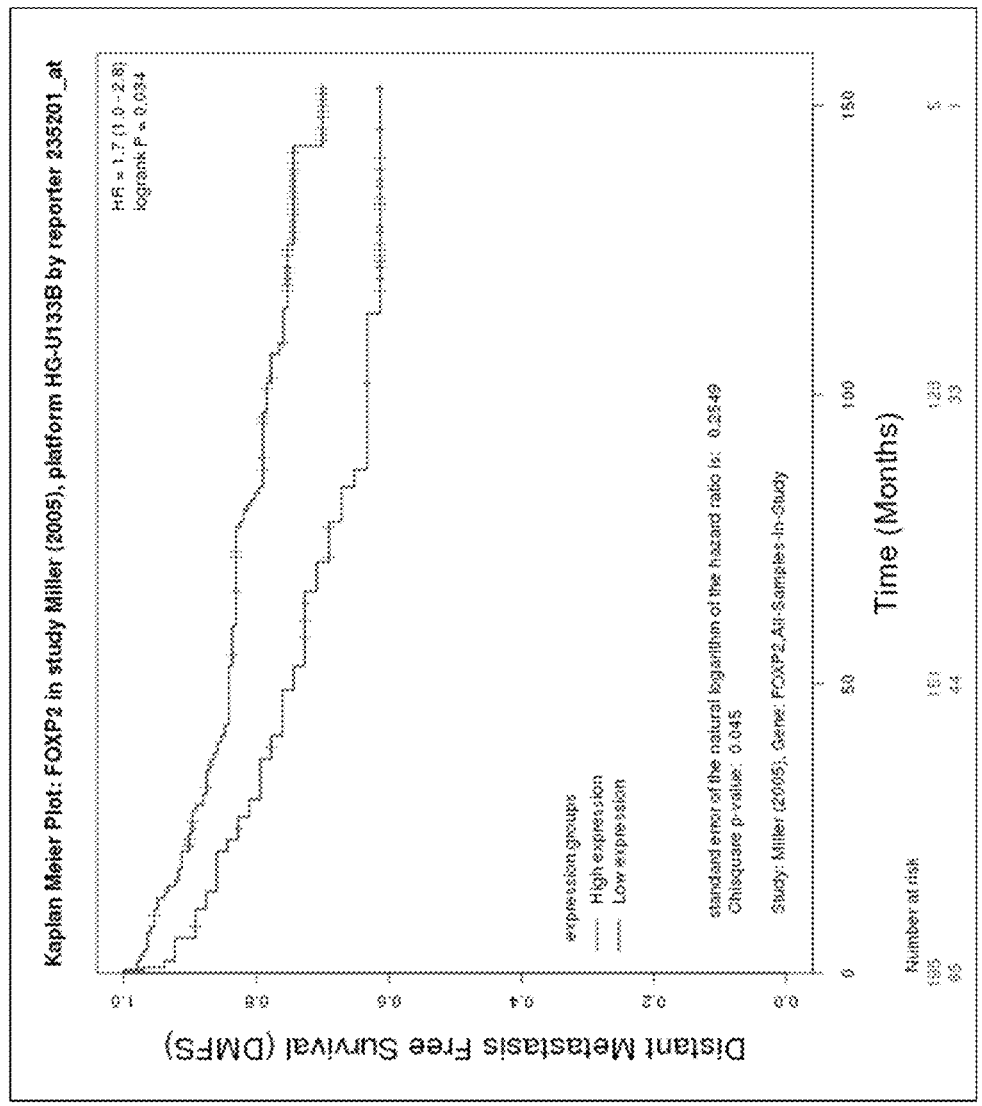
Figure 13:
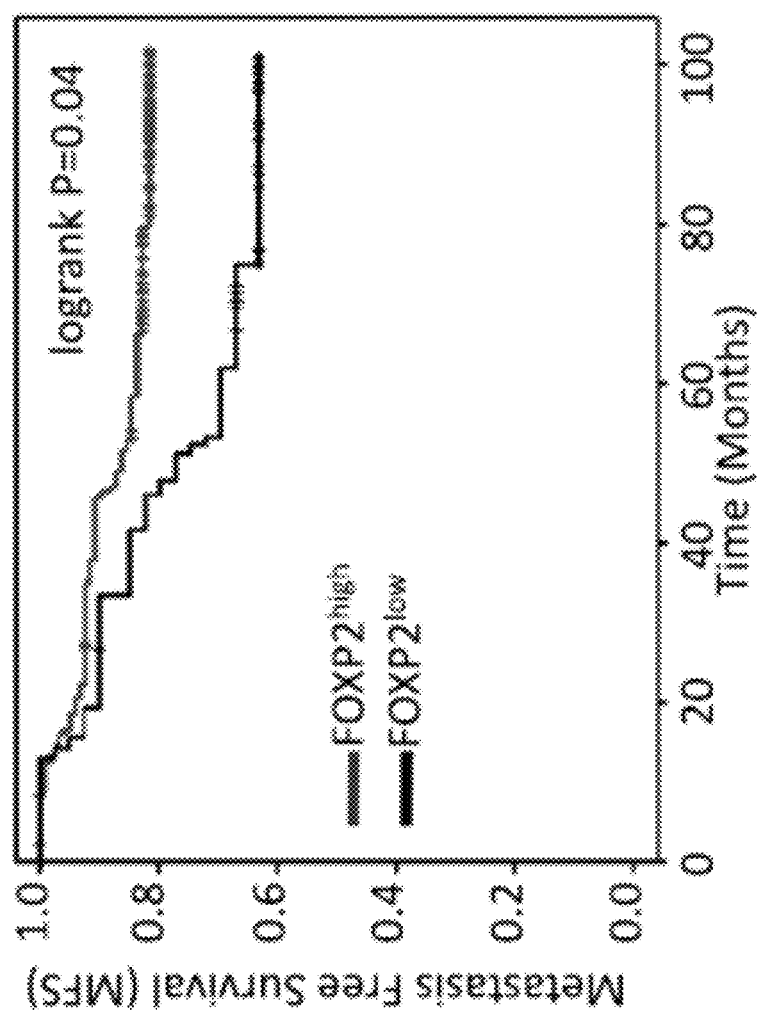

FIG. 13, panels A, B, C, and D each show Kaplan Meier plots denoting patient survival in the indicated studies. Samples were stratified based on FOXP2 expression (probe in the indicated studies, using lower-quartile of expression values of a FOXP2 probe to split selected samples). Bottom curves are low-expression samples, and top curves denotes high-expression values.

Figure 14:
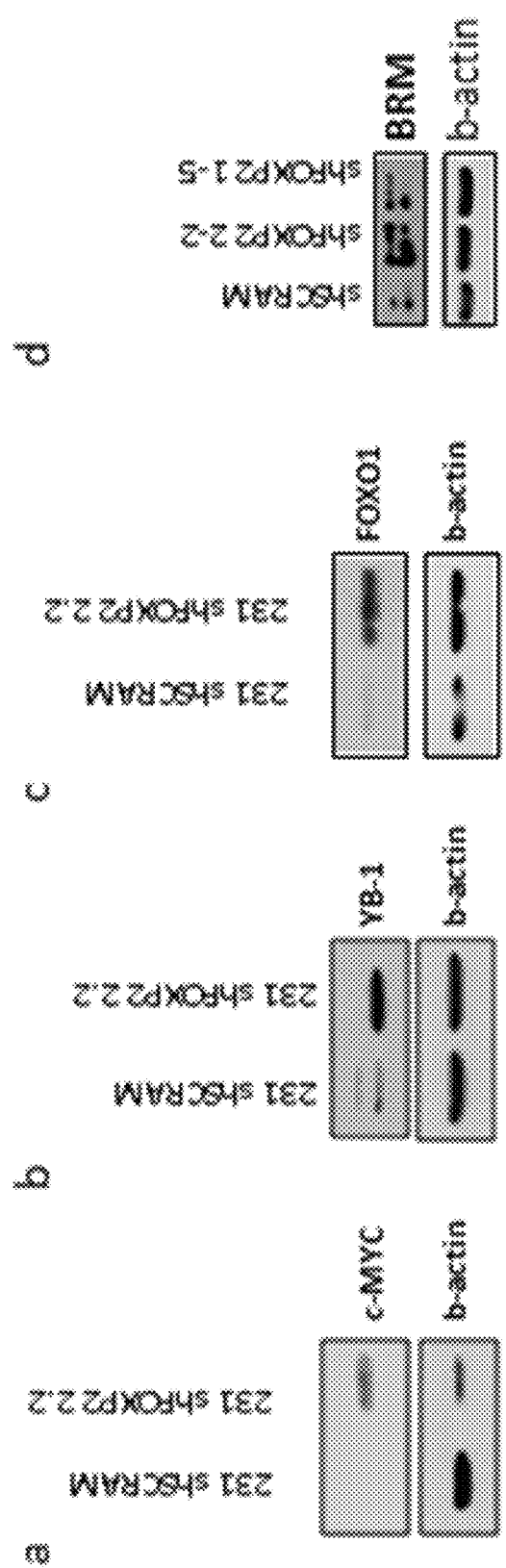
Figure 14:
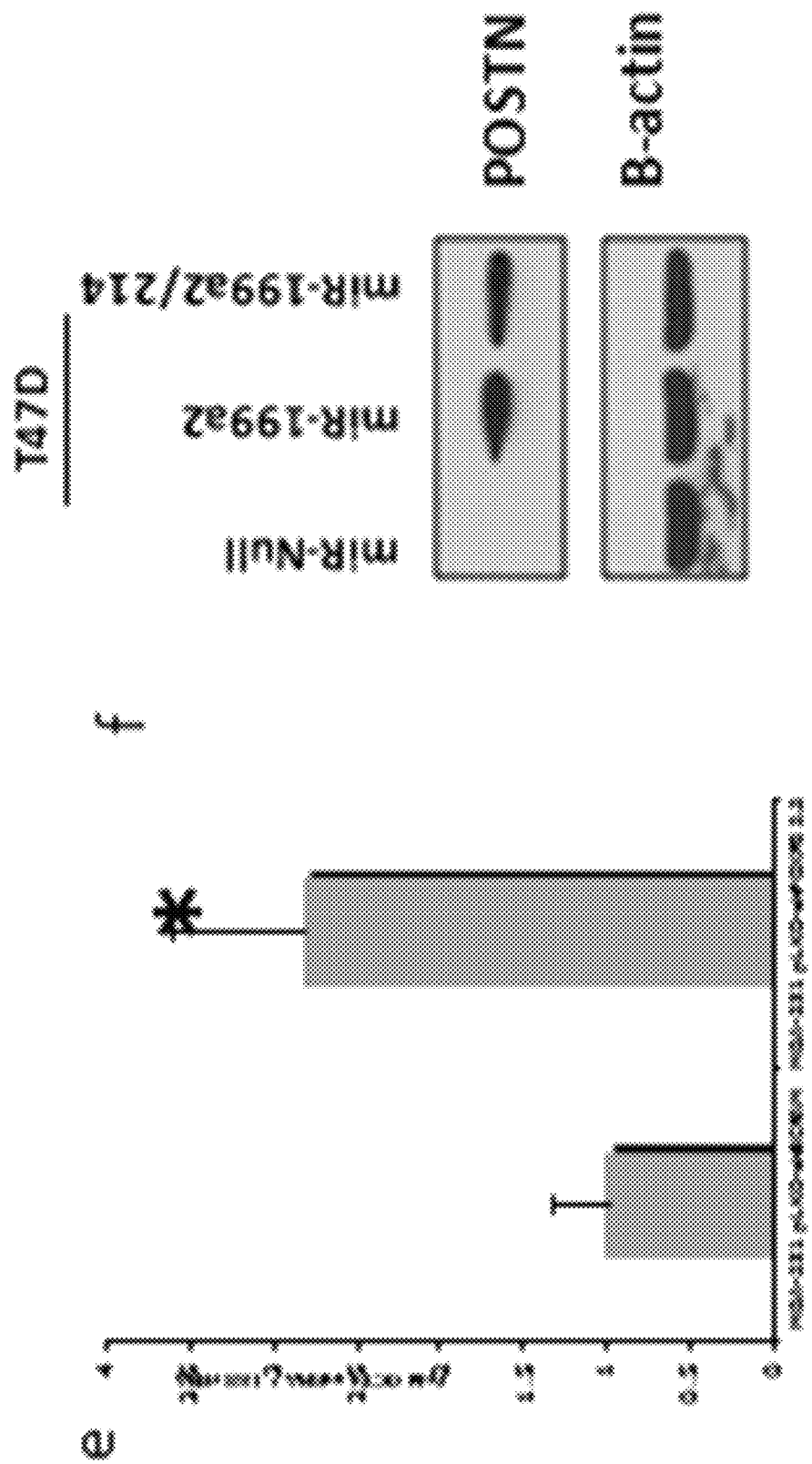

FIG. 14 shows Western blot analyses on lysates derived from MDA-MB-231 cells (Panels a-d) or T47D breast cancer cells (Panel f) expressing control (shscram) or shRNAs against FOXP2 while Panel e shows RTPCR analysis on OCT-4 in the indicated control and shFOXP2 cells.

DETAILED DESCRIPTION

The present invention is based, in part, on the discovery that FOXP2 is downregulated in the context of particularly aggressive, including metastatic, forms of cancer and that this downregulation is mediated by miRs, including miR-199a, miR-214, miR-34a, miR-762, miR-1915, and Let-7b. In some aspects, the present invention provides for methods and compositions for treating aggressive cancers with polynucleotide agents.

In one aspect, a method for treating or preventing an aggressive cancer, comprising administering a micro-RNA inhibitor, by way of non-limiting example, an optionally modified antisense oligonucleotide, of one or more of miR-199a, miR-214, miR-34a, miR-762, miR-1915, and Let-7b to a subject in need thereof is provided. Also provided are uses of a micro-RNA inhibitor, by way of non-limiting example, an optionally modified antisense oligonucleotide, of one or more of miR-199a, miR-214, miR-34a, miR-762, miR-1915, and Let-7b, in the treatment of and/or the manufacture of a medicament for the treatment of an aggressive cancer.

In some aspects, the present invention provides for methods for treating or preventing an aggressive cancer, comprising administering a micro-RNA inhibitor of one or more of miR-199a, miR-214, miR-34a, miR-762, miR-1915, and Let-7b to a subject in need thereof, wherein the cancer is characterized by having reduced levels or activity of forkhead box protein P2 (FOXP2), relative to a non-cancerous, or a benign state, or less aggressive cancerous state (by way of non-limiting example, the cancer is metastatic and is characterized by having reduced levels or activity of FOXP2 relative to a non-metastatic cancer and/or a benign state). Also provided are uses of a micro-RNA inhibitor, by way of non-limiting example, an optionally modified antisense oligonucleotide, of one or more of miR-199a, miR-214, miR-34a, miR-762, miR-1915, and Let-7b, in the treatment of and/or the manufacture of a medicament for the treatment of an aggressive cancer which is characterized by having reduced levels or activity of forkhead box protein P2 (FOXP2).

In some aspects, the present invention provides for methods for treating or preventing an aggressive cancer, comprising administering an antisense oligonucleotide to one or more of miR-199a, miR-214, miR-34a, miR-762, miR-1915, and Let-7b to a subject in need thereof. Also provided are uses of an antisense oligonucleotide to one or more of miR-199a, miR-214, miR-34a, miR-762, miR-1915, and Let-7b in the treatment of and/or the manufacture of a medicament for the treatment of an aggressive cancer.

FOXP2 is a member of the forkhead family of transcription factors. It has been described to act as a transcriptional repressor, primarily in the context of neural development and function. Its functions have been shown to be essential for developmental neurogenesis, neuronal plasticity, and for the capacity for human speech. FOXP2 has likewise been shown to serve an essential role in the development and differentiation of non-neuronal tissues, such as lung and esophagus. However, the role of FOXP2, including its deregulation, in cancer pathogenesis, including progression to aggressive forms, was largely unknown until the present disclosure.

Accordingly, in various embodiments, the present invention provides for methods and uses that target FOXP2 in the treatment of cancer, including aggressive cancer types. In various embodiments, the present methods are applicable to other related members of the forkhead family of transcription factors, including, by way of non-limiting example, FOXA1, FOXA2, FOXA3, FOXB1, FOXB2, FOXC1, FOXC2, FOXD1, FOXD2, FOXD3, FOXD4, FOXD5, FOXD6, FOXE1, FOXE2, FOXE3, FOXF1, FOXF2, FOXG1, FOXH1, FOXI1, FOXI2, FOXJ1, FOXJ2, FOXJ3, FOXK1, FOXK2, FOXL1, FOXL2, FOXM1, FOXN1, FOXN2, FOXN3, FOXN4, FOXO1, FOXO3, FOXO4, FOXO6, FOXP1, FOXP3, FOXP4, FOXQ1, FOXR1, and FOXR2.

Furthermore, the role of certain specific miRNAs, by way of non-limiting example, miR-199a, miR-214, miR-34a, miR-762, miR-1915, and Let-7b, in causing a deregulation of FOXP2 and leading to cancer aggressiveness has not been appreciated in the art.

In various embodiments, the present invention provides for methods and uses of micro-RNA inhibitors, including to miR-199a, miR-214, miR-34a, miR-762, miR-1915, and Let-7b. MicroRNAs (miRNA or miR) are nucleic acid molecules that are able to regulate the expression of target genes. See review by Carrington et al. *Science*, Vol. 301 (5631):336-338, 2003). MiRNAs are typically short (usually 18-24 nucleotides) and act as repressors of target mRNAs by promoting their degradation, when their sequences are perfectly complementary, and/or by inhibiting translation, when their sequences contain mismatches. Without being bound by theory, mature miRNAs are believed to be generated by RNA polymerase II (pol II) or RNA polymerase III (pol III; see Qi et al. (2006) *Cellular & Molecular Immunology*, Vol. 3:411-419) and arise from initial transcripts termed primary miRNA transcripts (pri-miRNAs). These pri-miRNAs are frequently several thousand bases long and are therefore processed to make the much shorter mature miRNAs. This processing is believed to occur in two steps. First, pri-miRNAs are processed in the nucleus by the RNase Drosha into about 70- to about 100-nucleotide hairpin-shaped precursors (pre-miRNAs). Second, after transposition to the cytoplasm, the hairpin pre-miRNAs are further processed by the RNase Dicer to produce a double-stranded miRNA. A mature miRNA strand is then incorporated into the RNA-induced silencing complex (RISC), where it associates with its target mRNA by base-pair complementarity and leads to suppression of protein expression.

In some embodiments, various microRNAs reduce the level of a FOX family member, including FOXP2, and lead to the formation of an aggressive cancer. In some embodiments, an agent that inhibits various miRs is used to treat cancer by, for example, preventing the reduction of FOXP2. In still other embodiments, the miRs that are targeted are one or more of miR-199a, miR-214, miR-34a, miR-762, miR-1915, and Let-7b. In further embodiments, the expression and/or activity of one or more of miR-199a, miR-214, miR-34a, miR-762, miR-1915, and Let-7b is reduced in the subject following administration of the micro-RNA inhibitor. In some embodiments, the inhibitor of one or more of miR-199a, miR-214, miR-34a, miR-762, miR-1915, and Let-7b prevents or diminishes a downregulation of FOXP2.

Antisense oligonucleotides can include ribonucleotides or deoxyribonucleotides or a combination thereof. Antisense oligonucleotides may have at least one chemical modification (non-limiting examples are sugar or backbone modifications). In some embodiments, the chemical modification is one or more of a phosphorothioate, 2'-O-Methyl, or 2'-O-Methoxyethyl, 2'-O-alkyl-RNA unit, 2'-OMe-RNA unit, 2'-amino-DNA unit, 2'-fluoro-DNA unit (including, but not limited to, a DNA analogue with a substitution to a fluorine at the 2' position (2' F)), LNA unit, PNA unit, HNA unit, INA unit, and a 2' MOE RNA unit.

Suitable antisense oligonucleotides can be comprised of one or more conformationally constrained or bicyclic sugar nucleoside modifications (BSN) that confer enhanced thermal stability to complexes formed between the oligonucleotide containing BSN and their complementary miRNA target strand. For example, in one embodiment, the antisense oligonucleotides contain at least one locked nucleic acid. Locked nucleic acids (LNAs) contain a 2'-O, 4'-C-methylene ribonucleoside (structure A) wherein the ribose sugar moiety is in a locked conformation. In another embodiment, the antisense oligonucleotides contain at least one 2', 4'-C-bridged 2' deoxyribonucleoside (CDNA, structure B). See, e.g., U.S. Pat. No. 6,403,566 and Wang et al. (1999) *Bioorganic and Medicinal Chemistry Letters*, Vol. 9: 1147-1150, both of which are herein incorporated by reference in their entireties. In yet another embodiment, the antisense oligonucleotides contain at least one modified nucleoside having the structure shown in structure C. The antisense oligonucleotides targeting miRNAs that regulate tumor suppressors can contain combinations of BSN (LNA, CDNA, and the like) or other modified nucleotides, and ribonucleotides or deoxyribonucleotides.

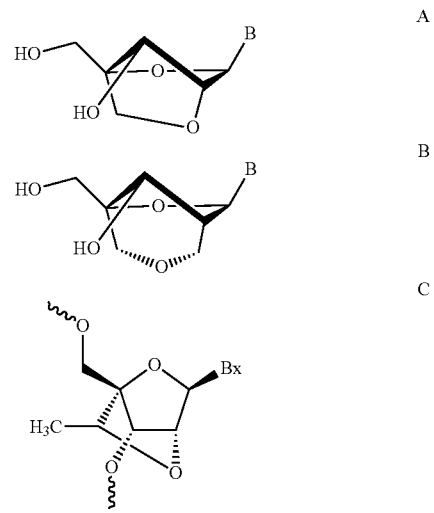

A

B

C

Alternatively, the antisense oligonucleotides can comprise peptide nucleic acids (PNAs), which contain a peptide-based backbone rather than a sugar-phosphate backbone.

Other modified sugar or phosphodiester modifications to the antisense oligonucleotide are also contemplated. By way of non-limiting examples, other chemical modifications can include 2'-O-alkyl (e.g., 2'-O-methyl, 2'-O-methoxyethyl), 2'-fluoro, and 4'-thio modifications, and backbone modifications, such as one or more phosphorothioate, morpholino, or phosphonocarboxylate linkages (see, e.g., U.S. Pat. Nos. 6,693,187 and 7,067,641, which are herein incorporated by reference in their entireties). In one embodiment, antisense oligonucleotides targeting oncogenic miRNAs contain 2'-O-methyl sugar modifications on each base and are linked by phosphorothioate linkages. Antisense oligonucleotides, particularly those of shorter lengths (e.g., less than about 16 nucleotides, about 7-8 nucleotides) can comprise one or more affinity enhancing modifications, such as, but not limited to, LNAs, bicyclic nucleosides, phosphonoformates, 2' O-alkyl modifications, and the like. In some embodiments, suitable antisense oligonucleotides are 2'-O-methoxyethyl gapmers which contain 2'-O-methoxyethyl-modified ribonucleotides on both 5' and 3' ends with at least ten deoxyribonucleotides in the center. These gapmers are capable of triggering RNase H-dependent degradation mechanisms of RNA targets. Other modifications of antisense oligonucleotides to enhance stability and improve efficacy, such as those described in U.S. Pat. No. 6,838,283, which is herein incorporated by reference in its entirety, are known in the art and are suitable for use in the methods of the invention. For instance, and not intending to be limiting, to facilitate in vivo delivery and stability, the antisense oligonucleotide can be linked to a steroid, such as cholesterol moiety, a vitamin, a fatty acid, a carbohydrate or glycoside, a peptide, or other small molecule ligand at its 3' end.

In some embodiments, antisense oligonucleotides useful for inhibiting the activity of miRNAs, including, for example, one or more of miR-199a, miR-214, miR-34a, miR-762, miR-1915, and Let-7b, are about 5 to about 25 nucleotides in length, about 10 to about 30 nucleotides in length, or about 20 to about 25 nucleotides in length. In certain embodiments, antisense oligonucleotides targeting oncogenic miRNAs are about 8 to about 18 nucleotides in length, in other embodiments about 12 to about 16 nucleotides in length, and in other embodiments about 7 to about 8 nucleotides in length. Any 7-mer or longer complementary to an oncogenic miRNA may be used, i.e., any anti-miR complementary to the 5' end of the miRNA and progressing across the full complementary sequence of the miRNA. By way of non-limiting example, the antisense oligonucleotides targeting oncogenic miRNAs, including, for example, one or more of miR-199a, miR-214, miR-34a, miR-762, miR-1915, and Let-7b, are about 4, or about 5, or about 6, or about 7, or about 8, or about 9, or about 10, or about 11, or about 12, or about 13, or about 14, or about 15, or about 16, or about 17, or about 18, or about 19, or about 20, or about 21, or about 22, or about 23, or about 24, or about 25, or about 26, or about 27, or about 28, or about 29, or about 30 nucleotides in length.

In some embodiments, an inhibitor of miRNA is an antisense oligonucleotide. In some embodiments, the antisense oligonucleotide comprising a sequence that is at least partially complementary to a mature sequence of one or more of miR-199a, miR-214, miR-34a, miR-762, miR-1915, and Let-7b. For example, the antisense oligonucleotide may be at least partially complementary to a mature sequence of miR-199a, or the antisense oligonucleotide may be at least partially complementary to a mature sequence of miR-214, or the antisense oligonucleotide may be at least partially complementary to a mature sequence of miR-34a, or the antisense oligonucleotide may be at least partially complementary to a mature sequence of miR-762, or the antisense oligonucleotide may be at least partially complementary to a mature sequence of miR-1915, or the antisense oligonucleotide may be at least partially complementary to a mature sequence of Let-7. In other embodiments, the antisense oligonucleotide may be at least partially complementary to a mature sequence of to several of miR-199a, miR-214, miR-34a, miR-762, miR-1915, and Let-7, based on homology between these target miRs. In some embodiments, the sequence of the inhibitor is taken, in part, from the sequence of a human transcript.

Antisense oligonucleotides can comprise a sequence that is at least partially complementary to a mature or minor (i.e. star) oncogenic miRNA sequence, e.g., at least about 75%, 80%, 85%, 90%, 95%, 96%, 97%, 98%, or 99% complementary to a mature or minor (i.e. star) oncogenic miRNA sequence. In some embodiments, the antisense oligonucleotide can be substantially complementary to a mature or minor oncogenic miRNA sequence, that is at least about 90%, 95%, 96%, 97%, 98%, or 99% complementary to a target polynucleotide sequence. In one embodiment, the antisense oligonucleotide comprises a sequence that is 100% complementary to a mature or minor oncogenic miRNA sequence.

As used herein, substantially complementary refers to a sequence that is at least about 95%, 96%, 97%, 98%, 99%, or 100% complementary to a target polynucleotide sequence (non-limiting examples are mature, minor, precursor miRNA, or pri-miRNA sequence of, for example, one or more of miR-199a, miR-214, miR-34a, miR-762, miR-1915, and Let-7b).

In some embodiments, the antisense oligonucleotides are antagomirs. Antagomirs are single-stranded, chemically-modified ribonucleotides that are at least partially complementary to miRNAs and therefore may silence them. See, e.g., Krützfeldt, et al. Nature (2005) 438 (7068): 685-9. Antagomirs may comprise one or more modified nucleotides, such as 2'-O-methyl-sugar modifications. In some embodiments, antagomirs comprise only modified nucleotides. Antagomirs can also comprise one or more phosphorothioate linkages resulting in a partial or full phosphorothioate backbone. To facilitate in vivo delivery and stability, the antagomir can be linked to a cholesterol or other moiety at its 3' end. Antagomirs suitable for inhibiting can be about 15 to about 50 nucleotides in length, about 18 to about 30 nucleotides in length, and about 20 to about 25 nucleotides in length. The antagomirs can be at least about 75%, 80%, 85%, 90%, 95%, 96%, 97%, 98%, or 99% complementary to a mature or minor oncogenic miRNA sequence. In some embodiments, the antagomir may be substantially complementary to a mature or minor oncogenic miRNA sequence, that is at least about 95%, 96%, 97%, 98%, or 99% complementary to a target polynucleotide sequence. In other embodiments, the antagomirs are 100% complementary to a mature or minor oncogenic miRNA sequence.

Antisense oligonucleotides or antagomirs may comprise a sequence that is substantially complementary to a precursor miRNA sequence (pre-miRNA) or primary miRNA sequence (pri-miRNA) of an oncogenic miRNA. In some embodiments, the antisense oligonucleotide comprises a sequence that is located outside the 3'-untranslated region of a target of that miRNA. In some embodiments, the antisense oligonucleotide comprises a sequence that is located inside the 3'-untranslated region of a target of that miRNA.

Any of the inhibitors of the oncogenic miRNAs described herein, including but not limited to one or more of miR-199a, miR-214, miR-34a, miR-762, miR-1915, and Let-7b, can be delivered to a target cell (a non-limiting example is a cancer cell) by delivering to the cell an expression vector encoding the miRNA inhibitors or agonists. A vector is a composition of matter which can be used to deliver a nucleic acid of interest to the interior of a cell. Numerous vectors are known in the art, including, but not limited to, linear polynucleotides, polynucleotides associated with ionic or amphiphilic compounds, plasmids, and viruses. Thus, the term vector includes an autonomously replicating plasmid or a virus. Examples of viral vectors include, but are not limited to, adenoviral vectors, adeno-associated virus vectors, retroviral vectors, and the like. An expression construct can be replicated in a living cell, or it can be made synthetically. For purposes of this application, the terms expression construct, expression vector, and vector are used interchangeably to demonstrate the application of the invention in a general, illustrative sense, and are not intended to limit the invention.

In one embodiment, an expression vector for expressing an inhibitor of an oncogenic miRNA, e.g. one or more of miR-199a, miR-214, miR-34a, miR-762, miR-1915, and Let-7b, comprises a promoter operably linked to a polynucleotide encoding an antisense oligonucleotide. The sequence of the expressed antisense oligonucleotide may be partially or perfectly complementary to a mature or minor sequence of an oncogenic miRNA. The phrase operably linked or under transcriptional control as used herein means that the promoter is in the correct location and orientation in relation to a polynucleotide to control the initiation of transcription by RNA polymerase and expression of the polynucleotide.

As used herein, a promoter refers to a DNA sequence recognized by the synthetic machinery of the cell, or introduced synthetic machinery, required to initiate the specific transcription of a gene. Suitable promoters include, but are not limited to, RNA pol I, pol II, pol III, and viral promoters (e.g., human cytomegalovirus (CMV) immediate early gene promoter, the SV40 early promoter, and the Rous sarcoma virus long terminal repeat).

In certain embodiments, the promoter operably linked to a polynucleotide encoding an miRNA inhibitor or a polynucleotide encoding a tumor-suppressor regulating miRNA and/or miRNA targeting genes of markers linked to cancer etiologies can be an inducible promoter. Inducible promoters are known in the art and include, but are not limited to, the tetracycline promoter, the metallothionein IIA promoter, the heat shock promoter, the steroid/thyroid hormone/retinoic acid response elements, the adenovirus late promoter, and the inducible mouse mammary tumor virus LTR.

Methods of delivering expression constructs and nucleic acids to cells are known in the art and can include, by way of non-limiting example, calcium phosphate co-precipitation, electroporation, microinjection, DEAE-dextran, lipofection, transfection employing polyamine transfection reagents, cell sonication, gene bombardment using high velocity microprojectiles, and receptor-mediated transfection.

The present invention also includes scavenging or clearing inhibitors of oncogenic miRNAs following treatment. Scavengers may include isolated nucleic acids that are complementary to miRNA inhibitors or vectors expressing the same. Therefore, they may bind to miRNA inhibitors or vectors expressing the same and, in doing so, prevent the binding between miRNA and target. The method may comprise overexpressing binding sites for the tumor suppressive inhibitors in a tissue.

In some embodiments, the present invention provides for methods and uses for the treatment of various cancer types, including particularly aggressive cancer types, subtypes or stages.

In some embodiments, aggressiveness of a tumor is determined by using one or more of three measurements from a pathology report: cell differentiation, mitotic activity, and cell nuclei abnormality. Information about these measurements usually is provided through three scales that are totaled to give a score that ranges from three to nine. In the cell differentiation assessment, "normal" cell differentiation means that the cells are able to normally form the glands that make up the tissue. When cells form tissue that looks less like normal tissue glands, they are called less differentiated. This usually is a sign of a more aggressive cancer. Scores generally range from one to three, with higher scores indicating less differentiation. In the mitotic activity assessment, a measurement of the speed at which tumor cells are dividing is undertaken. Aggressive tumors have a large numbers of mitotic cells. Scores range from one to three, with higher scores indicating more aggressive activity. In the cell nuclei abnormality assessment, the nuclei of the cells are graded based on how similar in size they appear. Scores range from one to three, with higher scores indicating higher levels of lumpy, differently sized nuclei. Often these three assessments are taken as a sum to scale aggressiveness: a score of three to five out of nine is called grade one, and tends to indicate a less aggressive cancer; a score of six to seven is grade two, and a score of eight to nine is grade three, and tends to indicate a more aggressive cancer. In some embodiments, the present therapeutic methods are directed at grade two or grade three cancers.

In some embodiments, other measurements known in the art may be used to assess aggressiveness of a cancer. By way of non-limiting example, cancer aggressiveness is characterizable by one or more of a high tumor grade and/or stage, low overall survival, high probability of metastasis, and the presence of a tumor marker indicative of aggressiveness.

Tumor grade is a system used to classify cancer cells in terms of how abnormal they look under a microscope and how quickly the tumor is likely to grow and spread. Many factors are considered when determining tumor grade, including the structure and growth pattern of the cells. The specific factors used to determine tumor grade may vary with each type of cancer and are known in the art.

Histologic grade, also called differentiation, refers to how much the tumor cells resemble normal cells of the same tissue type. Nuclear grade refers to the size and shape of the nucleus in tumor cells and the percentage of tumor cells that are dividing.

Based on the microscopic appearance of cancer cells, pathologists commonly describe tumor grade by four degrees of severity: Grades 1, 2, 3, and 4. The cells of Grade 1 tumors resemble normal cells, and tend to grow and multiply slowly. Grade 1 tumors are generally considered the least aggressive in behavior. Conversely, the cells of Grade 3 or Grade 4 tumors do not look like normal cells of the same type. Grade 3 and 4 tumors tend to grow rapidly and spread faster than tumors with a lower grade. The American Joint Committee on Cancer recommends the following guidelines for grading tumors: GX-grade cannot be assessed (Undetermined grade); G1-well-differentiated (Low grade); G2-moderately differentiated (Intermediate grade); G3-poorly differentiated (High grade); and G4-undifferentiated (High grade).

Grading systems are different for each type of cancer. For example, pathologists use the Gleason system to describe the degree of differentiation of prostate cancer cells. The Gleason system uses scores ranging from Grade 2 to Grade 10. Lower Gleason scores describe well-differentiated, less aggressive tumors. Higher scores describe poorly differentiated, more aggressive tumors. Other grading systems include, for example, the Bloom-Richardson system for breast cancer and the Fuhrman system for kidney cancer.

In some embodiments, the present invention finds use in cancers that grade in a manner consistent with aggressiveness. For example, in various embodiments, tumor grade is used to score a cancer in the assessment of aggressiveness and direct treatment with any agent described herein to target, for example, FOXP2. By way of further example, a high tumor grade may direct treatment of a patient with one or more of the micro-RNA inhibitors (including antisense) of one or more of miR-199a, miR-214, miR-34a, miR-762, miR-1915, and Let-7b as described herein. In a specific embodiment, a breast cancer patient may have a high tumor score according to, for example, the Bloom-Richardson system and/or Elston Grade (e.g. grade 2 or grade 3 tumors or tumors having scores of about 6, or about 7, or about 8, or about 9). Such a patient is treated with one or more of the micro-RNA inhibitors (including antisense) of one or more of miR-199a, miR-214, miR-34a, miR-762, miR-1915, and Let-7b. Alternatively, as further described herein, such grading can be paired with detection of levels of FOXP2 and one or more of miR-199a, miR-214, miR-34a, miR-762, miR-1915, and Let-7b in the determination of cancer aggressiveness.

Staging the breast cancer is critical to determining how aggressively to treat a cancer. To stage a cancer, the physicians look at the size of the tumor, check for the presence of cancer cells in lymph nodes, and determine whether or not there is evidence of metastasis. Smaller tumors usually require less aggressive treatment. The tumor may be measured by "hand" by the doctor or measured by the pathologist after surgery. Mammograms, ultrasound, and MRI (magnetic resonance imaging) also may give an indication of the size of a tumor. The most accurate measurements are made after surgery. A tumor that is smaller than two centimeters (cm) is labeled T-1, a tumor that is between two and five cm is T-2, and a tumor that is larger than five cm is T-3. A T-4 tumor is one that is stuck to the skin or chest wall. In some embodiments, the present methods are directed to treating as T-3 and/or T-4 tumor.

With regard to lymph node evaluation, a pathologist may test lymph nodes near the tumor to detect tumors cells that may slough from a primary site. The number of lymph nodes that have cancerous cells will affect which treatment is used. A score of N-0 means that there is no cancer in any lymph nodes, a score of N-1 means that there is cancer in one to three lymph nodes, a score of N-2 means that there is cancer in four to nine nodes, and a score of N-3 means that there is cancer in ten or more nodes. In various embodiments, scores of N-3 and/or N-4 indicate an aggressive tumor and are encompassed by the present therapeutic methods.

Further, a bone scan, CAT (computed axial tomography) scan, or PET (positron emission tomography) scan can be used to determine if the cancer has metastasized to other organs of the body. If there is no evidence of spread, the score is M-0; if there is, the score is M-1. In various embodiments, M-1 tumors are treated by the present invention.

Further, overall staging is useful in determining cancer aggressiveness. Stage 1 tumors are not likely to have spread and may be more easily treated with, for example, resection. Stage 4 tumors have metastasized and are not able to be cured, although they still can be treated. In various embodiments, the present invention may treat a higher stage tumor (e.g. 2, 3, or 4).

Cancer survival rates or survival statistics may refer to the percentage of people who survive a certain type of cancer for a specific amount of time. Cancer statistics often use an overall five-year survival rate. For example the overall five-year survival rate for bladder cancer is 80 percent, i.e. 80 of every 100 of people diagnosed with bladder cancer were living five years after diagnosis and 20 out of every 100 died within five years of a bladder cancer diagnosis. Other types of survival rates may be used, for example: disease-free survival rate (number of people with cancer who achieve remission) and progression-free survival rate. (number of people who still have cancer, but their disease is not progressing). In some embodiments, an aggressive cancer of the present invention is one that is characterized by a lower overall survival probability. For instance, in some embodiments, cancers with low survival rates are considered aggressive and direct treatment with one or more polynucleotide agents described herein.

Probability of metastasis refers to the likelihood that a cancer will take on metastatic properties. Metastasis refers to the spread of cancer from its primary site to other places in the body. Cancer cells can break away from a primary tumor, penetrate into lymphatic and blood vessels, circulate through the bloodstream, and grow in a distant focus (metastasize) in normal tissues elsewhere in the body. Metastasis can be local or distant. Metastasis is a sequential process, contingent on tumor cells breaking off from the primary tumor, traveling through the bloodstream, and stopping at a distant site. At the new site, the cells establish a blood supply and can grow to form a life-threatening mass. Both stimulatory and inhibitory molecular pathways within the tumor cell regulate this behavior, and interactions between the tumor cell and host cells in the distant site are also significant.

In some embodiments, cancers which are scored in this manner are considered aggressive and are candidates for the treatments described herein.

Cancer cell markers refer to properties of cancer, including the expression of certain genes/proteins that are indicative of cancer. These markers are known in the art. In some embodiments, certain cancer cell markers are indicative of aggressive cancers, while others are not. For example, in breast cancer: basal, triple negative, ER negative, and Her2 positive are indicative of aggressive cancers. Conversely, luminal, hormone receptor positive, ER positive and Her2 negative are indicative of less aggressive cancers. For non-small cell lung cancer (NSCLC), undifferentiated large cell carcinoma indicates aggressive cancer, while other types of lung cancer suggest less aggressive cancers. For renal cell carcinoma (RCC), papillary and sarcomotoid carcinomas indicate aggressive cancers while the lack of these carcinomas is indicative of less aggressive cancers. In some embodiments, a tumor is evaluated for one or more of these markers and, if classified as having an aggressive cancer based on the results, is provided the treatments described herein.

In some embodiments, the present compositions and methods pertain to the treatment of breast cancer, including, without limitation, various breast cancer subtypes. For example, in some embodiments, the breast cancer may be HER2+. In some embodiments, the breast cancer is hormone receptor positive, including, without limitation luminal A breast cancer (LUM A), and luminal B breast cancer (LUM B). In various embodiments, such subtypes may be evaluated using molecular subtyping and/or the proliferative marker Ki67 (e.g. a cut off of Ki67 14%). In various embodiments, the breast cancer is basal-like breast cancer (BLBC), which is particularly treatment-resistant due to a lack of steroid hormone receptors and human epidermal growth factor receptor 2 (see, e.g. Toft et al. *Mol Endocrinol.* 2011 February; 25(2): 199-211, the entire contents of which are hereby incorporated by reference in their entirety). In various embodiments, the breast cancer is one or more of HER2+, LUM A, LUM B, and BLBC.

In some embodiments, the present compositions are paired with the appropriate treatment regimens by subtype. For example, LUM A is generally thought of as less aggressive and may warrant combination with only endocrine therapy while LUM B is generally thought of as more aggressive and may warrant combination with endocrine therapy and chemotherapy.

In various specific embodiments, the patients that may benefits from the present compositions and methods are characterized by upregulation of a cell marker selected from one or more of c-myc, YB1, FOXO1, BRM, OCT-4, and POSTN. In various embodiments, upregulation is assessed in an aggressive cancer patient and is relative to a less aggressive cancer, or relative to a non-cancerous state.

In some embodiments, the patient has relapsed from cancer. For example, the present methods relate to treatment of cancer in a patient that has relapsed from a previous cancer. In some embodiments, the treatment is of relapsed breast cancer.

In various embodiments the present invention relates to aggressive cancers. For example, such cancers can be selected from various types and subtypes of basal cell carcinoma, biliary tract cancer; bladder cancer; bone cancer; brain and central nervous system cancer; breast cancer; cancer of the peritoneum; cervical cancer; choriocarcinoma; colon and rectum cancer; connective tissue cancer; cancer of the digestive system; endometrial cancer; esophageal cancer; eye cancer; cancer of the head and neck; gastric cancer (including gastrointestinal cancer); glioblastoma; hepatic carcinoma; hepatoma; intra-epithelial neoplasm; kidney or renal cancer; larynx cancer; leukemia; liver cancer; lung cancer (e.g., small-cell lung cancer, non-small cell lung cancer, adenocarcinoma of the lung, and squamous carcinoma of the lung); melanoma; myeloma; neuroblastoma; oral cavity cancer (e.g., lip, tongue, mouth, and pharynx); ovarian cancer; pancreatic cancer; prostate cancer; retinoblastoma; rhabdomyosarcoma; rectal cancer; cancer of the respiratory system; salivary gland carcinoma; sarcoma; skin cancer; squamous cell cancer; stomach cancer; testicular cancer; thyroid cancer; uterine or endometrial cancer; cancer of the urinary system; vaginal cancer; vulval cancer; lymphoma including Hodgkin's and non-Hodgkin's lymphoma, as well as B-cell lymphoma (including low grade/follicular non-Hodgkin's lymphoma (NHL); small lymphocytic (SL) NHL; intermediate grade/follicular NHL; intermediate grade diffuse NHL; high grade immunoblastic NHL; high grade lymphoblastic NHL; high grade small non-cleaved cell NHL; bulky disease NHL; mantle cell lymphoma; AIDS-related lymphoma; and Waldenstrom's Macroglobulinemia; chronic lymphocytic leukemia (CLL); acute lymphoblastic leukemia (ALL); acute myelocytic leukemia; Hairy cell leukemia; chronic myeloblastic leukemia; as well as other carcinomas and sarcomas (e.g. fibrosarcoma, myxosarcoma, liposarcoma, chondrosarcoma, osteogenic sarcoma, chordoma, angiosarcoma, endotheliosarcoma, lymphangiosarcoma, lymphangioendotheliosarcoma, synovioma, mesothelioma, Ewing's tumor, leiomyosarcoma, rhabdomyosarcoma, Kaposi's sarcoma, adenocarcinoma, sweat gland carcinoma, sebaceous gland carcinoma, papillary carcinoma, papillary adenocarcinomas, cystadenocarcinoma, medullary carcinoma, bronchogenic carcinoma, renal cell carcinoma, hepatoma, bile duct carcinoma, choriocarcinoma, seminoma, and embryonal carcinoma); Wilms' tumor; solid tissue cancers (e.g., skin cancer, head and neck tumors, breast tumors, endothelioma, lung cancer, osteoblastoma and osteoclastoma); glioma, astrocytoma, medulloblastoma, craniopharyngioma, ependymoma, pinealoma, hemangioblastoma, acoustic neuroma, oligodendroglioma, meningioma, neuroblastoma, and retinoblastoma, heavy chain disease, metastases, or any disease or disorder characterized by uncontrolled cell growth; and post-transplant lymphoproliferative disorder (PTLD), as well as abnormal vascular proliferation associated with phakomatoses, edema (such as that associated with brain tumors), and Meigs' syndrome.

In some embodiments, the cancer is an aggressive form of one or more of abdominal, adrenal, bladder, blood, bone, brain, breast, cervical, colon, endometrial, esophageal, eye, head and neck, intestinal, kidney, liver, lung, ovarian, pancreatic, prostate, sarcoma, skin, spleen, stomach, testicular, thyroid, uterine, vaginal, and vulval cancer.

In some embodiments, the cancer is an aggressive form of one or more of breast cancer, ovarian cancer, prostate cancer, uterine cancer, colon cancer, endometrial cancer, and stomach cancer.

In a specific embodiment, the cancer is breast cancer, including aggressive breast cancer. In a specific embodiment, the aggressive cancer is metastatic breast cancer. In some aspects, the invention provides for methods for treating an aggressive breast cancer, comprising administering an antisense oligonucleotide to one or more of miR-199a, miR-214, miR-34a, miR-762, miR-1915, and Let-7b to a subject in need thereof. In some aspects use of an antisense oligonucleotide to one or more of miR-199a, miR-214, miR-34a, miR-762, miR-1915, and Let-7b in the treatment or manufacture of a medicament for the treatment of metastatic breast cancer is provided.

Breast cancer is a type of cancer originating from breast tissue, including the inner lining of milk ducts (ductal carcinomas) or the lobules that supply the ducts with milk (lobular carcinomas). Breast cancer occurs in humans and other mammals. Most human cases occur in women, male breast cancer can also occur. In some embodiments, the present invention pertains to a female human breast cancer subject. In some embodiments, the present invention pertains to a male human breast cancer subject.

As described herein, breast cancers may be classified by one or more grading systems, which may, influence the prognosis and can affect treatment response. Histopathology, describes the classification of breast cancer by its histological appearance. Most breast cancers are derived from the epithelium lining the ducts or lobules, and these cancers are classified as ductal or lobular carcinoma. Carcinoma in situ is growth of low grade cancerous or precancerous cells within a particular tissue compartment such as the mammary duct without invasion of the surrounding tissue. By contrast, invasive carcinoma does not confine itself to the initial tissue compartment. Grading compares the appearance of breast cancer cells to the appearance of normal breast tissue. In some embodiments, cancerous cells lose the differentiation and orderly arrangement that characterizes normal cells and normal populations of cells. Further, cell division may become uncontrolled and cell nuclei may become less uniform. Cells can be binned as well differentiated (low grade), moderately differentiated (intermediate grade), and poorly differentiated (high grade) as the cells progressively lose the features seen in normal breast cells. Poorly differentiated cancers (the ones whose tissue is least like normal breast tissue) have a worse prognosis, and are the subject of various embodiments of the present invention. Breast cancer staging can be undertaken using the TNM system, which is based the size of the tumor (T), whether or not the tumor has spread to the lymph nodes (N) in the armpits, and whether the tumor has metastasized (M). Larger size, nodal spread, and metastasis have a larger stage number and a worse prognosis. The main stages are: stage 0 is a pre-cancerous or marker condition, either ductal carcinoma in situ (DCIS) or lobular carcinoma in situ (LCIS); stages 1-3 are within the breast or regional lymph nodes; and stage 4 is metastatic cancer that often has a less favorable prognosis. DNA testing of various types including DNA microarrays may also be used to compare normal cells to breast cancer cells. The specific changes in a particular breast cancer can be used to classify the cancer in several ways, and may assist in choosing the most effective treatment for that DNA type. As described herein, these parameters may direct treatment of particularly aggressive breast cancers with the miR-inhibiting agents described herein.

In some embodiments, the breast cancer is characterized by the presence or absence of one or more of estrogen receptor (ER), progesterone receptor (PR), HER2, androgen receptor (AR), and prolactin receptor (PRLr). In some embodiments, the breast cancer is triple negative. In another embodiment, the breast cancer is ER−. In still another embodiment, the breast cancer is HER2+. HER2 (also known as Neu, ErbB-2, CD340, or p185) is a protein that in humans is encoded by the ERBB2 gene, a known proto-oncogene. HER2 is a member of the epidermal growth factor receptor (EGFR/ErbB) family. Amplification or over-expression of this gene has been shown to play an important role in the pathogenesis and progression of certain aggressive types of cancer, including breast cancer. Without wishing to be bound by theory, signaling pathways activated by HER2 include, but are not limited to, mitogen-activated protein kinase (MAPK), phosphoinositide 3-kinase (PI3K/Akt), phospholipase C γ, protein kinase C (PKC), and signal transducer and activator of transcription (STAT). Generally, signaling through the ErbB family of receptors promotes cell proliferation and opposes apoptosis. Amplification or over-expression of the ERBB2 gene occurs in approximately 30% of breast cancers. It is strongly associated with increased disease recurrence and a worse prognosis. Accordingly, HER2+ breast cancer is a particularly aggressive subtype of breast cancer and often has a bad prognosis.

In a specific embodiment, the cancer is a bone cancer, including, for example, aggressive bone cancers, such as bone metastasis. For example, the present invention relates to, in some embodiments, the development of solid tumors in the skeleton. Bone cancer is a malignant tumor of the bone that may destroy normal bone tissue. Bone tumors may be malignant or benign. In some embodiments, the present invention relates to malignant bone cancers, including aggressive types. In some embodiments, the bone cancer is a primary bone cancer or a secondary bone cancer. Malignant primary bone tumors include, for example, osteosarcoma (which arises from osteoid tissue in the bone; this tumor occurs most often in the knee and upper arm), chondrosarcoma (which begins in cartilaginous tissue, and is most often in the pelvis, upper leg, and shoulder), Ewing Sarcoma Family of Tumors (ESFTs, which usually occur in bone but may also arise in soft tissue (muscle, fat, fibrous tissue, blood vessels, or other supporting tissue), which tumors are most common along the backbone and pelvis and in the legs and arms), fibrosarcoma, and other types. In various embodiments, the aggressiveness of any of these bone cancers is evaluated with one or more of X-rays, bone scan, computed tomography (CT or CAT) scan, magnetic resonance imaging (MRI) procedure, positron emission tomography (PET) scan, an angiogram, a biopsy and one or more blood tests (e.g. for alkaline phosphatase).

In various embodiments, the present inventive cancer treatments are useful for various secondary tumors. In an illustrative embodiment, the secondary tumor is a secondary bone cancer (by way of non-limiting example, a breast or a prostate tumor that has invaded the bone).

In some embodiments, the inventive cancer treatments comprise a reduction or prevention of one or more of: metastasis, cancer progression, cancer invasion, cancer stem cell propagation, and tumor/stroma crosstalk.

In various embodiments, the present invention provides for a reduction in numbers, or prevention of formation, of cancer stem cells (as detected by, for example ALDH expression, including use of the ALDEFLUOR kit). Cancer stem cells have an ability for self-renewal and multipotency. The cancer stem cell hypothesis states that, although cancer stem cells represent a rare population of cells within a tumor, their high tumorigenic capacity drives tumorigenesis. Cancer stem cells have extensive proliferative capacity; are capable of asymmetric cell division to generate one or more kinds of differentiated progeny with reduced proliferative or developmental potential; and are capable of symmetric cell divisions for self-renewal or self-maintenance. Due to the intrinsic stem cell-like properties of cancer stem cell, cancer stem cell proliferation generates more cancer stem cells, and all the differentiated cell types that compose the bulk of the tumor. Non-cancer stem cells in the tumor have been shown to proliferate at a faster rate than cancer stem cells, but have little tumor-initiating potential. Because cancer stem cells exhibit increased resistance to toxic and chemical insults, this specific subpopulation of cells is believed to underlie resistance to chemotherapy and disease relapse. In fact, the cancer stem cell model posits that all cancer stem cells must be eradicated to eliminate a tumor and prevent its recurrence. Accordingly, the present agents, which are efficacious against aggressive cancers, are useful in preventing or diminishing cancer stem cells in a patient.

In various embodiments, the present invention provides for a reduction or prevention of tumor/stroma crosstalk. Maintenance of both normal epithelial tissues and their malignant counterparts is supported by the host tissue stroma. The tumor stroma mainly consists of the basement membrane, fibroblasts, extracellular matrix, immune cells, and vasculature. Although most host cells in the stroma possess certain tumor-suppressing abilities, the stroma will change during malignancy and eventually promote growth, invasion, and metastasis. Stromal changes at the invasion front include the appearance of carcinoma-associated fibroblasts (CAFs). CAFs constitute a major portion of the reactive tumor stroma and play a crucial role in tumor progression. The main precursors of CAFs are normal fibroblasts, and the transdifferentiation of fibroblasts to CAFs is driven to a great extent by cancer-derived cytokines such as transforming growth factor-β. The crosstalk between cancer cells and the tumor stroma is linked to the progression of tumors and their metastasis and is reduced by the miR inhibiting agents of the present invention. For example, in some embodiments, the present treatments affect the heterotypic crosstalk that takes place between the epithelial and stromal compartments in breast tumors.

In various embodiments, the methods and uses of the present invention affect the level of FOXP2. For example, in some embodiments, the present treatments lead to an increase in FOXP2 levels (e.g. nucleic acid or protein) and/or a restoration of those levels to a pre-cancerous or less aggressive type, subtype or stage of cancer. In some embodiments, the expression and/or activity of FOXP2 is not reduced in the subject following administration of the inhibitor.

In various embodiments, the present polynucleotide agents are useful as adjuvant therapies. Adjuvant therapy is treatment that is given in addition to a primary or main treatment. In various embodiments, the cancer is aggressive and the patient is undergoing one or more primary or main treatments as described herein. The present micro-RNA inhibitors (for example, antisense of one or more of miR-119a, miR-214, miR-34a, miR-762, miR-1915, and Let-7b) may be administered in conjunction with a primary or main treatment in the context of an aggressive cancer type. For example, the present micro-RNA inhibitors, in the context of aggressive breast cancer, may be adjuvant to resection of the primary tumor(s), including breast tumor(s).

Also, in various embodiments, the present polynucleotide agents are useful as neoadjuvant therapies. Neoadjuvant therapy refers to therapy that is given to before primary or main treatment, often to prepare a patient for the primary or main treatment. For example, in some embodiments, the cancer being treated is aggressive and therefore treatment with the present agents will lessen the severity of the disease and make it more amenable to a primary or main treatment. In a specific embodiment, micro-RNA inhibitors (for example, antisense of one or more of miR-119a, miR-214, miR-34a, miR-762, miR-1915, and Let-7b) are used in treating a patient with an aggressive cancer to allow for subsequent resection (e.g. surgical resection in a breast cancer patient).

The present micro-RNA inhibitors find use in a variety of combination therapies (including as sequential or simultaneous co-administration and/or as co-formulation), including the adjuvant and neoadjuvant approaches described herein.

By way of non-limiting example, a combination agent and/or the primary or main treatment may be one or more regimens (including, for example, monotherapy and combination therapies). The combination agent and/or the primary or main treatment may be surgical resection, radiation therapy, photodynamic therapy, chemotherapy, targeted therapy, other immunotherapy, and supportive therapy (e.g., painkillers, diuretics, antidiuretics, antivirals, antibiotics, nutritional supplements, anemia therapeutics, blood clotting therapeutics, bone therapeutics, and psychiatric and psychological therapeutics). Such other anti-cancer treatments may be provided sequentially (e.g., before or after) or simultaneously with the administration of a therapeutic agent as described herein.

Examples of chemotherapeutic agents include, but are not limited to, alkylating agents such as thiotepa and CYTOXAN cyclosphosphamide; alkyl sulfonates such as busulfan, improsulfan and piposulfan; aziridines such as benzodopa, carboquone, meturedopa, and uredopa; ethylenimines and methylamelamines including altretamine, triethylenemelamine, trietylenephosphoramide, triethiylenethiophosphoramide and trimethylolomelamine; acetogenins (e.g., bullatacin and bullatacinone); a camptothecin (including the synthetic analogue topotecan); bryostatin; callystatin; CC-1065 (including its adozelesin, carzelesin and bizelesin synthetic analogues); cryptophycins (e.g., cryptophycin 1 and cryptophycin 8); dolastatin; duocarmycin (including the synthetic analogues, KW-2189 and CB 1-TM1); eleutherobin; pancratistatin; a sarcodictyin; spongistatin; nitrogen mustards such as chlorambucil, chlornaphazine, cholophosphamide, estramustine, ifosfamide, mechlorethamine, mechlorethamine oxide hydrochloride, melphalan, novembichin, phenesterine, prednimustine, trofosfamide, uracil mustard; nitrosureas such as carmustine, chlorozotocin, fotemustine, lomustine, nimustine, and ranimnustine; antibiotics such as the enediyne antibiotics (e.g., calicheamicin, especially calicheamicin gammaII and calicheamicin omegaII (see, e.g., Agnew, Chem. Intl. Ed. Engl., 33: 183-186 (1994)); dynemicin, including dynemicin A; bisphosphonates, such as clodronate; an esperamicin; as well as neocarzinostatin chromophore and related chromoprotein enediyne antiobiotic chromophores), aclacinomysins, actinomycin, authramycin, azaserine, bleomycins, cactinomycin, carabicin, caminomycin, carzinophilin, chromomycinis, dactinomycin, daunorubicin, detorubicin, 6-diazo-5-oxo-L-norleucine, ADRIAMYCIN doxorubicin (including morpholino-doxorubicin, cyanomorpholino-doxorubicin, 2-pyrrolino-doxorubicin and deoxydoxorubicin), epirubicin, esorubicin, idarubicin, marcellomycin, mitomycins such as mitomycin C, mycophenolic acid, nogalamycin, olivomycins, peplomycin, potfiromycin, puromycin, quelamycin, rodorubicin, streptonigrin, streptozocin, tubercidin, ubenimex, zinostatin, zorubicin; anti-metabolites such as methotrexate and 5-fluorouracil (5-FU); folic acid analogues such as denopterin, methotrexate, pteropterin, trimetrexate; purine analogs such as fludarabine, 6-mercaptopurine, thiamiprine, thioguanine; pyrimidine analogs such as ancitabine, azacitidine, 6-azauridine, carmofur, cytarabine, dideoxyuridine, doxifluridine, enocitabine, floxuridine; androgens such as calusterone, dromostanolone propionate, epitiostanol, mepitiostane, testolactone; anti-adrenals such as minoglutethimide, mitotane, trilostane; folic acid replenisher such as frolinic acid; aceglatone; aldophosphamide glycoside; aminolevulinic acid; eniluracil; amsacrine; bestrabucil; bisantrene; edatraxate; def of amine; demecolcine; diaziquone; elformithine; elliptinium acetate; an epothilone; etoglucid; gallium nitrate; hydroxyurea; lentinan; lonidainine; maytansinoids such as maytansine and ansamitocins; mitoguazone; mitoxantrone; mopidanmol; nitraerine; pentostatin; phenamet; pirarubicin; losoxantrone; podophyllinic acid; 2-ethylhydrazide; procarbazine; PSK polysaccharide complex (JHS Natural Products, Eugene, Oreg.); razoxane; rhizoxin; sizofuran; spirogermanium; tenuazonic acid; triaziquone; 2,2',2"-trichlorotriethylamine; trichothecenes (e.g., T-2 toxin, verracurin A, roridin A and anguidine); urethan; vindesine; dacarbazine; mannomustine; mitobronitol; mitolactol; pipobroman; gacytosine; arabinoside ("Ara-C"); cyclophosphamide; thiotepa; taxoids, e.g., TAXOL paclitaxel (Bristol-Myers Squibb Oncology, Princeton, N.J.), ABRAXANE Cremophor-free, albumin-engineered nanoparticle formulation of paclitaxel (American Pharmaceutical Partners, Schaumberg, Ill.), and TAXOTERE doxetaxel (Rhone-Poulenc Rorer, Antony, France); chloranbucil; GEMZAR gemcitabine; 6-thioguanine; mercaptopurine; methotrexate; platinum analogs such as cisplatin, oxaliplatin and carboplatin; vinblastine; platinum; etoposide (VP-16); ifosfamide; mitoxantrone; vincristine; NAVELBINE. vinorelbine; novantrone; teniposide; edatrexate; daunomycin; aminopterin; xeloda; ibandronate; irinotecan (Camptosar, CPT-11) (including the treatment regimen of irinotecan with 5-FU and leucovorin); topoisomerase inhibitor RFS 2000; difluoromethylornithine (DMFO); retinoids such as retinoic acid; capecitabine; combretastatin; leucovorin (LV); oxaliplatin, including the oxaliplatin treatment regimen (FOLFOX); lapatinib (Tykerb); inhibitors of PKC-α, Raf, H-Ras, EGFR (e.g., erlotinib (Tarceva)) and VEGF-A that reduce cell proliferation and pharmaceutically acceptable salts, acids or derivatives of any of the above.

Another embodiment of the present invention is a pharmaceutical composition, or use of pharmaceutical composition, comprising an inhibitor of an miRNA, such as one or more of miR-199a, miR-214, miR-34a, miR-762, miR-1915, and Let-7b, and a pharmaceutically acceptable carrier. Where clinical applications are contemplated, pharmaceutical compositions may be prepared in a form appropriate for the intended application. Generally, this will entail preparing compositions that are essentially free of pyrogens, as well as other impurities that could be harmful to humans or animals.

In one embodiment, a pharmaceutical composition comprises an effective dose of an miRNA inhibitor, by way of non-limiting example, an antisense oligonucleotide directed to one or more of miR-199a, miR-214, miR-34a, miR-762, miR-1915, and Let-7b, and a pharmaceutically acceptable carrier. An effective dose is an amount sufficient to effect a beneficial or desired clinical result. An effective dose of an miRNA inhibitor of the invention may be from about 1 mg/kg to about 100 mg/kg, about 2.5 mg/kg to about 50 mg/kg, or about 5 mg/kg to about 25 mg/kg. The precise determination of what would be considered an effective dose may be based on factors individual to each patient, including their size, age, type of cancer, and nature of inhibitor or agonist (non-limiting examples include antagomir, expression construct, antisense oligonucleotide, polynucleotide duplex, etc.). Therefore, dosages can be readily ascertained by those of ordinary skill in the art from this disclosure and the knowledge in the art. For example, doses may be determined with reference *Physicians' Desk Reference*, 66th Edition, PDR Network; 2012 Edition (Dec. 27, 2011), the contents of which are incorporated by reference in its entirety.

A beneficial or desired clinical result may include, inter alia, a reduction in tumor size and/or tumor growth and/or a reduction of a cancer marker that is associated with the presence of cancer as compared to what is observed without administration of the inhibitor. A beneficial or desired clinical result may also include, inter alia, an increased presence of a marker that is associated with a reduction of cancer as compared to what is observed without administration of the inhibitor. Also included in a beneficial or desired clinical result is, inter alia, an increased amount of a gene comprising a marker linked to cancer etiology as compared to what is observed without administration of the inhibitor.

Colloidal dispersion systems, such as macromolecule complexes, nanocapsules, microspheres, beads, and lipid-based systems including oil-in-water emulsions, micelles, mixed micelles, and liposomes, may be used as delivery vehicles for the oligonucleotide inhibitors of oncogenic miRNA function, polynucleotides encoding tumor suppressor miRNA agonists, or constructs expressing particular miRNA inhibitors or agonists. Commercially available fat emulsions that are suitable for delivering the nucleic acids of the invention to cancer tissues include INTRALIPID®, LIPOSYN®, LIPOSYN® II, LIPOSYN® III, Nutrilipid, and other similar lipid emulsions. A colloidal system for use as a delivery vehicle in vivo is a liposome (i.e., an artificial membrane vesicle). The preparation and use of such systems is well known in the art. Exemplary formulations are also disclosed in U.S. Pat. Nos. 5,981,505; 6,217,900; 6,383,512; 5,783,565; 7,202,227; 6,379,965; 6,127,170; 5,837,533; 6,747,014; and WO03/093449, which are herein incorporated by reference in their entireties.

One will generally desire to employ appropriate salts and buffers to render delivery vehicles stable and allow for uptake by target cells. Aqueous compositions of the present invention comprise an effective amount of the delivery vehicle comprising the inhibitor polynucleotides (e.g., liposomes or other complexes or expression vectors) dissolved or dispersed in a pharmaceutically acceptable carrier or aqueous medium. The phrases pharmaceutically acceptable or pharmacologically acceptable refer to molecular entities and compositions that do not produce adverse, allergic, or other untoward reactions when administered to an animal or a human. As used herein, pharmaceutically acceptable carrier includes solvents, buffers, solutions, dispersion media, coatings, antibacterial and antifungal agents, isotonic and absorption delaying agents and the like acceptable for use in formulating pharmaceuticals, such as pharmaceuticals suitable for administration to humans. The use of such media and agents for pharmaceutically active substances is well known in the art. Except insofar as any conventional media or agent is incompatible with the active ingredients of the present invention, its use in therapeutic compositions is contemplated. Supplementary active ingredients also can be incorporated into the compositions, provided they do not inactivate the vectors or polynucleotides of the compositions.

The active compositions of the present invention may include classic pharmaceutical preparations. Administration of these compositions according to the present invention may be via any common route so long as the target tissue is available via that route. This includes oral, nasal, or buccal. Alternatively, administration may be by intradermal, subcutaneous, intramuscular, intraperitoneal or intravenous injection, or by direct injection into cancer tissue. The agents disclosed herein may also be administered by catheter systems. Such compositions would normally be administered as pharmaceutically acceptable compositions as described herein.

The active compounds may also be administered parenterally or intraperitoneally. By way of illustration, solutions of the active compounds as free base or pharmacologically acceptable salts can be prepared in water suitably mixed with a surfactant, such as hydroxypropylcellulose. Dispersions can also be prepared in glycerol, liquid polyethylene glycols, and mixtures thereof and in oils. Under ordinary conditions of storage and use, these preparations generally contain a preservative to prevent the growth of microorganisms.

The pharmaceutical forms suitable for injectable use or catheter delivery include, for example, sterile aqueous solutions or dispersions and sterile powders for the extemporaneous preparation of sterile injectable solutions or dispersions. Generally, these preparations are sterile and fluid to the extent that easy injectability exists. Preparations should be stable under the conditions of manufacture and storage and should be preserved against the contaminating action of microorganisms, such as bacteria and fungi. Appropriate solvents or dispersion media may contain, for example, water, ethanol, polyol (for example, glycerol, propylene glycol, and liquid polyethylene glycol, and the like), suitable mixtures thereof, and vegetable oils. The proper fluidity can be maintained, for example, by the use of a coating, such as lecithin, by the maintenance of the required particle size in the case of dispersion and by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars or sodium chloride. Prolonged absorption of the injectable compositions can be brought about by the use in the compositions of agents delaying absorption, for example, aluminum monostearate and gelatin.

Sterile injectable solutions may be prepared by incorporating the active compounds in an appropriate amount into a solvent along with any other ingredients (for example as enumerated above) as desired, followed by filtered sterilization. Generally, dispersions are prepared by incorporating the various sterilized active ingredients into a sterile vehicle which contains the basic dispersion medium and the desired other ingredients, e.g., as enumerated above. In the case of sterile powders for the preparation of sterile injectable solutions, the preferred methods of preparation include vacuum-drying and freeze-drying techniques which yield a powder of the active ingredient(s) plus any additional desired ingredient from a previously sterile-filtered solution thereof.

Upon formulation, solutions may be administered in a manner compatible with the dosage formulation and in such amount as is therapeutically effective. The formulations may easily be administered in a variety of dosage forms such as injectable solutions, drug release capsules and the like. For parenteral administration in an aqueous solution, for example, the solution generally is suitably buffered and the liquid diluent first rendered isotonic with, for example, sufficient saline or glucose. Such aqueous solutions may be used, for example, for intravenous, intramuscular, subcutaneous and intraperitoneal administration. Preferably, sterile aqueous media are employed as is known to those of skill in the art, particularly in light of the present disclosure. By way of illustration, a single dose may be dissolved in 1 ml of isotonic NaCl solution and either added to 1000 ml of hypodermoclysis fluid or injected at the proposed site of infusion (see, e.g, *Remington's Pharmaceutical Sciences*, 15th Edition, pages 1035-1038 and 1570-1580, the contents of which are hereby incorporated by reference). Some variation in dosage will necessarily occur depending on the condition of the subject being treated. The person responsible for administration will, in any event, determine the appropriate dose for the individual subject. Moreover, for human administration, preparations should meet sterility, pyrogenicity, general safety and purity standards as required by the FDA Office of Biologics standards.

In some embodiments, the terms "patient" and "subject" are used interchangeably. In some embodiments, the subject and/or animal is a mammal, e.g., a human, mouse, rat, guinea pig, dog, cat, horse, cow, pig, rabbit, sheep, or non-human primate, such as a monkey, chimpanzee, or baboon. In other embodiments, the subject and/or animal is a non-mammal, such, for example, a zebrafish. In some embodiments, the subject and/or animal may comprise fluorescently-tagged cells (with e.g. GFP). In some embodiments, the subject and/or animal is a transgenic animal comprising a fluorescent cell.

In some embodiments, the subject and/or animal is a human. In some embodiments, the human is a pediatric human. In other embodiments, the human is an adult human. In other embodiments, the human is a geriatric human. In other embodiments, the human may be referred to as a patient.

In certain embodiments, the human has an age in a range of from about 6 to about 18 months old, from about 18 to about 36 months old, from about 1 to about 5 years old, from about 5 to about 10 years old, from about 10 to about 15 years old, from about 15 to about 20 years old, from about 20 to about 25 years old, from about 25 to about 30 years old, from about 30 to about 35 years old, from about 35 to about 40 years old, from about 40 to about 45 years old, from about 45 to about 50 years old, from about 50 to about 55 years old, from about 55 to about 60 years old, from about 60 to about 65 years old, from about 65 to about 70 years old, from about 70 to about 75 years old, from about 75 to about 80 years old, from about 80 to about 85 years old, from about 85 to about 90 years old, from about 90 to about 95 years old or from about 95 to about 100 years old.

In other embodiments, the subject is a non-human animal, and therefore the invention pertains to veterinary use. In a specific embodiment, the non-human animal is a household pet. In another specific embodiment, the non-human animal is a livestock animal.

The invention also provides kits that can simplify the administration of any agent described herein, such as an inhibitor of an oncogenic miRNA, including antisense oligonucleotide directed to one or more of miR-199a, miR-214, miR-34a, miR-762, miR-1915, and Let-7b. An exemplary kit of the invention comprises any composition described herein in unit dosage form. In one embodiment, the unit dosage form is a container, such as a pre-filled syringe, which can be sterile, containing any agent described herein and a pharmaceutically acceptable carrier, diluent, excipient, or vehicle. The kit can further comprise a label or printed instructions instructing the use of any agent described herein. The kit may also include a lid speculum, topical anesthetic, and a cleaning agent for the administration location. The kit can further comprise one or more additional agent, such as a second inhibitor of an oncogenic miRNA, or a biologic, therapeutic, chemotherapeutic or drug described herein. In one embodiment, the kit comprises a container containing an effective amount of a composition of the invention and an effective amount of another composition, such those described herein.

In some embodiments, the present invention provides a method of evaluating a subject's cancer, including but not limited to diagnosis, prognosis, and response to treatment.

In one aspect, the invention provides a method for evaluating a tumor, comprising: (a) determining a relative level of malignant cells that express FOXP2 in a human subject tumor specimen or cells cultured therefrom; and (b) classifying the subject into a high or low risk group based on the presence, absence, or level of at least one component of FOXP2. In some embodiments, the method for evaluating a tumor comprises a further step of treating the subject with an adjuvant or neoadjuvant therapy if the subject is classified as high risk or withholding an adjuvant or neoadjuvant therapy is the subject is classified as low risk is provided. In some embodiments, the method for evaluating a tumor comprises a further step of determining a relative level of one or more of BRCA1, BRCA2, p53, RAS, AR, HER-2, ER, AR and PR and/or conducting one or more of a mammogram, MRI, ultrasound, ductogram, nipple discharge test, ductal lavage, and nipple aspiration.

In other aspects, the invention provides a method for treating cancer, comprising (a) measuring a presence, absence, or level of FOXP2 in a human subject tumor specimen or cells cultured therefrom; (b) classifying the subject into a high or low risk group based on the presence, absence, or level of at least one component of FOXP2; and (c) administering an effective amount of micro-RNA inhibitor of one or more of miR-119a, miR-214, miR-34a, miR-762, miR-1915, and Let-7b to a human subject that is classified as high risk.

In some embodiments, the absence and/or deregulation of FOXP2 is correlated with poor survival rates in patients with various cancers such as bone and breast cancer. In some embodiments, the present invention relates to a method of evaluating a cancer based on measurement of FOXP2 levels. In one embodiment, detection of an absence and/or deregulation of FOXP2 is associated with an aggressive cancer and an aggressive treatment regime is employed, optionally including adjuvant and neoadjuvant therapies. In another embodiment, detection of an absence and/or deregulation of FOXP2 is associated with an aggressive cancer and these circumstances may direct cessation of aggressive treatment and the use of palliative care, to avoid unnecessary toxicity from ineffective chemotherapies for a better quality of life. In one embodiment, a presence and/or upregulation of FOXP2 is associated with a less aggressive cancer and a less aggressive treatment regime is employed. In these embodiments, adjuvant and neoadjuvant therapies may be curtailed or avoided altogether.

In some embodiments, the presence and/or upregulation of one or more of miR-199a, miR-214, miR-34a, miR-762, miR-1915, and Let-7b is correlated with poor survival rates in patients with various cancers such as bone and breast cancer. In some embodiments, the present invention relates to a method of evaluating a cancer based on measurement of one or more of miR-199a, miR-214, miR-34a, miR-762, miR-1915, and Let-7b levels. In one embodiment, detection of a presence and/or upregulation of one or more of miR-199a, miR-214, miR-34a, miR-762, miR-1915, and Let-7b is associated with an aggressive cancer and an aggressive treatment regime is employed, optionally including adjuvant and neoadjuvant therapies. In another embodiment, detection of a presence and/or upregulation of one or more of miR-199a, miR-214, miR-34a, miR-762, miR-1915, and Let-7b is associated with an aggressive cancer and these circumstances may direct cessation of aggressive treatment and the use of palliative care, to avoid unnecessary toxicity from ineffective chemotherapies for a better quality of life. In one embodiment, lack of one or more of miR-199a, miR-214, miR-34a, miR-762, miR-1915, and Let-7b is associated with a less aggressive cancer and a less aggressive treatment regime is employed. In these embodiments, adjuvant and neoadjuvant therapies may be curtailed or avoided altogether.

In some embodiments, the presence and/or upregulation of one or more of c-myc, YB1, FOX01, BRM, OCT-4, and POSTN is correlated with poor survival rates in patients with various cancers such as bone and breast cancer. In some embodiments, the present invention relates to a method of evaluating a cancer based on measurement of one or more of c-myc, YB1, FOX01, BRM, OCT-4, and POSTN levels. In one embodiment, detection of a presence and/or upregulation of one or more of c-myc, YB1, FOX01, BRM, OCT-4, and POSTN is associated with an aggressive cancer and an aggressive treatment regime is employed, optionally including adjuvant and neoadjuvant therapies. In another embodiment, detection of a presence and/or upregulation of one or more of c-myc, YB1, FOXO1, BRM, OCT-4, and POSTN is associated with an aggressive cancer and these circumstances may direct cessation of aggressive treatment and the use of palliative care, to avoid unnecessary toxicity from ineffective chemotherapies for a better quality of life. In one embodiment, lack of one or more of c-myc, YB1, FOXO1, BRM, OCT-4, and POSTN is associated with a less aggressive cancer and a less aggressive treatment regime is employed. In these embodiments, adjuvant and neoadjuvant therapies may be curtailed or avoided altogether.

In various embodiments, evaluation comprises any one of diagnosis, prognosis, and response to treatment. Diagnosis refers to the process of attempting to determine or identify a possible disease or disorder, such as, for example, cancer, or breast cancer. Prognosis refers to the predicting of a likely outcome of a disease or disorder, such as, for example, cancer, or breast cancer. A complete prognosis often includes the expected duration, the function, and a description of the course of the disease, such as progressive decline, intermittent crisis, or sudden, unpredictable crisis. Response to treatment is a prediction of a patient's medical outcome when receiving a treatment. Responses to treatment can be, by way of non-limiting example, pathological complete response, survival, and probability of recurrence.

In various embodiments, reduction or absence of FOXP2 is indicative of a high risk while an increase or presence of FOXP2 is indicative of a low risk. In some embodiments, the high risk classification is predictive of a positive response to and/or benefit from neoadjuvant chemotherapy and/or adjuvant chemotherapy and optionally directs providing a neoadjuvant therapy and/or adjuvant therapy while the low risk classification is predictive of a lack of a positive response to and/or benefit from neoadjuvant chemotherapy and/or adjuvant chemotherapy and optionally directs withholding a neoadjuvant therapy and/or adjuvant therapy. In some embodiments, the high risk classification comprises a high level of cancer aggressiveness, wherein the aggressiveness is characterizable by one or more of a high tumor grade, low overall survival, high probability of metastasis, and the presence of a tumor marker indicative of aggressiveness while the low risk classification comprises a low level of cancer aggressiveness, wherein the aggressiveness is characterizable by one or more of a low tumor grade, high overall survival, low probability of metastasis, and the absence and/or reduction of a tumor marker indicative of aggressiveness.

In various embodiments, the measurement comprises evaluating a presence, absence, or level of a protein or nucleic acid. In another embodiment, the measurement comprises evaluating a presence, absence, or level of expression of a nucleic acid. In some embodiments the measurement of a nucleic acid comprises a an oligonucleotide primer or probe to one or more of FOXP2, miR-199a, miR-214, miR-34a, miR-762, miR-1915, and Let-7b. In some embodiments, the measurement of one or more of FOXP2, miR-199a, miR-214, miR-34a, miR-762, miR-1915, and Let-7b nucleic acid levels comprises one or more of reporter gene assays, Northern blot, Southern blot, nuclease protection assays, fluorescent in situ hybridization (FISH), PCR, reverse transcription PCR (RT-PCR), serial analysis of gene expression (SAGE), DNA microarrays, tiling array, RNA-Seq/whole transcriptome shotgun sequencing (WTSS), high-throughput sequencing, multiplex PCR, multiplex ligation-dependent probe amplification (MLPA), DNA sequencing by ligation, and Luminex/XMAP. n another embodiment, the measurement comprises evaluating a presence, absence, or level of expression of a protein, optionally using an antibody. For example, the present methods may comprise one or more of immunohistochemical staining, western blotting, in cell western, immunofluorescent staining, ELISA, and fluorescent activating cell sorting (FACS).

There are generally two strategies used for detection of epitopes on antigens in body fluids or tissues, direct methods and indirect methods. The direct method comprises a one-step staining, and may involve a labeled antibody (e.g. FITC conjugated antiserum) reacting directly with the antigen in a body fluid or tissue sample. The indirect method comprises an unlabeled primary antibody that reacts with the body fluid or tissue antigen, and a labeled secondary antibody that reacts with the primary antibody. Labels can include radioactive labels, fluorescent labels, hapten labels such as, biotin, or an enzyme such as horse radish peroxidase or alkaline phosphatase. Methods of conducting these assays are well known in the art. See, e.g., Harlow et al. (Antibodies, Cold Spring Harbor Laboratory, NY, 1988), Harlow et al. (Using Antibodies, A Laboratory Manual, Cold Spring Harbor Laboratory, NY, 1999), Virella (Medical Immunology, 6th edition, Informa HealthCare, New York, 2007), and Diamandis et al. (Immunoassays, Academic Press, Inc., New York, 1996). Kits for conducting these assays are commercially available from, for example, Clontech Laboratories, LLC. (Mountain View, Calif.).

In various embodiments, antibodies include whole antibodies and/or any antigen binding fragment (e.g., an antigen-binding portion) and/or single chains of these (e.g. an antibody comprising at least two heavy (H) chains and two light (L) chains inter-connected by disulfide bonds, an Fab fragment, a monovalent fragment consisting of the $V_L$, $V_H$, $C_L$ and CH1 domains; a F(ab)$_2$ fragment, a bivalent fragment including two Fab fragments linked by a disulfide bridge at the hinge region; a Fd fragment consisting of the $V_H$ and CH1 domains; a Fv fragment consisting of the $V_L$ and $V_H$ domains of a single arm of an antibody; and the like). In various embodiments, polyclonal and monoclonal antibodies are useful, as are isolated human or humanized antibodies, or functional fragments thereof.

Standard assays to evaluate the binding ability of the antibodies toward the target of various species are known in the art, including for example, ELISAs, western blots and RIAs. The binding kinetics (e.g., binding affinity) of antibodies also can be assessed by standard assays known in the art, such as by Biacore analysis.

In some embodiments, a pathologist may conduct the measurements described herein.

In various embodiments, measurements may employ automated or computer-implemented techniques that image, for example, a stained tumor sample, and quantify the various markers used, including quantifying cells that express multiple markers. Accordingly, in some embodiments, the invention provides computer programs and computer implemented products for carrying out the methods described herein. In one embodiment, the application provides a computer program product for use in conjunction with a computer having a processor and a memory connected to the processor, the computer program product comprising a computer readable storage medium having a computer mechanism encoded thereon, wherein the computer program mechanism may be loaded into the memory of the computer and cause the computer to carry out the methods described herein. In another embodiment, the application provides a computer implemented product for predicting a prognosis or classifying a subject by analysis of FOXP2, miR-199a, miR-214, miR-34a, miR-762, miR-1915, and/or Let-7b data. Such a computer implemented product may comprise a means for receiving values corresponding to a subject expression profile in a subject sample and a database comprising reference data associated with a prognosis, wherein computer implemented product selects the reference data most similar to the subject profile, to thereby predict a prognosis or classify the subject.

In various embodiments, an automated device and/or computer may be useful to implement the methods described herein including, for example, steps of imaging, measurement, and/or quantification. In some embodiments, such automated device and/or computer may allow for automation of the measurements described herein.

In some embodiments, the present invention includes the measurement of a tumor specimen, including biopsy or surgical specimen samples. In some embodiments, the biopsy is a human biopsy. In various embodiments, the biopsy is any one of a frozen tumor tissue specimen, cultured cells, circulating tumor cells, and a formalin-fixed paraffin-embedded tumor tissue specimen.

In some embodiments, the tumor specimen may be a biopsy sample, such as a frozen tumor tissue (cryosection) specimen. As is known in the art, a cryosection may employ a cryostat, which comprises a microtome inside a freezer. The surgical specimen is placed on a metal tissue disc which is then secured in a chuck and frozen rapidly to about −20° C. to about −30° C. The specimen is embedded in a gel like medium consisting of, for example, poly ethylene glycol and polyvinyl alcohol. The frozen tissue is cut frozen with the microtome portion of the cryostat, and the section is optionally picked up on a glass slide and stained.

In some embodiments, the tumor specimen may be a biopsy sample, such as cultured cells. These cells may be processed using the usual cell culture techniques that are known in the art. These cells may be circulating tumor cells.

In some embodiments, the tumor specimen may be a biopsy sample, such as a formalin-fixed paraffin-embedded (FFPE) tumor tissue specimen. As is known in the art, a biopsy specimen may be placed in a container with formalin (a mixture of water and formaldehyde) or some other fluid to preserve it. The tissue sample may be placed into a mold with hot paraffin wax. The wax cools to form a solid block that protects the tissue. This paraffin wax block with the embedded tissue is placed on a microtome, which cuts very thin slices of the tissue.

In certain embodiments, the tumor specimen contains less than 100 mg of tissue, or in certain embodiments, contains about 50 mg of tissue or less. The tumor specimen (or biopsy) may contain from about 20 mg to about 50 mgs of tissue, such as about 35 mg of tissue.

The tissue may be obtained, for example, as one or more (e.g., 1, 2, 3, 4, or 5) needle biopsies (e.g., using a 14-gauge needle or other suitable size). In some embodiments, the biopsy is a fine-needle aspiration in which a long, thin needle is inserted into a suspicious area and a syringe is used to draw out fluid and cells for analysis. In some embodiments, the biopsy is a core needle biopsy in which a large needle with a cutting tip is used during core needle biopsy to draw a column of tissue out of a suspicious area. In some embodiments, the biopsy is a vacuum-assisted biopsy in which a suction device increases the amount of fluid and cells that is extracted through the needle. In some embodiments, the biopsy is an image-guided biopsy in which a needle biopsy is combined with an imaging procedure, such as, for example, X ray, computerized tomography (CT), magnetic resonance imaging (MRI) or ultrasound. In other embodiments, the sample may be obtained via a device such as the MAMMOTOME® biopsy system, which is a laser guided, vacuum-assisted biopsy system for breast biopsy.

This invention is further illustrated by the following non-limiting examples.

EXAMPLES

Materials and Methods

Cell lines: Breast cancer cell (BCC) lines MDA-MB-231, T47D, MCF7/Ras, and MDA-MB-435 were cultured in Dulbecco's modified Eagle's medium (DMEM) and supplemented with 10% FBS, 100 units/mL penicillin, and 100 µg/mL streptomycin (complete media). Primary human MSCs were isolated from the bone marrow (BM) of healthy donors at the Texas A&M Health Science Center College of Medicine Institute for Regenerative Medicine (IRM) at Scott & White Hospital, and propagated. Utilized BM MSCs originated from 7 different donors, were used for experiments prior to passage 5, and delivered consistent results with one another. Adipose MSCs (adMSC) were purchased from ScienceCell Research Laboratories (Carlsbad, Calif.) and used before passage 5. WI-38 human embryonic lung fibroblasts (ATCC CCL-75) were also used before 5 passages. BM MSCs, adMSCs, and WI-38 cells were cultured in aMEM, and supplemented with 10% FBS, 1% L-glutamine, 100 units/mL penicillin, and 100 µg/mL streptomycin. All cells were maintained at 37° C. under 5% $CO_2$.

Cocultures and sorting: For direct co-cultures, BM MSCs, adMSCs, or WI-38 cells were seeded at a density of $3\times10^6$ cells in a 15 cm tissue culture plate and allowed to adhere overnight. GFP-expressing BCCs were then overlaid onto the BM MSC, adMSC or WI-38 monolayers at a density of $1\times10^6$ cells. All cells were cultured individually in parallel as controls. Following 72-hr incubation in complete DMEM, co-cultured cells were trypsinized and single-cell suspensions were separated by flow cytometry. GFP-expressing BCCs were recovered and processed as described below. For indirect co-cultures, MSCs and BCCs were grown in a Boyden chamber where the two populations were separated by a 0.4 µm porous membrane that allowed soluble factor exchange. MSCs were cultured alone or together with BCCs in the top insert in complete DMEM media, while BCCs were cultured in the bottom well for 3 days. Following incubation, BCCs seeded in the bottom chamber were lysed and RNA was extracted and used in RT-qPCR gene expression analyses as described below.

Agilent Arrays: Total RNA derived from BCCs cultured alone or sorted out of co-cultures with BM MSCs were isolated with Trizol using miRNeasy (Qiagen) following the manufacturer's protocol. RNA quality and integrity was verified using the 2100 Agilent bioanalyzer and 100 ng of triplicate samples were submitted for hybridization, scanning, and subsequent analysis. Agilent oligonucleotide microarray system (miRNA AMADID 025987, Agilent Technologies) was used to detect miRNA gene variation in MDA-MB-231 stimulated with BM MSCs compared to MDA-MB-231 cultured alone.

Q-rtPCR analysis and primers: Total RNA was extracted using miRNeasy kit (Qiagen). RNA concentrations, assessed using NanoDrop ND-1000 (Thermo Scientific), were equilibrated before reverse transcription (RT). Generally, RT was performed using 100 µg of RNA for cell-lines and 250 µg for macrodissected clinical samples with the miScript II RT kit (Qiagen). cDNA was again equilibrated for RT-qPCR runs using ~10 ng/well for detection of mature miRNAs and 100 ng/well for detection of pri-miRNAs or mRNAs. Sybr green mix was purchased from Qiagen. Miscript primer assays and universal primer (Qiagen) were utilized for detection of mature miRNAs. MiScript primer assays utilized were: Hs_miR-199a-3p_1 #MS00007602, Hs_miR-199a_1 (miR-199a-5p) #MS00006741, Hs_miR-762_1 #MS00021805, Hs_miR-1915_1 #MS00020356, Hs_miR-214_1 #MS00003822, Hs_let-7b_1 #MS00003122, Hs_miR-34a_1 #MS00003318. The miScript precursor assays utilized were: Hs_mir199a-1_1_PR #MP00001365 and Hs_mir-199a-2_1_PR #MP00001372. As reference RNA, 35 pM synthetic C. elegans miR-39 (Syn-cel-miR-39 miscript miRNA mimic #MSY0000010; Ce_miR-39_1 primer assay for detection #MS00019789, Qiagen) was added into Trizol (Qiazol) RNA lysis solutions and/or endogenous RNU5A (Hs_RNU5A_11 #MS00013993, Qiagen) was used. Primers used to detect specific pre-miRNAs miScript precursor assays were obtained from Qiagen. and were: Hs_mir199a-1_1_PR #MP00001365 and Hs_mir-199a-2_1_PR #MP00001372. The sources and sequences of additional primers used were: LOX (Hs_LOX_1_SG QT00017311, Qiagen), E-cadherin: (R) 5'-CATTCT-GATCGGTTACCGTGATC-3' (SEQ ID NO:1) and (F) 5'-AGAACGCATT GCCACATACACTC-3' (SEQ ID NO:2). N-cadherin: (R) 5'-CCGAGATGGGGTTGA-TAATG-3' (SEQ ID NO:3) and (F) 5'-ACAGTGGCCAC-CTACAAAGG-3' (SEQ ID NO:4). Vimentin: (R) 5'-GCT-TCCTGTAGGTGGCAATC-3' (SEQ ID NO:5) and (F) 5'-GAGAACTTTGCCGTTGAAGC-3' (SEQ ID NO:6). Smooth Muscle Actin: (R) 5'-GCGTCCAGAGGCATAGA-GAG-3' (SEQ ID NO:7) and (F) 5'-ACTGGGACGACATG-GAAAAG-3' (SEQ ID NO:8). STK11 (F) 5'-AGGGCCGT-CAAGATCCTC-3' (SEQ ID NO:9) and (R) 5'-ATTTTCTGCTTCTCTTCGTTGT-3' (SEQ ID NO:10). MAP3K11 (F) 5'-AACTGGGCTGTGCAGATTG-3' (SEQ ID NO:11) and (R) 5'-GTGGTTTTGTGCCACTCTC-3' (SEQ ID NO:12). IKK-beta (F) 5'-ACAGCATCCAGAC-CCTGAAG-3' (SEQ ID NO:13) and (R) 5'-GAAATC-CAACTTGGCCTTGA-3' (SEQ ID NO:14). ABCC1 (aka MRP1) (F) 5'-TTTTTACCTCTGGGCCTGTTT-3' (SEQ ID NO:15) and (R) 5'-CCCAGAAAGAGTAGAAGAG-GTCTG-3' (SEQ ID NO:16). AXL (F) 5'-GTGTCAGCTC-CAGGTTCAGG-3' (SEQ ID NO:17) and (R) 5'-TGTC-CCAGAAACACCAAACA-3' (SEQ ID NO:18). APOE (F) 5'-CGTTGCTGGTCACATTCCT-3' (SEQ ID NO:19) and (R) 5'-TCAGTTCCTGGGTGACCTG-3' (SEQ ID NO:20). DNAJA4 (F) 5'-CGGAGAGCAGGCAATTAAAG-3' (SEQ ID NO:21) and (R) 5'-GCCAATTTCTTCGTGACTCC-3' (SEQ ID NO:22). FOXP2 (F) 5'-TGCGACAGAGA-CAATAAGCAA-3' (SEQ ID NO:23) and (R) 5'-AATC-CACTTGTTTGCTGCTG-3' (SEQ ID NO:24). 18S rRNA (F) 5'-GTAACCCGTTGAACCCCATT-3' (SEQ ID NO:25) and (R) 5'-CCATCCAATCGGTAGTAGCG-3' (SEQ ID NO:26). Q-rtPCR was performed in 10 ul volumes on an 7900HT Real-Time PCR System (Applied Biosystems) with associated SDS2.4 software. Constructs: pRRL3-GFP was expressed in BCCs using lentiviral transduction in the presence of polybrene (10 µg/mL). Lentivirus was generated from co-transfection of 293T cells with (Promega), psPAX (for viral packaging), and pCMV-VSVG (for viral envelope expression) using Fugene HD transfection reagent (Roche). For stable miRNA overexpression, BCCs expressing pRRL3-GFP were transfected with pEGPmiR-Null, pEGP-miR-199a-2 (purchased from Cell Biolabs), or pcDNA3.2N5 hsa-mir-214 (Addgene plasmid #26313; Dr. D. Bartel). Stable transfectants were selected with 2 µg/mL puromycin for pEGP constructs or 1 mg/mL G418 for pcDNA3.2N5-miR-214 or both for cells expressing both miR-199a and miR-214. Selected cells were initially allowed to recover and expand in antibiotic-free media, and were subsequently maintained in selection antibiotics at 50% primary selection concentrations and used before passage 20. pEGP-miR-1915 and pEGP-miR-762 were generated by PCR amplification of precursor stem-loops (KAPA Biosystems High-fidelity PCR) from human genomic DNA and were subcloned into a miRNA Select pEGP-miR Cloning and Expression vector (Cell Biolabs) using BamHI and NheI sites. Hsa-miR-762 stem-loop GGCCCGGCUCCGG-GUCUCGGCCCGUACAGUCCGGCCGGCC AUGCUG-GCGGGGCUGGGGCCGGGGCCGAGCCCGCG-GCGGGGCC (SEQ ID NO:27) was amplified using PCR/cloning primers: Fwd: 5' TCGA-GGATCC-GTGCTGGTGGTCCCGCTGTGT 3' (SEQ ID NO:28); Rev: 5' TCGA-GCTAGC-TTGGGGACGAGA-GAGGGCGCG 3' (SEQ ID NO:29). Hsa-miR-1915 stem loop TGAGAGGCCGCACCTTGCCTTGCTGC-CCGGGCCGTGCACCCGTGGGCCCCAGGGC-GACGCGGCGGGGGCGGCCCTAGCGA (SEQ ID NO:30) was amplified using PCR/cloning primers: Fwd: 5' TCGACATATG-CAAGAAGATGCAATCGCGG 3' (SEQ ID NO:31); Rev: 5' TCGA-AAGCTTGAGAAACCACA-GAGCCTTCTC3' (SEQ ID NO:32). For expression of miR-199a-3p and miR-199a-5p, synthetic RNA duplexes were used to express singly mature miR-199a-3p or -5p: Syn-hsa-miR-199a-3p or -5p Qiagen miScript miRNA Mimics #MSY0000232 and #MSY0000231, respectively. For expression of miR-let7b-5p and miR-34a-5p, similar RNA duplexes were used from Qiagen, miscript miRNA mimics #MSY0000063 and #MSY0000255, respectively. For shRNA constructs, pLKO.1 FOXP2 shRNAs and scrambled control shRNA (shSCRAM) constructs were obtained from the Dana-Farber Cancer Institute (Boston, Mass.) through the RNAi Consortium and stably expressed in MDA-MB-231 cells by lentiviral generation, infection, and selection. Briefly, HEK-293T cells were transfected with shRNA plasmids using viral packaging and Fugene H D (Roche). The viral supernatants were collected at 48 hrs and used to infect BCCs in the presence of polybrene. Stable cell lines were generated following puromycin selection, and gene silencing was verified by RTqPCR and Western blot analysis.

Proliferation assays: Cells were plated as indicated in triplicate sets for each day of the experiment. Plates were discarded after trypsinization and cell harvest, and cells were counted by hemacytometer using the Trypan blue exclusion assay.

Western Blots: Cells were lysed in RIPA buffer (150 mM sodium chloride, 1.0% Triton X-100, 0.5% sodium deoxycholate, 0.1% sodium dodecyl sulphate/SDS, 50 mM Tris, pH 8.0) and supplemented with 1× Protease Inhibitors (Roche) and 1× Phosphatase Inhibitors (Roche). Membrane fractions were cleared by centrifugation at 20,000 rpm for 15 min at 4° C. Cleared proteins (100 µg) were separated by denaturing gel electrophoresis and transferred to Immobilon-P transfer membranes (IPVH00010; Millipore), blocked with 5% TBST/milk, and probed overnight at 4° C. with primary antibodies recognizing: N-Cadherin (Cell Signaling #4061), β-actin (Cell Signaling #4970), CD44 (Cell Signaling #3578), Met (Cell Signaling #8198), mTOR (Cell Signaling #2983), SMAD1 (Cell Signaling #6944), SMAD4 (Cell Signaling #9515), Caveolin-2 (Cell Signaling #8522), BRM (Cell Signaling #6889), GSK3β (Cell Signaling #9315), SirT1 (Cell Signaling #2493), pan-ERK (BD #610123), EZH2 (Cell Signaling #4905), PTEN (Cell Signaling #9559), FOXP2 (Cell Signaling #5337), STAT3 (Cell Signaling #4904), VCAN (Abcam #19345), β-tubulin (Cell Signaling #2128), or Vimentin (Cell Signaling #5741) antibodies according to the manufacturer's recommendations.

Transwell assays: For motility assays, cells were seeded in equal numbers in triplicates on top of an equilibrated Boyden chamber apparatus and allowed to migrate overnight through 8 µm pores (BD Biosciences) towards 10% FBS DMEM in the bottom chamber. Membranes were then fixed in 4% paraformaldehyde. The seeding section of the membrane was cleaned with a cotton swab and the bottom surface stained with bromophenol blue, washed, and imaged. Cells were counted from the resulting images.

Anoikis assays: Cancer cells were trypsinized and suspended in triplicate tubes in 0.1% FBS DMEM and continuously tumbled at 37° C. for the duration of the experiments. Viable cells were counted by hemacytometer using the Trypan blue exclusion assay.

Tumor initiation and metastasis analyses: Briefly, female athymic nude mice (Charles River Laboratories #490) were subjected to 200 µL (2:1 complete DMEM/cells:Reduced Growth Factor Matrigel; BD Biosciences) subcutaneous injections of cancer cell lines at the indicated numbers. Mice were assessed weekly for tumorigenesis via manual palpation. Tumor presence was confirmed by fluorescence microscopy following excision after 8-10 weeks of injection. Only tumors weighing >0.05 g were assimilated in the analyses. For metastasis, lungs were surgically isolated, and metastasis assessed by counting GFP-positive nodules under fluorescence microscopy. All mouse experiments were conducted in accordance with IACUC guidelines.

ALDEFLUOR Assays: ALDEFLUOR kit (StemCell technologies, Vancouver, Canada) was used to measure ALDH1 enzymatic activity in BCCs from direct co-culture with GFP-labeled MSCs. BCCs were suspended in ALDEFLUOR assay buffer containing ALDH1 substrate and incubated for ~30 min at 37° C. DEAB treatment, a specific ALDH inhibitor, served as a negative control. Stained cells were measured using FITC channel on BD-FACSaria flow cytometer with BD FACSDiva software (BD Biosciences). Analysis was performed using Flowjo software (Stanford U., Treestar Inc.).

Mammosphere assays: Equal numbers of cells were passed 3× through a 27.5 gauge syringe to ensure a single cell suspension, then plated in triplicate in 2% FBS Mammocult Human Medium (Stemcell Technologies) for 1-3 weeks. Spheres were counted under phase contrast microscopy. Subsequently, cells were dissociated with trypsin, counted, passed through an identical syringe, and replated at identical numbers as previously for 2-3 passages to characterize the growth patterns of serially passaged cells.

PCR profiling arrays: BCC-derived RNA was analyzed using Human Stem Cell PCR Array (Qiagen #PAHS-501Z), and data was analyzed using RT2 Profiler™ PCR Array Data Analysis software.

Clinical analyses: FOXP2 levels in primary tumors versus control tissues and in invasive ductal cancers versus breast tissue with benign lesions in TCGA and Chen et al. (Breast Cancer Res Treat 119, 335-346, 2010), respectively, were derived from ROCK. Breast cancer datasets GSE27011 were analyzed by retrieving the raw gene expression data, which was subsequently normalized at the gene level using robust fRMA algorithm or using the original normalization provided by the respective authors. Significance in FOXP2 expression was determined using unpaired student t-test (P value). All analyses were performed using Bioconductor Packages and R language. For specimen analysis, total RNA was extracted from cancer-cell-enriched (50-80% tumor) macrodissected tumors using miRNeasy (Qiagen) under approved Curie Institute IRB protocols. Normal control tissue originated from normal tumor margins. RT-qPCR analyses were conducted as described above. miRNA levels in in situ versus invasive ductal carcinomas were derived from Farazi et al (Farazi et al., Cancer Research, 71, 4443-4453, 2011). MiRNA levels were log 2-transformed and compared between samples using two-sided Welch's test.

EXAMPLE 1

MSC Priming Induced Specific MicroRNAs in Breast Cancer Cells

Figure 1:
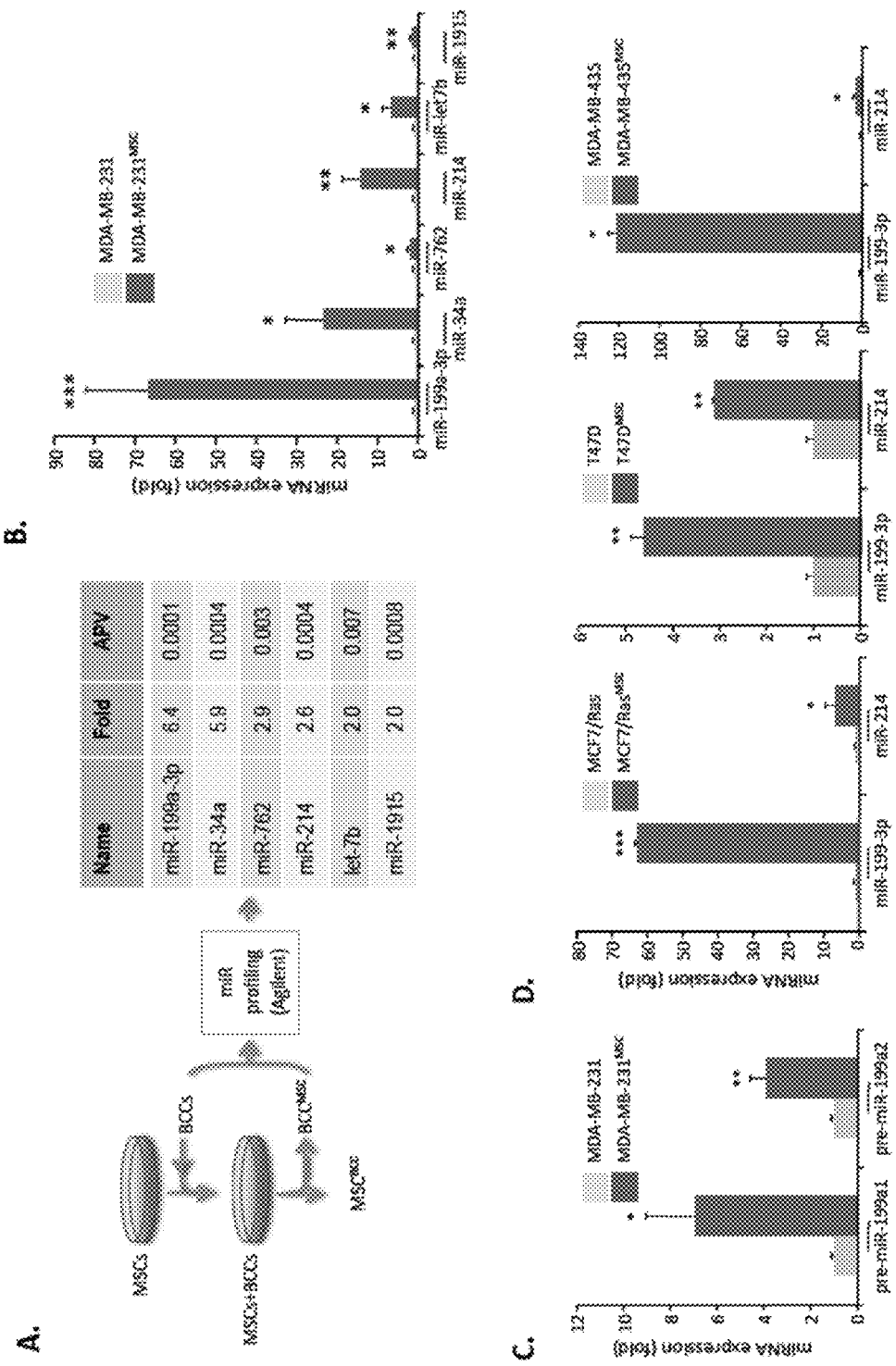
FIG. 1 shows the induction of miR-199a and miR-214 in MSC-primed breast cancer cells. Panel A shows a schematic flow chart of MSC+BCC coculture and subsequent sorting of BCCs for full transcriptome miRNA profiling (Agilent; 2010). Six mature miRNAs were found to be enriched ≥2.0 folds in MSC-activated BCCs ($BCC^{MSC}$) compared to resting BCCs and are listed with their corresponding adjusted p-values (APV). Data is representative of n=4 independent repeats. Panel B shows RT-qPCR (rtPCR-ΔΔct) validation of the identified mature miRNAs in Panel A. Panel C shows rtPCR-ΔΔct probing precursor miRNAs derived from miR-199a1 and miR-199a2 loci. Panel D shows rtPCR-ΔΔct probing miR-199a2 locus miRNAs in MSC-activated MCF7/RAS, T47D, and MDA-MB-435 cells, MCF7/$Ras^{MSC}$, $T47D^{MSC}$, and MDA-MB-$435^{MSC}$, respectively. All rtPCR-ΔΔct data are represented as mean of fold-enrichment ±SEM of n>3 independent repeats. (*)-indicates P<0.05; ()-indicates P<0.01, (*)-indicates P<0.001 in 2-tailed student's t-test. See also FIG. 2.

GFP-labeled MDA-MB-231 BCCs were cultured together with human bone-marrow-derived MSCs (1:3 ratio of BCC: MSC) for 3 days. GFP-BCCs were then isolated by fluorescence-activated cell sorting (FACS; MDA-MB-231$^{MSC}$), and their mature miRNAs profiled by subtractive miRNA arrays (Agilent) using RNA derived from resting GFP-BCCs cultured alone as control (FIG. 1, Panel A). These analyses revealed that the levels of only six miRNAs were significantly enriched ($\geq$2-fold; adjusted p-value<0.05) in MDA-MB-231$^{MSC}$ when compared to control BCCs (FIG. 1, Panel A): miR-199a-3p, -34a, -762, -214, -let7b, and -1915. Semi-quantitative real-time PCR (rtPCR-$\Delta\Delta$ct) was used to validate the microarray findings, and confirmed a multi-fold induction of these miRNAs in MSC-activated cancer cells (FIG. 1, Panel B).

miR-199a-3p levels exhibited the highest levels of enrichment in MDA-MB-231$^{MSC}$ compared to the other MSC-triggered miRs, rising more than ~65 folds over controls (FIG. 1, Panel B). Furthermore, miR-199a-3p upregulation, serve a positive role in breast cancer pathogenesis.

Figure 2:
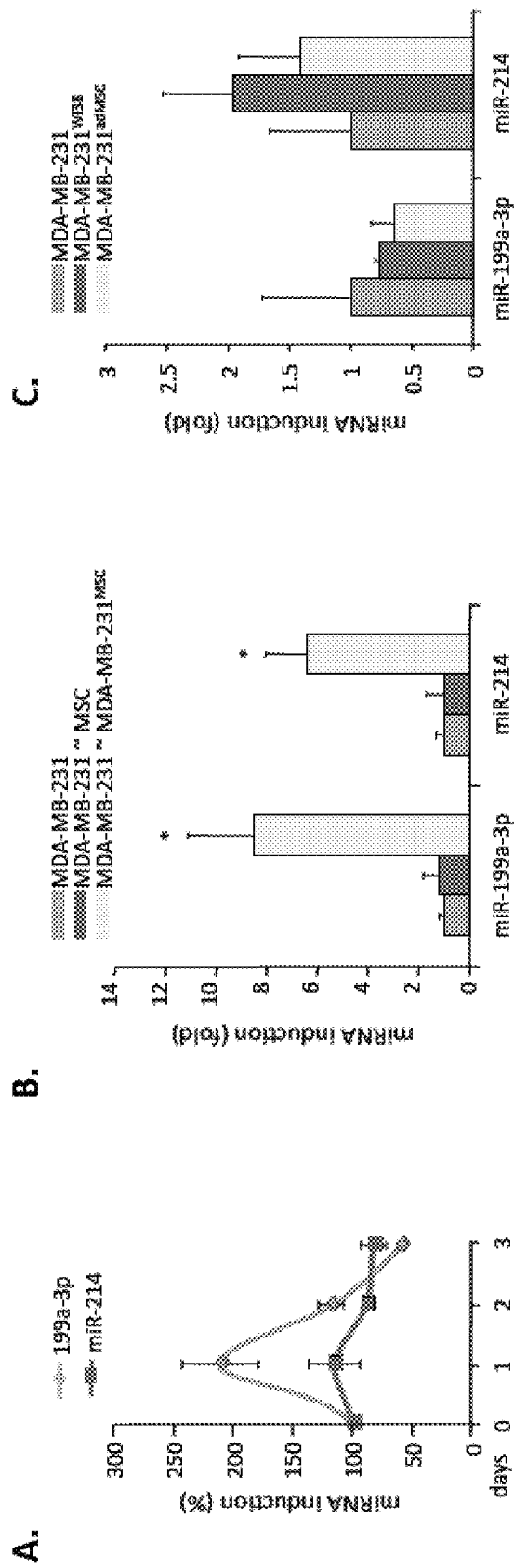
FIG. 2 shows stable and specific induction of miR-199a and miR-214 in MSC-primed breast cancer cells. Panel A shows MSC-induced A2-locus miRNAs persist for at least 3 days following separation from MSCs. rtPCR-ΔΔct of mature A2 locus miRNAs at sorting (day 0) and each day following re-culture post-sort (n=3 independent repeats). Data is represented as percentage of enrichment observed at sorting day ±SEM. Panel B shows robust miRNA induction requires MSC-BCC contact. rtPCR-ΔΔct probing mature miRNA levels following 3-day Boyden chamber assays (0.4 um pores) (n=3 independent repeats). rtPCR-ΔΔct data is represented as mean fold-enrichment over levels observed in MDA-MB-231 controls ±SEM. Panel C shows rtPCR-ΔΔct probing mature miR-199a-3p or miR-214 levels following co-culture/sorting from W138 embryonic fibroblasts or adipose tissue-derived MSCs (n=3 independent repeats). (*)-indicates P<0.05; 2-tailed student's t-test.

The MDA-MB-231MSC population was observed to continue to produce high levels of miR-199a-3p even after separation from MSCs (FIG. 2, Panel A), suggesting that its induction was sustained and transcriptional in nature. In this regard, miR-199a-3p is derived from two separate genomic loci in humans: one located at chromosome 19, and the other on chromosome 1; comprising the miR-199a1 (A1) and miR-199a2 (A2) loci, respectively. The relative contributions of A1 or A2 to the levels of mature miR-199a-3p present in MDA-MB-231$^{MSC}$ were determined by assessing the levels of the distinct locus-specific miRNA precursor stemloops (pri-miRs) using rtPCR-$\Delta\Delta$ct. These experiments revealed that both pri-miR-199a1 and pri-miR-199a2 were significantly increased in MDA-MB-231$^{MSC}$, with a slightly elevated contribution of A1 (~60%) compared to A2 (~40%) (FIG. 1, Panel C). miR-199a2 shares a common promoter with miR-214, which was similarly identified in the profiling array as induced by ~15-fold in MDA-MB-231$^{MSC}$ (FIG. 1, Panels A and B), and likewise maintained elevated levels three days after separation from MSCs (FIG. 2, Panel A). Both miR-199a-3p and miR-214 were found to be elevated following MSC-stimulation of other BCC lines, such as MCF7/Ras, T47D, and MDA-MB-435 (FIG. 1, Panel D). Together, without wishing to be bound by theory, these observations suggested that A1/A2 miRNA activation is a generalized element of the BCC response to MSC stimulation, and insinuated a potential functional cooperation between miR-199a-3p and miR-214. Of note was that robust induction of miR-199a-3p and miR-214 by bone-marrow-derived MSCs required cell-cell contact between BCCs and MSCs (FIG. 2, Panel B), and did not occur upon contact of BCCs with other phenotypically similar mesenchymal cells, such as human adipose-derived MSCs (adMSCs) or WI-38 embryonic fibroblasts (FIG. 2, Panel C). Without wishing to be bound by theory, these results implied that bone-derived MSCs are unique in their ability to trigger A1/A2 locus miRs, and indicated that these miRNAs play functional roles in breast cancer malignancy.

EXAMPLE 2

MiR-199a and MiR-214 Promotes Metastasis and Cancer Stem Cell Phenotypes

It could not be ruled out that certain BCCs within the total population expressed both miR-199a-3p and miR-214 (e.g., in the case where both loci, or the A2 locus alone is active), while others expressed only miR-199a-3p (e.g., if the A1 locus alone is active). Accordingly, both possibilities were modelled, stably over expressing exogenous miR-199a, or both miR-199a and miR-214 in MDA-MB-231 cells (BCC$^{199a}$ and BCC$^{199a/214}$, respectively). The expression levels of the respective miRNAs in BCC$^{199a}$ and BCC$^{199a/214}$, verified by rtPCR-$\Delta\Delta$ct and compared to control counterparts harboring an empty vector (BCC$^{null}$), showed >40-fold and >3-fold upregulation in miR-199a-3p and miR-214 levels, respectively (FIG. 4, Panel A).

Figure 3:
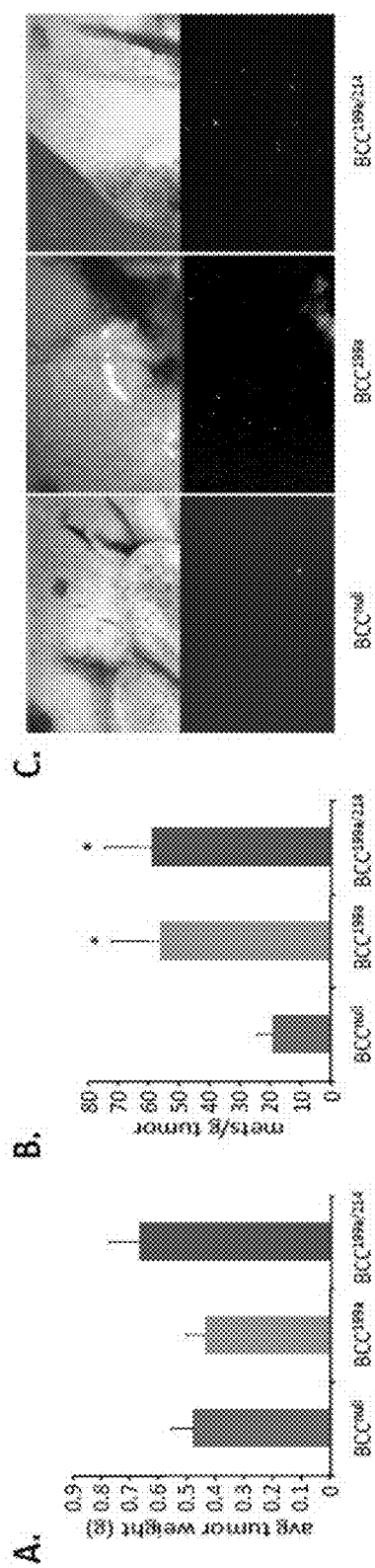
FIG. 3 shows miR 199a and miR-214 expression causes propagation of cancer stem cell traits and metastasis. Panel A shows mean weights (gram) ±SEM of tumors from the indicated groups isolated at matched time points from athymic Nude mice 8-14 weeks after subcutaneous implantation of equivalent numbers of $BCC^{null}$, $BCC^{199a}$, or $BCC^{199a/214}$ (n=77, 53 and 81 mice, respectively). Panel B shows mean number of GFP-positive lung metastases ±SEM observed per gram of primary tumor burden in each mouse (metastatic index; n=37, 27, and 37 mice for $BCC^{null}$, $BCC^{199a}$, and $BCC^{199a/214}$, respectively. Panel C shows representative images of GFP+ colonies in the lungs of mice in B visualized under light (upper panels) or fluorescence microscopy (lower panels). Panel D shows minimal serum tumbling assay. Left: Mean numbers of viable cells in suspension ±SEM, as determined by trypan exclusion assays. Right.
Figure 3:
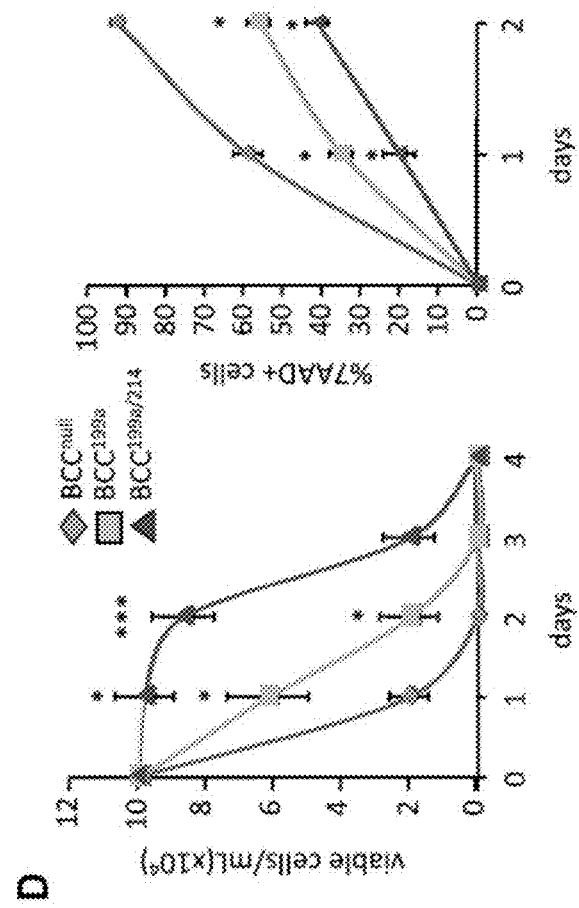
Figure 3:
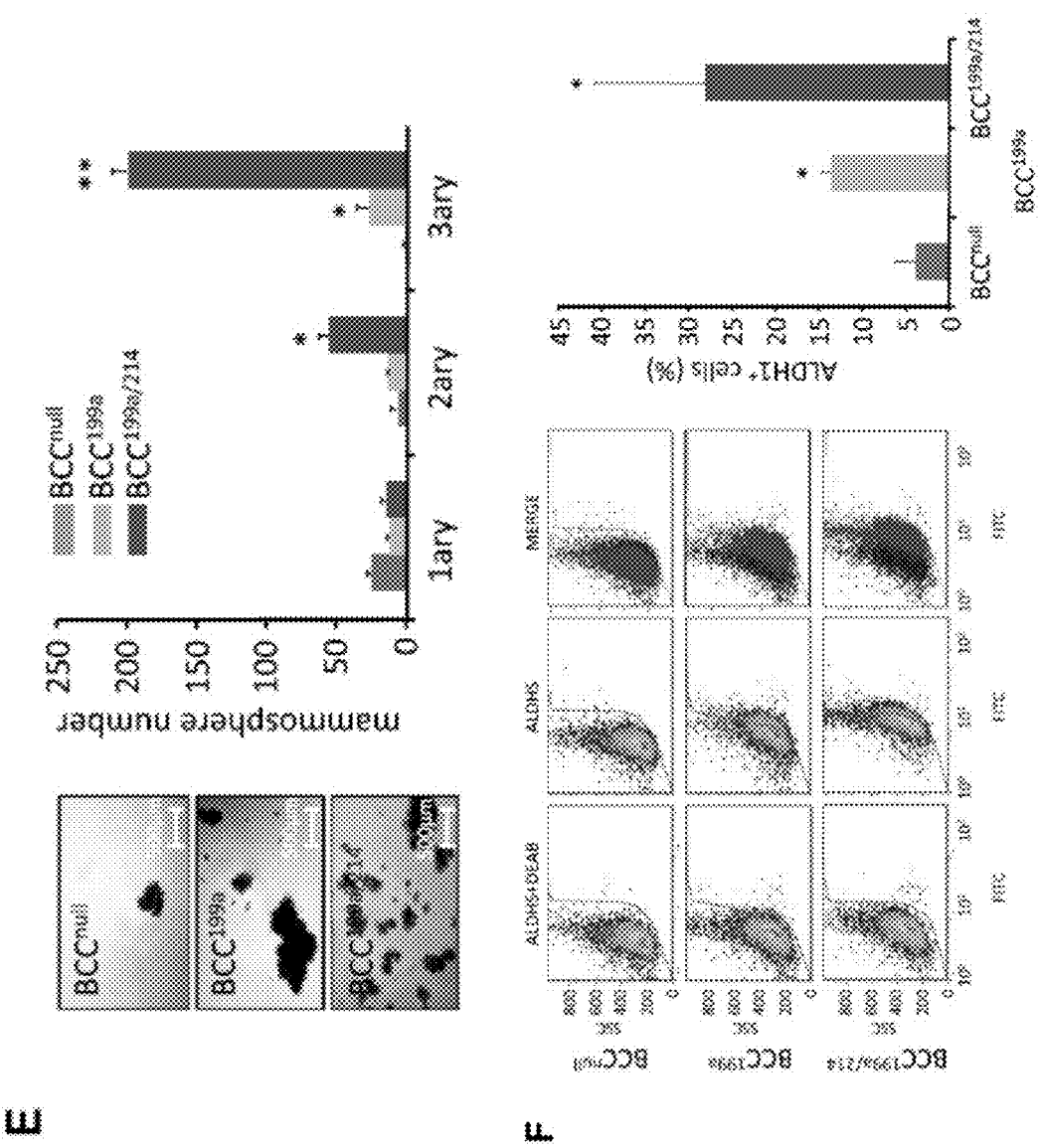
Figure 3:
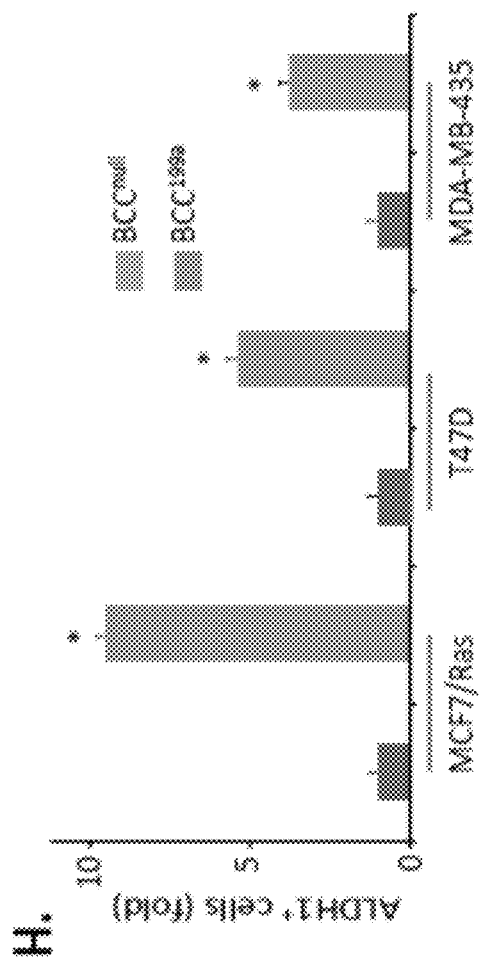

The malignant potential of BCC$^{199a}$ and BCC$^{199a/214}$ were explored by examining their tumorigenic and metastatic abilities compared to BCC$^{null}$. Equal numbers of cells of each group were implanted subcutaneously into athymic Nude mice, and allowed to form tumors for 10-14 weeks. While BCC$^{199a}$- and BCC$^{199a/214}$-tumors did not differ from BCC$^{null}$-tumors in average weight at the time of tissue harvest (~0.5-0.65 g; FIG. 3, Panel A), analysis of GFP-positive BCC colonies in the lungs of the respective animals revealed that mice implanted with either BCC$^{199a}$ or BCC$^{199a/214}$ had more than double the average of lung metastases per gram of tumor as compared with BCC$^{null}$ controls (FIG. 3, Panels B and C). These experiments demonstrated an enhanced malignancy of BCC$^{199a}$ and BCC$^{199a/214}$ in vivo.

BCC$^{199a}$ and BCC$^{199a/214}$ exhibited no proliferative advantage over their control counterparts in 2D-culture conditions (FIG. 4, Panel B). Furthermore, these cells did not display increased expression of mesenchymal markers, such as vimentin, N-cadherin, smooth muscle actin or lysyl oxidase (LOX) at the mRNA and/or protein levels, and actually exhibited some resurgence of E-cadherin mRNA (FIG. 4, Panels C and D). BCC$^{199a}$ and BCC$^{199a/214}$ manifested ~50% reduced intrinsic motility compared to BCC$^{null}$ in Boyden chamber motility assays (FIG. 4, Panel E). Without wishing to be bound by theory, these observations suggested that the increased metastasis observed in BCC$^{199a}$ and BCC$^{199a/214}$ was manifested through pathways distinct from those governing proliferation, invasion, and motility.

CSCs are characterized by their unique capacity for tumor initiation, as disseminated cancer cells must possess the ability to engender new growths at distant sites. In support of this notion, highly metastatic BCC$^{MSC}$ was observed to exhibit increased tumorigenic properties in limiting dilution tumor-initiation analyses, forming subcutaneous tumors in Nude mice ~2.5-times more frequently than controls, with as little as 100 cells per injection (FIG. 4, Panel F).

BCC$^{199a}$ and BCC$^{199a/214}$ displayed enhanced resistance to suspension-induced cell death, exhibiting ~50% survival after 48 hours in a minimal serum tumbling assay, and a corresponding $\geq$50% reduction in their apoptosis rates as measured by 7-aminoactinomycin D (7AAD) (FIG. 3, Panel D), and an increased ability to grow in low-attachment mammosphere growth conditions after serial passage (FIG. 3, Panel E). BCC$^{199a}$ and BCC$^{199a/214}$ also showed ~3- and ~7-fold increases in their ALDH1-positive populations, respectively, as assessed by ALDEFLUOR-based FACS assays (FIG. 3, Panel F). Finally, BCC$^{199a}$ and BCC$^{199a/214}$ possessed markedly enhanced tumor-initiating capabilities in limiting-dilution tumor assays in athymic Nude mice, forming tumors at 100 cells per injection at ~2-3 times the rate of their BCC$^{null}$ controls (FIG. 3, Panel G). Without wishing to be bound by theory, these observations suggested that the enhanced metastasis of BCC$^{199a}$ and BCC$^{199a/214}$ correlated with their increased CSC phenotypes.

The characteristics of BCC$^{199a}$ were observed to be similar or identical to BCC$^{199a/214}$, aside from some moderate accentuation of some CSC traits in BCC$^{199a/214}$, suggesting that the malignancy of BCC$^{199a/214}$ rested largely on the actions of miR-199a. Individual RNA duplexes were transfected—offset to allow generation of only a specific single mature miRNA—coding for either 199a-3p or 199a-5p, into MDA-MB-231 cells. While transient expression of 199a-3p caused a ~2.5-fold increase in ALDH1-positivity, 199a-5p expression did not (FIG. 4, Panel G), despite the substantial expression levels of 199a-5p in these cells (FIG. 4, Panel H). Without wishing to be bound by theory, this suggested that miR-199a-3p was the critical miRNA produced from miR-199a affecting CSC propagation. Stable expression of miR-199a in other breast cancer cell lines, such as MCF7/Ras, T47D or MDA-MB-435 cells, similarly led to ~10-, ~6-, and ~4-fold increases in their ALDH1-positivity, respectively, suggesting that the ability of miR-199a-3p to regulate CSC phenotypes was not idiosyncratic of MDA-MB-231 cells, and was generalized (FIG. 3, Panel H).

EXAMPLE 3

Downregulation of the Speech Gene FOXP2, Observed in BCC$^{199a}$ and BCC$^{199a/214}$, Promotes Cancer Stem Cell Traits and Metastasis BCC$^{199a}$ and BCC$^{199a/214}$ were probed for the expression levels of published targets for miR-199a-3p (or miR-214), such as hepatocyte growth factor receptor/MET, signal transducer and activator of transcription-3/STAT3, mammalian target of rapamycin/mTOR, phosphatase and tensin homolog/PTEN, caveolin-2/CAV2, extracellular-signal-regulated kinases/ERK, histone-lysine Nmethyltransferase EZH2, small mothers against decapentaplegic protein-4/SMAD4, versicanNCAN, SMAD1, brahma/BRM, NAD-dependent deacetylase sirtuin-1/SIRT1, CD44, glycogen synthase kinase 3-beta/GSK3β, serine/threonine kinase-11/STK11, mitogen activated protein kinase kinase kinase-11/MAP3K11, IκB kinase-β/IKKβ, multidrug resistance protein-1/MRP1, UFO tyrosine kinase homolog/Axl, as well as apolipoprotein E/ApoE and the heatshock protein-40 homolog DNAJA4. No concerted downregulation of any of these published targets were detected in both BCC$^{199a}$ and BCC$^{199a/214}$ as compared to BCC$^{null}$ (FIG. 6, Panels A and B), underscoring the importance of cellular context in determining miRNA functions. Exceptions were noted, however, for SMAD1, MAP3K11, and IKKβ (FIG. 6, Panels A and B), which were downregulated in BCC$^{199a}$ but not BCC$^{199a/214}$.

Array-based approaches were utilized to identify potential miRNA effectors in BCC$^{199a}$ and BCC$^{199a/214}$, focusing upon those that have been correlated with the acquisition or maintenance of stem-like properties. A targeted rtPCR-ΔΔct array screen of 84 genes associated with stem cell maintenance or differentiation (Qiagen) was conducted, evaluating the relative mRNA levels of these candidates in BCC$^{199a}$ and BCC$^{199a/214}$ as compared to BCC$^{null}$. These analyses identified a number of stem-cell-associated genes that were significantly upregulated in BCC$^{199a}$ and/or BCC$^{199a/214}$, including GATA-binding protein-6/GATA6, lin-28 homolog B/Lin28B, human homeobox protein HOXC9, and the Msh homeobox MSX2. Only FOXP2 was found to be significantly (≥2-fold; p<0.005) downregulated in both cell types, exhibiting 7- and 12-fold reductions in its expression levels in BCC$^{199a}$ and BCC$^{199a/214}$, respectively (FIG. 6, Panel B).

The array finding regarding FOXP2 using independent rtPCR-ΔΔct analyses was validated (FIG. 5, Panel A), and its protein levels were observed to be severely repressed in both BCC$^{199a}$ and BCC$^{199a/214}$ (FIG. 5, Panel B), as well as in BCCMSC (FIG. 5, Panel C). FOXP2 levels were probed in the FACS-enriched ALDH1-positive fractions of MDA-MB-231$^{MSC}$. ALDH1-positive cells, which possess tumor-initiating capacities (forming 60% tumors at 10,000 cells per injection compared to their ALDH1-negative counterparts; FIG. 6, Panel C), exhibited >95% reduction in their FOXP2 content (FIG. 5, Panel D). Furthermore, expression of miR-199a in T47D cells, which enhanced their ALDH1-positivity by ~6 folds (FIG. 3, Panel H), also displayed downregulation of FOXP2 (FIG. 5, Panel E). Without wishing to be bound by theory, these findings correlated FOXP2 down-regulation with the propagation of CSCs.

Eight different retroviral plasmids expressing various short-hairpin RNAs designed for knockdown of FOXP2 (shFOXP2) were stably expressed in MDA-MB-231 cells (BCC$^{shFOXP2}$). The functionality of each hairpin was verified by Western blot analyses, and revealed two efficient hairpins, shFOXP2-1.5 and shFOXP2-2.2, that precipitated an ~70% reduction of FOXP2 protein levels (FIG. 7, Panel A). When probed with ALDEFLUOR, BCC$^{shFOXP2-1.5}$ and BCC$^{shFOXP2-2.2}$ exhibited significant >40- and >100-fold respective upregulation in their ALDH1-positivity compared to control cells expressing a scrambled hairpin control (BCC$^{shSCRAM}$; FIG. 7, Panel B). ShFOXP2 expression enhanced the ability of MDA-MB-231 cells to form mammosphere colonies in suspension by an average of ~2.5 folds (FIG. 7, Panel C), and provided cancer cells with enhanced abilities to resist anoikis (FIG. 8, Panel A). BCC$^{shFOXP2-2.2}$ initiated subcutaneous tumors in athymic Nude mice at a frequency of 28% and with as little as 100 cells per injection, a dilution prohibitive for tumor initiation by BCC$^{shSCRAM}$ (FIG. 7, Panel D). In addition to increases in their ALDH1 positivity, shFOXP2 expressing cells also exhibited increases in OCT4 and c-Myc expression (FIG. 7, Panel H). Without wishing to be bound by theory, these results indicated that FOXP2 inhibition produced cells with in vitro phenotypes consistent with those of cancer stem cells.

Mirroring the phenotypes of BCC$^{199a/214}$, BCC$^{shFOXP2}$ did not exhibit enhanced proliferation in vitro (FIG. 8, Panel B), or enhanced tumor growth in vivo (FIG. 7, Panel E). However, mice bearing BCC$^{shFOXP2}$-tumors exhibited ~9-fold increase in the numbers of metastatic lung foci per gram of primary tumor as compared to controls bearing BCC$^{shSCRAM}$-derived tumors (FIG. 7, Panels F and G). Without wishing to be bound by theory, these results demonstrated that FOXP2 inhibition was sufficient to promote the propagation of CSC phenotypes in BCCs, consistent with an observed marked enhancement of metastasis in mice.

EXAMPLE 4

FOXP2 is a Common Target of a Converging and Interrelated Set of MSC-Regulated miRNAs The proximal (~1 kb) FOXP2 3'UTR was analyzed for consensus miRNA seed sites with in silico miRNA target prediction algorithms, such as RNAhybrid, miRWalk, Targetscan, and Pictar. However, a strong consensus seed site for microRNA-199a was not found (predicted free energy cutoff ≤25 kcal/mol). These approaches did reveal putative target sites for each of the other miRNAs induced in BCCMSC, such as miRs let7b, 34a, 762, and 1915 (FIG. 9, Panels A and B). The capability of each MSC-induced miRNA was tested in repressing FOXP2. Stable expression of miR-762 or miR-1915, or transient expression of miRNA mimics for let7b or miR-34a (FIG. 10, Panel A), brought about a reduction of FOXP2 in MDA-MB-231 cells (FIG. 9, Panels C and D). Consistent with FOXP2 downregulation, these cells exhibited an increase in ALDH1-positivity as determined by ALDEFLUOR assays, displaying ~20-, ~75-, ~30-, and ~30-fold increases by let-7b, miR-34a, miR-762, and miR-1915, respectively (FIG. 9, Panel E).

The expression levels of miR-762, miR-1915, let7b, and miR-34a were elevated ~5, ~4.5, ~7, and ~4.5 folds in $BCC^{199a/214}$, respectively (FIG. 9, Panel F), suggesting the existence of an operational crosstalk between MSC-induced miRNAs in BCCs. These results were consistent with a functional cooperation between members of an interrelated regulatory network of miRs, led by miR-199a, which converge to inhibit the expression of FOXP2 (FIG. 9, Panel G). In addition, expression levels of miR-199a-3p in clinical breast cancer specimens correlated with the expression levels of miR-let-7b, miR-34a, and miR-1915 (FIG. 9, panel I). Further, high concerted expression levels of miR-199a-3p, miR-let-7b, miR-34a, and miR-1915 were indicative of overall poorer survival in breast cancer patients as assessed by Kaplan-Meier analyses (FIG. 9, panel H), indicating that the described miR network represents a significant prognostic indicator in clinical breast cancer.

EXAMPLE 5

FOXP2 Downregulation and MiR-199a-3p Upregulation Were Features of Clinical Breast Cancer Progression The recently published breast cancer sequencing data made available by The Cancer Genome Atlas Network (TCGA, 2012) was examined. and FOXP2 was determined to be downregulated ~4 folds in primary breast tumors as compared to normal tissues (FIG. 11, Panel A). In addition, FOXP2 levels were repressed ~2 folds in invasive breast carcinomas (IDCs) as compared to benign lesions (FIG. 11, Panel B; (Chen et al., Breast Cancer Res Treat 119, 335-346, 2010)), including the highly aggressive triple-negative basal-like subgroups (FIG. 11, Panel C; (Dedeurwaerder et al., EMBO Mol Med 3, 726-741, 2011)). These results were mirrored by the rtPCR-ΔΔct analysis on RNA derived from macrodissected basal-like breast cancers, in which ~80% FOXP2 repression was observed in these tumor samples (n=12) compared to RNA derived from normal tissues (n=5; FIG. 11, Panel D). To explore whether FOXP2 depression is associated with particular breast cancer subtypes, publicly available luminal A, luminal B, HER2-enriched, and basal-like breast tumor expression data sets were examined. These analysis revealed FOXP2 downregulation as a common feature of all these subtypes (FIG. 11, Panel E) and were mirrored by the rtPCR-ΔΔct analysis on RNA derived from macrodissected breast cancers, in which ~80% FOXP2 repression was observed in these tumor samples (n=74) compared to RNA derived from normal tissues (n=5; FIG. 11, Panel F)

Similarly, miR-199a-3p levels were observed to be elevated in IDCs compared to in situ ductal cancers (FIG. 11, Panel G; (Farazi et al., Cancer Research, 71, 4443-4453, 2011; Volinia et al., PNAS, 109, 3024-3029, 2012)). Without wishing to be bound by theory, these observations suggested that deregulation of FOXP2 and miR-199a-3p were common features of breast cancer progression, and elucidated the roles for these novel players in breast cancer pathogenesis. Within IDC, miR-199a-3p levels correlated with disease progression and associated significantly with lymph node positivity (N1 or N2) in a study of more than 600 breast cancer patients (FIG. 11, Panel H). In addition, miR-199a-3p levels were significantly elevated in primary tumors of patients who exhibited relapse (FIG. 11, Panel I), and also correlated with decreased patient survival over 5- and 10-year intervals (FIG. 11, Panel J). Altogether these data indicate that deregulations of FOXP2 and miR-199a-3p are common features of breast cancer progression.

EXAMPLE 6

FOXP2 Downregulation is a Feature of a Variety of Cancers

FIG. 12 shows FOXP2 expression levels in a variety of cancerous and normal tissues. A GeneChip® Human Genome U133 Plus 2.0 Array (Affymetrix) was used to evaluate FOXP2 expression levels in normal (N) and cancer (C) samples. Cancer versus normal, across a variety of tissue types, involves a downregulation of FOXP2.

Further, in light of these findings, the inventors conducted a series of retrospective Kaplan Meier survival analyses and showed that FOXP2 downregulation is associated with poor patient survival when compared to patients with elevated FOXP2 tumor levels. FIG. 13, Panels A-D show that low FOXP2 expression predicts poor patient survival, as is seen from a re-analysis of expression data. Samples were stratified based on FOXP2 expression (probe in the indicated studies, using lower-quartile of expression values of a FOXP2 probe to split selected samples). Top lines denote low-expression samples, and bottom lines denote high-expression values.

Additionally, inhibition of FOXP2 upregulates a series of proteins in cells, including c-myc, YB1, FOXO1, BRM, OCT-4, and POSTN. FIG. 14 shows that low FOXP2 expression is associated with increases in stem-cell-associated genes. Western blot analyses on lysates derived from MDA-MB-231 cells (panels a-d) or T47D breast cancer cells (panel f) expressing control (shscram) or shRNAs against FOXP2. Panel e shows RTPCR analysis on OCT-4 in the indicated control and shFOXP2 cells. Patients whose tumors exhibit elevated expression of these proteins may benefit from FOXP2- and/or miR-directed therapies.

DEFINITIONS

The following definitions are used in connection with the invention disclosed herein. Unless defined otherwise, all technical and scientific terms used herein have the same meaning as commonly understood to one of skill in the art to which this invention belongs.

As used herein, "a," "an," or "the" can mean one or more than one.

Further, the term "about" when used in connection with a referenced numeric indication means the referenced numeric indication plus or minus up to 10% of that referenced numeric indication. For example, the language "about 50" covers the range of 45 to 55.

An "effective amount," when used in connection with medical uses is an amount that is effective for providing a measurable treatment, prevention, or reduction in the rate of pathogenesis of a disease of interest.

As referred to herein, all compositional percentages are by weight of the total composition, unless otherwise specified. As used herein, the word "include," and its variants, is intended to be non-limiting, such that recitation of items in a list is not to the exclusion of other like items that may also be useful in the compositions and methods of this technology. Similarly, the terms "can" and "may" and their variants are intended to be non-limiting, such that recitation that an embodiment can or may comprise certain elements or features does not exclude other embodiments of the present technology that do not contain those elements or features.

Although the open-ended term "comprising," as a synonym of terms such as including, containing, or having, is used herein to describe and claim the invention, the present invention, or embodiments thereof, may alternatively be described using alternative terms such as "consisting of" or "consisting essentially of."

As used herein, the words "preferred" and "preferably" refer to embodiments of the technology that afford certain benefits, under certain circumstances. However, other embodiments may also be preferred, under the same or other circumstances. Furthermore, the recitation of one or more preferred embodiments does not imply that other embodiments are not useful, and is not intended to exclude other embodiments from the scope of the technology.

The amount of compositions described herein needed for achieving a therapeutic effect may be determined empirically in accordance with conventional procedures for the particular purpose. Generally, for administering therapeutic agents for therapeutic purposes, the therapeutic agents are given at a pharmacologically effective dose. A "pharmacologically effective amount," "pharmacologically effective dose," "therapeutically effective amount," or "effective amount" refers to an amount sufficient to produce the desired physiological effect or amount capable of achieving the desired result, particularly for treating the disorder or disease. An effective amount as used herein would include an amount sufficient to, for example, delay the development of a symptom of the disorder or disease, alter the course of a symptom of the disorder or disease (e.g., slow the progression of a symptom of the disease), reduce or eliminate one or more symptoms or manifestations of the disorder or disease, and reverse a symptom of a disorder or disease. For example, administration of therapeutic agents to a patient suffering from an aggressive cancer provides a therapeutic benefit not only when the underlying condition is eradicated or ameliorated, but also when the patient reports a decrease in the severity or duration of the symptoms associated with the disease. Therapeutic benefit also includes halting or slowing the progression of the underlying disease or disorder, regardless of whether improvement is realized.

Effective amounts, toxicity, and therapeutic efficacy can be determined by standard pharmaceutical procedures in cell cultures or experimental animals, e.g., for determining the LD50 (the dose lethal to about 50% of the population) and the ED50 (the dose therapeutically effective in about 50% of the population). The dosage can vary depending upon the dosage form employed and the route of administration utilized. The dose ratio between toxic and therapeutic effects is the therapeutic index and can be expressed as the ratio LD50/ED50. In some embodiments, compositions and methods that exhibit large therapeutic indices are preferred. A therapeutically effective dose can be estimated initially from in vitro assays, including, for example, cell culture assays. Also, a dose can be formulated in animal models to achieve a circulating plasma concentration range that includes the IC50 as determined in cell culture, or in an appropriate animal model. Levels of the described compositions in plasma can be measured, for example, by high performance liquid chromatography. The effects of any particular dosage can be monitored by a suitable bioassay. The dosage can be determined by a physician and adjusted, as necessary, to suit observed effects of the treatment.

In certain embodiments, the effect will result in a quantifiable change of at least about 10%, at least about 20%, at least about 30%, at least about 50%, at least about 70%, or at least about 90%. In some embodiments, the effect will result in a quantifiable change of about 10%, about 20%, about 30%, about 50%, about 70%, or even about 90% or more. In certain embodiments, the effect will result in a quantifiable change of two-fold, or three-fold, or four-fold, or five-fold, or ten-fold. Therapeutic benefit also includes halting or slowing the progression of the underlying disease or disorder or reduction in toxicity, regardless of whether improvement is realized.

EQUIVALENTS

While the invention has been described in connection with specific embodiments thereof, it will be understood that it is capable of further modifications and this application is intended to cover any variations, uses, or adaptations of the invention following, in general, the principles of the invention and including such departures from the present disclosure as come within known or customary practice within the art to which the invention pertains and as may be applied to the essential features herein set forth and as follows in the scope of the appended claims.

Those skilled in the art will recognize, or be able to ascertain, using no more than routine experimentation, numerous equivalents to the specific embodiments described specifically herein. Such equivalents are intended to be encompassed in the scope of the following claims.

INCORPORATION BY REFERENCE

All patents and publications referenced herein are hereby incorporated by reference in their entireties.

The publications discussed herein are provided solely for their disclosure prior to the filing date of the present application. Nothing herein is to be construed as an admission that the present invention is not entitled to antedate such publication by virtue of prior invention.

As used herein, all headings are simply for organization and are not intended to limit the disclosure in any manner. The content of any individual section may be equally applicable to all sections.

What is claimed is:

1. A method for reducing breast cancer metastasis, comprising administering a micro-RNA inhibitor of miR-199a to a subject in need thereof.

2. The method of claim 1, wherein the cancer is characterized by having reduced levels or activity of forkhead box protein P2 (FOXP2), relative to a less aggressive cancerous or a non-cancerous state.

3. The method of claim 1, wherein the breast cancer is characterized by the presence or absence of one or more of estrogen receptor (ER), progesterone receptor (PR), HER2, androgen receptor (AR), and prolactin receptor (PRLr).

4. The method of claim 3, wherein the breast cancer is triple negative.

5. The method of claim 1, wherein the micro-RNA inhibitor is an antisense oligonucleotide.

6. The method of claim 1, wherein expression and/or activity of miR-199a is reduced in the subject following administration of the micro-RNA inhibitor.

7. The method of claim 5, wherein the micro-RNA inhibitor is an antisense oligonucleotide comprising a sequence that is at least partially complementary to a mature sequence of miR-199a.

8. The method of claim 1, wherein the micro-RNA inhibitor is chemically modified.

9. The method of claim 8, wherein the chemical modification is selected from locked nucleic acid (LNA), phosphorothioate, 2'-O-Methyl, 2'-O-Methoxyethyl, 2'-O-alkyl-RNA unit, 2'-OMe-RNA unit, 2'-amino-DNA unit, 2'-fluoro-DNA unit, peptide nucleic acid (PNA) unit, hexitol nucleic acids (HNA) unit, INA unit, and a 2'-O-(2-Methoxyethyl)-RNA (2' MOE RNA) unit.

10. The method of claim 5, wherein the antisense oligonucleotide comprises 16 or fewer nucleotides.

11. The method of claim 2, wherein the inhibitor of miR-199a prevents or diminishes a downregulation of FOXP2.

12. The method of claim 2, wherein expression and/or activity of FOXP2 is not reduced in the subject following administration of the inhibitor.

13. The method of claim 2, wherein the treatment restores FOXP2 gene regulatory activity to pre-cancerous levels.

14. The method of claim 1, wherein the method reduces metastasis to the lungs.

* * * * *

SEQUENCE LISTING

<160> NUMBER OF SEQ ID NOS: 32

<210> SEQ ID NO 1
<211> LENGTH: 23
<212> TYPE: DNA
<213> ORGANISM: Artificial sequence
<220> FEATURE:
<223> OTHER INFORMATION: Synthetic Primer

<400> SEQUENCE: 1
cattctgatc ggttaccgtg atc                          23

<210> SEQ ID NO 2
<211> LENGTH: 23
<212> TYPE: DNA
<213> ORGANISM: Artificial sequence
<220> FEATURE:
<223> OTHER INFORMATION: Synthetic Primer

<400> SEQUENCE: 2
agaacgcatt gccacataca ctc                          23

<210> SEQ ID NO 3
<211> LENGTH: 20
<212> TYPE: DNA
<213> ORGANISM: Artificial sequence
<220> FEATURE:
<223> OTHER INFORMATION: Synthetic Primer

<400> SEQUENCE: 3
ccgagatggg gttgataatg                              20

<210> SEQ ID NO 4
<211> LENGTH: 20
<212> TYPE: DNA
<213> ORGANISM: Artificial sequence
<220> FEATURE:
<223> OTHER INFORMATION: Synthetic Primer

<400> SEQUENCE: 4
acagtggcca cctacaaagg                              20

<210> SEQ ID NO 5
<211> LENGTH: 20
<212> TYPE: DNA
<213> ORGANISM: Artificial sequence
<220> FEATURE:
<223> OTHER INFORMATION: Synthetic Primer

<400> SEQUENCE: 5
gcttcctgta ggtggcaatc                              20

<210> SEQ ID NO 6
<211> LENGTH: 20
<212> TYPE: DNA
<213> ORGANISM: Artificial sequence
<220> FEATURE:
<223> OTHER INFORMATION: Synthetic Primer

<400> SEQUENCE: 6
gagaactttg ccgttgaagc                              20

<210> SEQ ID NO 7
<211> LENGTH: 20
<212> TYPE: DNA
<213> ORGANISM: Artificial sequence -continued

```
<220> FEATURE:
<223> OTHER INFORMATION: Synthetic Primer

<400> SEQUENCE: 7
gcgtccagag gcatagagag                                                 20

<210> SEQ ID NO 8
<211> LENGTH: 20
<212> TYPE: DNA
<213> ORGANISM: Artificial sequence
<220> FEATURE:
<223> OTHER INFORMATION: Synthetic Primer

<400> SEQUENCE: 8
actgggacga catggaaaag                                                 20

<210> SEQ ID NO 9
<211> LENGTH: 18
<212> TYPE: DNA
<213> ORGANISM: Artificial sequence
<220> FEATURE:
<223> OTHER INFORMATION: Synthetic Primer

<400> SEQUENCE: 9
agggccgtca agatcctc                                                   18

<210> SEQ ID NO 10
<211> LENGTH: 22
<212> TYPE: DNA
<213> ORGANISM: Artificial sequence
<220> FEATURE:
<223> OTHER INFORMATION: Synthetic Primer

<400> SEQUENCE: 10
attttctgct tctcttcgtt gt                                              22

<210> SEQ ID NO 11
<211> LENGTH: 19
<212> TYPE: DNA
<213> ORGANISM: Artificial sequence
<220> FEATURE:
<223> OTHER INFORMATION: Synthetic Primer

<400> SEQUENCE: 11
aactgggctg tgcagattg                                                  19

<210> SEQ ID NO 12
<211> LENGTH: 19
<212> TYPE: DNA
<213> ORGANISM: Artificial sequence
<220> FEATURE:
<223> OTHER INFORMATION: Synthetic Primer

<400> SEQUENCE: 12
gtggttttgt gccactctc                                                  19

<210> SEQ ID NO 13
<211> LENGTH: 20
<212> TYPE: DNA
<213> ORGANISM: Artificial sequence
<220> FEATURE:
<223> OTHER INFORMATION: Synthetic Primer

<400> SEQUENCE: 13
acagcatcca gaccctgaag                                                 20
```

```
<210> SEQ ID NO 14
<211> LENGTH: 20
<212> TYPE: DNA
<213> ORGANISM: Artificial sequence
<220> FEATURE:
<223> OTHER INFORMATION: Synthetic Primer

<400> SEQUENCE: 14
gaaatccaac ttggccttga                                                    20

<210> SEQ ID NO 15
<211> LENGTH: 21
<212> TYPE: DNA
<213> ORGANISM: Artificial sequence
<220> FEATURE:
<223> OTHER INFORMATION: Synthetic Primer

<400> SEQUENCE: 15
tttttacctc tgggcctgtt t                                                  21

<210> SEQ ID NO 16
<211> LENGTH: 24
<212> TYPE: DNA
<213> ORGANISM: Artificial sequence
<220> FEATURE:
<223> OTHER INFORMATION: Synthetic Primer

<400> SEQUENCE: 16
cccagaaaga gtagaagagg tctg                                               24

<210> SEQ ID NO 17
<211> LENGTH: 20
<212> TYPE: DNA
<213> ORGANISM: Artificial sequence
<220> FEATURE:
<223> OTHER INFORMATION: Synthetic Primer

<400> SEQUENCE: 17
gtgtcagctc caggttcagg                                                    20

<210> SEQ ID NO 18
<211> LENGTH: 20
<212> TYPE: DNA
<213> ORGANISM: Artificial sequence
<220> FEATURE:
<223> OTHER INFORMATION: Synthetic Primer

<400> SEQUENCE: 18
tgtcccagaa acaccaaaca                                                    20

<210> SEQ ID NO 19
<211> LENGTH: 19
<212> TYPE: DNA
<213> ORGANISM: Artificial sequence
<220> FEATURE:
<223> OTHER INFORMATION: Synthetic Primer

<400> SEQUENCE: 19
cgttgctggt cacattcct                                                     19

<210> SEQ ID NO 20
<211> LENGTH: 19
<212> TYPE: DNA
<213> ORGANISM: Artificial sequence
<220> FEATURE:
<223> OTHER INFORMATION: Synthetic Primer
```

```
<400> SEQUENCE: 20
tcagttcctg ggtgacctg                                                          19

<210> SEQ ID NO 21
<211> LENGTH: 20
<212> TYPE: DNA
<213> ORGANISM: Artificial sequence
<220> FEATURE:
<223> OTHER INFORMATION: Synthetic Primer

<400> SEQUENCE: 21
cggagagcag gcaattaaag                                                         20

<210> SEQ ID NO 22
<211> LENGTH: 20
<212> TYPE: DNA
<213> ORGANISM: Artificial sequence
<220> FEATURE:
<223> OTHER INFORMATION: Synthetic Primer

<400> SEQUENCE: 22
gccaatttct tcgtgactcc                                                         20

<210> SEQ ID NO 23
<211> LENGTH: 21
<212> TYPE: DNA
<213> ORGANISM: Artificial sequence
<220> FEATURE:
<223> OTHER INFORMATION: Synthetic Primer

<400> SEQUENCE: 23
tgcgacagag acaataagca a                                                       21

<210> SEQ ID NO 24
<211> LENGTH: 20
<212> TYPE: DNA
<213> ORGANISM: Artificial sequence
<220> FEATURE:
<223> OTHER INFORMATION: Synthetic Primer

<400> SEQUENCE: 24
aatccacttg tttgctgctg                                                         20

<210> SEQ ID NO 25
<211> LENGTH: 20
<212> TYPE: DNA
<213> ORGANISM: Artificial sequence
<220> FEATURE:
<223> OTHER INFORMATION: Synthetic Primer

<400> SEQUENCE: 25
gtaacccgtt gaaccccatt                                                         20

<210> SEQ ID NO 26
<211> LENGTH: 20
<212> TYPE: DNA
<213> ORGANISM: Artificial sequence
<220> FEATURE:
<223> OTHER INFORMATION: Synthetic Primer

<400> SEQUENCE: 26
ccatccaatc ggtagtagcg                                                         20

<210> SEQ ID NO 27
```

```
<211> LENGTH: 83
<212> TYPE: DNA
<213> ORGANISM: Artificial sequence
<220> FEATURE:
<223> OTHER INFORMATION: Synthetic sequence

<400> SEQUENCE: 27
ggcccggcuc cgggucucgg cccguacagu ccggccggcc augcuggcgg ggcuggggcc    60
ggggccgagc ccgcggcggg gcc                                            83

<210> SEQ ID NO 28
<211> LENGTH: 31
<212> TYPE: DNA
<213> ORGANISM: Artificial sequence
<220> FEATURE:
<223> OTHER INFORMATION: Synthetic Primer

<400> SEQUENCE: 28
tcgaggatcc gtgctggtgg tcccgctgtg t                                   31

<210> SEQ ID NO 29
<211> LENGTH: 31
<212> TYPE: DNA
<213> ORGANISM: Artificial sequence
<220> FEATURE:
<223> OTHER INFORMATION: Synthetic Primer

<400> SEQUENCE: 29
tcgagctagc ttggggacga gagagggcgc g                                   31

<210> SEQ ID NO 30
<211> LENGTH: 80
<212> TYPE: DNA
<213> ORGANISM: Artificial sequence
<220> FEATURE:
<223> OTHER INFORMATION: Synthetic sequence

<400> SEQUENCE: 30
tgagaggccg caccttgcct tgctgcccgg gccgtgcacc cgtgggcccc agggcgacgc    60
ggcgggggcg gccctagcga                                                80

<210> SEQ ID NO 31
<211> LENGTH: 29
<212> TYPE: DNA
<213> ORGANISM: Artificial sequence
<220> FEATURE:
<223> OTHER INFORMATION: Synthetic Primer

<400> SEQUENCE: 31
tcgacatatg caagaagatg caatcgcgg                                      29

<210> SEQ ID NO 32
<211> LENGTH: 31
<212> TYPE: DNA
<213> ORGANISM: Artificial sequence
<220> FEATURE:
<223> OTHER INFORMATION: Synthetic Primer

<400> SEQUENCE: 32
tcgaaagctt gagaaaccac agagccttct c                                   31
```